US009868771B2

(12) United States Patent
Johnson et al.

(10) Patent No.: US 9,868,771 B2

(45) Date of Patent: Jan. 16, 2018

(54) PEPTIDES AND COMPOSITIONS FOR TREATMENT OF JOINT DAMAGE

(71) Applicants: Kristen Johnson, San Diego, CA (US); Jian Shi, San Diego, CA (US)

(72) Inventors: Kristen Johnson, San Diego, CA (US); Jian Shi, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/052,029

(22) Filed: Feb. 24, 2016

(65) Prior Publication Data

US 2016/0244491 A1 Aug. 25, 2016

Related U.S. Application Data

(62) Division of application No. 14/201,694, filed on Mar. 7, 2014, now Pat. No. 9,301,971.

(60) Provisional application No. 61/775,400, filed on Mar. 8, 2013.

(51) Int. Cl.

| | |
|---|---|
| ***A61K 38/00*** | (2006.01) |
| ***A61K 38/16*** | (2006.01) |
| ***A61K 38/18*** | (2006.01) |
| ***C07K 14/515*** | (2006.01) |
| ***A61K 45/06*** | (2006.01) |
| ***A61K 31/728*** | (2006.01) |
| ***A61K 38/17*** | (2006.01) |
| ***A61K 38/38*** | (2006.01) |
| ***A61K 38/45*** | (2006.01) |
| ***C07K 14/47*** | (2006.01) |
| ***A61K 35/32*** | (2015.01) |
| ***C12N 5/077*** | (2010.01) |
| ***C12Q 1/68*** | (2006.01) |
| ***G01N 33/68*** | (2006.01) |

(52) U.S. Cl.

CPC .......... *C07K 14/515* (2013.01); *A61K 31/728* (2013.01); *A61K 35/32* (2013.01); *A61K 38/1709* (2013.01); *A61K 38/1891* (2013.01); *A61K 38/385* (2013.01); *A61K 38/45* (2013.01); *A61K 45/06* (2013.01); *C07K 14/47* (2013.01); *C12N 5/0655* (2013.01); *C12Q 1/6883* (2013.01); *G01N 33/6887* (2013.01); *A61K 38/00* (2013.01); *C07K 2319/30* (2013.01); *C12N 2501/17* (2013.01); *C12N 2506/1346* (2013.01); *C12Q 2600/118* (2013.01); *C12Q 2600/158* (2013.01); *G01N 2333/78* (2013.01); *G01N 2800/105* (2013.01); *G01N 2800/52* (2013.01)

(58) Field of Classification Search

None

See application file for complete search history.

(56) References Cited

U.S. PATENT DOCUMENTS

| | | | |
|---|---|---|---|
| 5,567,440 | A | 10/1996 | Hubbell et al. |
| 6,030,831 | A | 2/2000 | Godowski et al. |
| 6,348,351 | B1 | 2/2002 | Fong et al. |
| 7,267,819 | B2 | 9/2007 | Ferrara et al. |
| 7,807,464 | B2 | 10/2010 | Zhang et al. |
| 9,301,972 | B2 | 4/2016 | Miyamoto |
| 2003/0068627 | A1 | 4/2003 | Rosen et al. |
| 2003/0120056 | A1 | 6/2003 | Goddard et al. |
| 2003/0215451 | A1 | 11/2003 | Ferrara et al. |
| 2004/0116649 | A1 | 6/2004 | Kozlowski |
| 2005/0054563 | A1 | 3/2005 | Desnoyer et al. |
| 2007/0020757 | A1 | 1/2007 | Ihang et al. |
| 2007/0122881 | A1 | 5/2007 | Surber |
| 2007/0134250 | A1 | 6/2007 | Ferrara et al. |
| 2009/0098117 | A1 | 4/2009 | Ferrara et al. |
| 2011/0097330 | A1 | 4/2011 | Horner et al. |
| 2012/0177644 | A1 | 7/2012 | Schultz et al. |
| 2014/0256643 | A1 | 9/2014 | Johnson et al. |

FOREIGN PATENT DOCUMENTS

| | | | |
|---|---|---|---|
| WO | 1999058660 | A1 | 11/1998 |
| WO | 1999055869 | A1 | 11/1999 |
| WO | 1999067382 | A2 | 12/1999 |
| WO | 2000053757 | A2 | 9/2000 |
| WO | 2001005972 | A1 | 1/2001 |
| WO | 2002083851 | A2 | 10/2002 |
| WO | 2003044172 | A2 | 5/2003 |
| WO | 2006127809 | A2 | 11/2006 |
| WO | 2008137641 | A2 | 11/2008 |
| WO | 2011008773 | A2 | 1/2011 |
| WO | 2012129562 | A | 9/2012 |
| WO | 2014004465 | A1 | 1/2014 |

OTHER PUBLICATIONS http://www.orthop.washington.edu/orthodev/drupal/sites/default/files/Portals/21/LiveContent/7659/Images/figure1.gif, accessed May 17, 2017.*

Wilder, et al., "Integrin alpha V beta 3 as a target for treatment of rheumatoid arthritis and related rheumatic diseases", Ann Rheum Dis, Nov. 2002, vol. 61, No. 2, pp. 96-99.

Zheng, et al., "Angiopoietin-Like 3 Deficient Bone Marrow has Decreased Ability to Support Hemaotpoietic Stem Cells", Blood, Nov. 16, 2008, vol. 112, No. 11, pp. 490.

Camenish, et al., "ANGPTL3 Stimulates Endothelial Cell Adhesion and Migration via Integrin avb3 and Induces Blood Vessel Formation in Vivo", JBC, May 10, 2002, vol. 277, No. 19, pp. 17281-17290.

(Continued)

*Primary Examiner* — Elizabeth C. Kemmerer

(74) *Attorney, Agent, or Firm* — Xiaoguang Gao

(57) ABSTRACT

The present invention provides new protease resistant polypeptides, as well as compositions and methods for treating, ameliorating or preventing conditions related to joint damage, including acute joint injury and arthritis.

21 Claims, 10 Drawing Sheets

(56) References Cited

OTHER PUBLICATIONS

Conklin, et al., "Angiopoietin-Related Protein 3 (*Homo sapiens*)", GenBank Direct Submission Accession: AAD34156, Jan. 28, 2000 (retrieved on Jun. 16, 2011), retrieved from the internet http://www.ncbi.nlm.nih.gov/protein/AAD34156, p. 1.
Conklin, et al., "Angiopoietin-Related Protein 3 Precursor (Angiopoietin-Like 3)", Uniprot Direct Submission Accession: Q9R182 (online). Jun. 15, 2002 (retrieved on Jun. 16, 2011), http://uniprot.org/uniprot/Q9R182.txt?version=9, p. 1.
Oike, et al;, "Angiopoietin-Related/Angiopoietin-Like Proteins Refulate Angiogenesis", International Journal of Hematology, 2004, vol. 80, pp. 21-28.
Phinney, et al., "Biochemical Heterogeneity of Mesenchymal Stem Cell Populations", Cell Cycle, Dec. 1, 2007, vol. 6, No. 23, pp. 2884-2889. Landes Bioscience.
Hato et al., "The Role of Angiopoietin-Like Proteins in Angiogenesis and Metabolism", Trends in Cardiovascular Medicine, Jan. 16, 2008, vol. 18, No. 1.
Chen, et al., "Angiopoietin-like protein 3 cDNA from goat", GenBank Direct Submission ACT67418, Jun. 21, 2009, http://www.ncbi.nlm.nih.gov/protein/ACT67418.1.
O'Shea, et al. "Synthesis of Trypsin-Resistant Variants of the Listeria-Active Bacteriocin Salivaricin P", Applied and Environmental Microbiology, Aug. 2010, vol. 76, No. 16, pp. 5356-5362.
Siepen, et al., "Prediction of Missed Cleavage Sites in Tryptic Peptides Aids Protein Identification in Protemics", Journal of Proteome Research, 2007, vol. 6, pp. 399-408.
Schminke, et al., "Cartilage Repair in Vivo: The Role of Migratory Progenitor Cells", Curr. Rheumatol. Rep., 2004, col. 16, No. 461, pp. 1-8.
Khan et al., "One Flew Over the Progenitor's Nest: Migratory Cells Find a Home in Osteoarthritic Cartilage", Cell Stem Cell, Apr. 2009, vol. 4, pp. 282-284.
Valenzuela, et al., "Angiopoietins 3 and 4: Diverging gene counterparts in mice and humans", Proceedings of the National Academy of Sciences of the United States of America, 1999, vol. 96, No. 5, pp. 1904-1909.
Qvist, et al., "The disease modifying osteoarthritis drug (DMOAD): Is it in the horizon?", Pharmacological Research, 2008, vol. 58, pp. 1-7.
Gerwin et al., "The OARSI histopathology initiative—recommendations for histological assessments of osteoarthritis in the rat", Osteoarthritis and Cartilage, 2010, vol. 18, pp. 524-534.
Moore, et al., "Fibroblast growth factor-18 stimulates chondrogenesis and cartilage repair in a rat model of injury-induced osteoarthritis", Osteoarthritis and Cartilage, 2005, pp. 623-631.
Database Accession No. XP_001501115.1; Jun. 25, 2007; Predicted: similar to angiopoietin-related protein 3 [Equus caballus]; http://www.ncbi.nlm.nih.gov/protein/149709517?sat=12 &satkey=5358126.
Database Accession NP_01073814.1; Feb. 24, 2008; "angiopoietin-like 3 [Bos taurus]" http://www.ncbi.nlm.nih.gov/protein/122692391?sat=13&satkey=11158563.
Database Accession NP_038941.1, Dec. 30, 2007; angiopoietin-like 3 [Mus musculus]; http://www.ncbi.nlm.nih.gov/protein/33469117?sat=12%satkey=1625442.
McGregor, Duncan Patrick., "Discovering and improving novel peptide therapeutics", Current Opinion in Pharmacology, vol. 8 (5):616-619, 2008.
Conklin, et al., "Identification of a Mammalian Angiopoietin-Related Protein Expressed Specifically in Liver", Genomics, Dec. 1999, vol. 62, No. 3, pp. 477-482.

* cited by examiner

SEQUENCE LISTING

<160> NUMBER OF SEQ ID NOS: 57

<210> SEQ ID NO 1
<211> LENGTH: 460
<212> TYPE: PRT
<213> ORGANISM: Homo sapiens

<400> SEQUENCE: 1

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln

-continued

```
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460


<210> SEQ ID NO 2
<211> LENGTH: 2126
<212> TYPE: DNA
<213> ORGANISM: Homo sapiens

<400> SEQUENCE: 2

ttccagaaga aaacagttcc acgttgcttg aaattgaaaa tcaagataaa aatgttcaca      60

attaagctcc ttctttttat tgttcctcta gttatttcct ccagaattga tcaagacaat     120

tcatcatttg attctctatc tccagagcca aaatcaagat ttgctatgtt agacgatgta     180

aaaattttag ccaatggcct ccttcagttg ggacatggtc ttaaagactt tgtccataag     240

acgaagggcc aaattaatga catatttcaa aaactcaaca tatttgatca gtctttttat     300

gatctatcgc tgcaaaccag tgaaatcaaa gaagaagaaa aggaactgag aagaactaca     360

tataaactac aagtcaaaaa tgaagaggta aagaatatgt cacttgaact caactcaaaa     420

cttgaaagcc tcctagaaga aaaaattcta cttcaacaaa aagtgaaata tttagaagag     480

caactaacta acttaattca aaatcaacct gaaactccag aacacccaga agtaacttca     540
```

-continued

```
cttaaaactt ttgtagaaaa acaagataat agcatcaaag accttctcca gaccgtggaa    600

gaccaatata aacaattaaa ccaacagcat agtcaaataa aagaaataga aaatcagctc    660

agaaggacta gtattcaaga acccacagaa atttctctat cttccaagcc aagagcacca    720

agaactactc cctttcttca gttgaatgaa ataagaaatg taaaacatga tggcattcct    780

gctgaatgta ccaccattta taacagaggt gaacatacaa gtggcatgta tgccatcaga    840

cccagcaact ctcaagtttt tcatgtctac tgtgatgtta tatcaggtag tccatggaca    900

ttaattcaac atcgaataga tggatcacaa aacttcaatg aaacgtggga gaactacaaa    960

tatggttttg ggaggcttga tggagaattt tggttgggcc tagagaagat atactccata   1020

gtgaagcaat ctaattatgt tttacgaatt gagttggaag actggaaaga caacaaacat   1080

tatattgaat attcttttta cttgggaaat cacgaaacca actatacgct acatctagtt   1140

gcgattactg gcaatgtccc caatgcaatc ccggaaaaca aagatttggt gttttctact   1200

tgggatcaca aagcaaaagg acacttcaac tgtccagagg gttattcagg aggctggtgg   1260

tggcatgatg agtgtggaga aaacaaccta aatggtaaat ataacaaacc aagagcaaaa   1320

tctaagccag agaggagaag aggattatct tggaagtctc aaaatggaag gttatactct   1380

ataaaatcaa ccaaaatgtt gatccatcca acagattcag aaagctttga atgaactgag   1440

gcaaatttaa aaggcaataa tttaaacatt aacctcattc caagttaatg tggtctaata   1500

atctggtatt aaatccttaa gagaaagctt gagaaataga tttttttttat cttaaagtca   1560

ctgtctattt aagattaaac atacaatcac ataaccttaa agaataccgt ttacatttct   1620

caatcaaaat tcttataata ctatttgttt taaattttgt gatgtgggaa tcaattttag   1680

atggtcacaa tctagattat aatcaatagg tgaacttatt aaataacttt tctaaataaa   1740

aaatttagag acttttattt taaaaggcat catatgagct aatatcacaa ctttcccagt   1800

ttaaaaaact agtactcttg ttaaaactct aaacttgact aaatacagag gactggtaat   1860

tgtacagttc ttaaatgttg tagtattaat ttcaaaacta aaaatcgtca gcacagagta   1920

tgtgtaaaaa tctgtaatac aaatttttaa actgatgctt cattttgcta caaaataatt   1980

tggagtaaat gtttgatatg atttatttat gaaacctaat gaagcagaat taaatactgt   2040

attaaaataa gttcgctgtc tttaaacaaa tggagatgac tactaagtca cattgacttt   2100

aacatgaggt atcactatac cttatt                                        2126
```

```
<210> SEQ ID NO 3
<211> LENGTH: 455
<212> TYPE: PRT
<213> ORGANISM: Mus musculus

<400> SEQUENCE: 3

Met His Thr Ile Lys Leu Phe Leu Phe Val Val Pro Leu Val Ile Ala
1               5                   10                  15

Ser Arg Val Asp Pro Asp Leu Ser Ser Phe Asp Ser Ala Pro Ser Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Arg Thr Asn Glu Ile Lys Glu Glu Glu
                85                  90                  95
```

```
Lys Glu Leu Arg Arg Thr Thr Ser Thr Leu Gln Val Lys Asn Glu Glu
            100                 105                 110

Val Lys Asn Met Ser Val Glu Leu Asn Ser Lys Leu Glu Ser Leu Leu
        115                 120                 125

Glu Glu Lys Thr Ala Leu Gln His Lys Val Arg Ala Leu Glu Glu Gln
    130                 135                 140

Leu Thr Asn Leu Ile Leu Ser Pro Ala Gly Ala Gln Glu His Pro Glu
145                 150                 155                 160

Val Thr Ser Leu Lys Ser Phe Val Glu Gln Gln Asp Asn Ser Ile Arg
                165                 170                 175

Glu Leu Leu Gln Ser Val Glu Glu Gln Tyr Lys Gln Leu Ser Gln Gln
            180                 185                 190

His Met Gln Ile Lys Glu Ile Glu Lys Gln Leu Arg Lys Thr Gly Ile
        195                 200                 205

Gln Glu Pro Ser Glu Asn Ser Leu Ser Ser Lys Ser Arg Ala Pro Arg
    210                 215                 220

Thr Thr Pro Pro Leu Gln Leu Asn Glu Thr Glu Asn Thr Glu Gln Asp
225                 230                 235                 240

Asp Leu Pro Ala Asp Cys Ser Ala Val Tyr Asn Arg Gly Glu His Thr
                245                 250                 255

Ser Gly Val Tyr Thr Ile Lys Pro Arg Asn Ser Gln Gly Phe Asn Val
            260                 265                 270

Tyr Cys Asp Thr Gln Ser Gly Ser Pro Trp Thr Leu Ile Gln His Arg
        275                 280                 285

Lys Asp Gly Ser Gln Asp Phe Asn Glu Thr Trp Glu Asn Tyr Glu Lys
    290                 295                 300

Gly Phe Gly Arg Leu Asp Gly Glu Phe Trp Leu Gly Leu Glu Lys Ile
305                 310                 315                 320

Tyr Ala Ile Val Gln Gln Ser Asn Tyr Ile Leu Arg Leu Glu Leu Gln
                325                 330                 335

Asp Trp Lys Asp Ser Lys His Tyr Val Glu Tyr Ser Phe His Leu Gly
            340                 345                 350

Ser His Glu Thr Asn Tyr Thr Leu His Val Ala Glu Ile Ala Gly Asn
        355                 360                 365

Ile Pro Gly Ala Leu Pro Glu His Thr Asp Leu Met Phe Ser Thr Trp
    370                 375                 380

Asn His Arg Ala Lys Gly Gln Leu Tyr Cys Pro Glu Ser Tyr Ser Gly
385                 390                 395                 400

Gly Trp Trp Trp Asn Asp Ile Cys Gly Glu Asn Asn Leu Asn Gly Lys
                405                 410                 415

Tyr Asn Lys Pro Arg Thr Lys Ser Arg Pro Glu Arg Arg Arg Gly Ile
            420                 425                 430

Tyr Trp Arg Pro Gln Ser Arg Lys Leu Tyr Ala Ile Lys Ser Ser Lys
        435                 440                 445

Met Met Leu Gln Pro Thr Thr
    450                 455
```

<210> SEQ ID NO 4
<211> LENGTH: 459
<212> TYPE: PRT
<213> ORGANISM: Canis familiaris

<400> SEQUENCE: 4

```
Met Tyr Thr Ile Lys Leu Phe Leu Phe Ile Ile Pro Leu Val Ile Ser
```

-continued

```
1               5                   10                  15

Ser Lys Ile Asp Arg Asp Tyr Ser Ser Tyr Asp Ser Val Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Asn Glu Ile Lys Glu Glu Glu
                85                  90                  95

Lys Glu Leu Arg Arg Thr Thr Ser Lys Leu Gln Val Lys Asn Glu Glu
            100                 105                 110

Val Lys Asn Met Ser Leu Glu Leu Asn Ser Lys Val Glu Ser Leu Leu
        115                 120                 125

Glu Glu Lys Ile Leu Leu Gln Gln Lys Val Arg Tyr Leu Glu Lys Gln
    130                 135                 140

Leu Thr Ser Leu Ile Lys Asn Gln Pro Glu Ile Gln Glu His Pro Glu
145                 150                 155                 160

Val Thr Ser Leu Lys Thr Phe Val Glu Gln Gln Asp Asn Ser Ile Lys
                165                 170                 175

Asp Leu Leu Gln Thr Val Glu Glu Gln Tyr Arg Gln Leu Asn Gln Gln
            180                 185                 190

His Ser Gln Ile Lys Glu Ile Glu Asn Gln Leu Arg Asn Val Ile Gln
        195                 200                 205

Glu Ser Thr Glu Asn Ser Leu Ser Ser Lys Pro Arg Ala Pro Arg Thr
    210                 215                 220

Thr Pro Phe Leu His Leu Asn Glu Thr Lys Asn Val Glu His Asn Asp
225                 230                 235                 240

Ile Pro Ala Asn Cys Thr Thr Ile Tyr Asn Arg Gly Glu His Thr Ser
                245                 250                 255

Gly Ile Tyr Ser Ile Arg Pro Ser Asn Ser Gln Val Phe Asn Val Tyr
            260                 265                 270

Cys Asp Val Lys Ser Gly Ser Ser Trp Thr Leu Ile Gln His Arg Ile
        275                 280                 285

Asp Gly Ser Gln Asn Phe Asn Glu Thr Trp Glu Asn Tyr Arg Tyr Gly
    290                 295                 300

Phe Gly Arg Leu Asp Gly Glu Phe Trp Leu Gly Leu Glu Lys Ile Tyr
305                 310                 315                 320

Ser Ile Val Lys Gln Ser Asn Tyr Ile Leu Arg Ile Glu Leu Glu Asp
                325                 330                 335

Trp Asn Asp Asn Lys His Tyr Ile Glu Tyr Phe Phe His Leu Gly Asn
            340                 345                 350

His Glu Thr Asn Tyr Thr Leu His Leu Val Glu Ile Thr Gly Asn Ile
        355                 360                 365

Leu Asn Ala Leu Pro Glu His Lys Asp Leu Val Phe Ser Thr Trp Asp
    370                 375                 380

His Lys Ala Lys Gly His Val Asn Cys Pro Glu Ser Tyr Ser Gly Gly
385                 390                 395                 400

Trp Trp Trp His Asn Val Cys Gly Glu Asn Asn Leu Asn Gly Lys Tyr
                405                 410                 415

Asn Lys Gln Arg Ala Lys Thr Lys Pro Glu Arg Arg Arg Gly Leu Tyr
            420                 425                 430
```

```
Trp Lys Ser Gln Asn Gly Arg Leu Tyr Ser Ile Lys Ser Thr Lys Met
        435                 440                 445

Leu Ile His Pro Ile Asp Ser Glu Ser Ser Glu
    450                 455


<210> SEQ ID NO 5
<211> LENGTH: 469
<212> TYPE: PRT
<213> ORGANISM: Equus caballus

<400> SEQUENCE: 5

Met Tyr Thr Ile Lys Leu Phe Leu Val Ile Ala Pro Leu Val Ile Ser
1               5                   10                  15

Ser Arg Ile Asp Gln Asp Tyr Ser Ser Leu Asp Ser Ile Pro Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Ala Leu Ser Leu Gln Thr Asn Glu Ile Lys Glu Glu Glu
                85                  90                  95

Lys Glu Leu Arg Arg Thr Thr Ser Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ser Leu Leu Gln Gln Lys Val Lys Tyr Leu Glu Glu Gln
    130                 135                 140

Leu Thr Lys Leu Ile Lys Asn Gln Pro Glu Ile Gln Glu His Pro Glu
145                 150                 155                 160

Val Thr Ser Leu Lys Thr Phe Val Glu Gln Gln Asp Asn Ser Ile Lys
                165                 170                 175

Asp Leu Leu Gln Thr Met Glu Glu Gln Tyr Arg Gln Leu Asn Gln Gln
            180                 185                 190

His Ser Gln Ile Lys Glu Ile Glu Asn Gln Leu Arg Arg Thr Gly Ile
        195                 200                 205

Gln Glu Ser Thr Glu Asn Ser Leu Ser Ser Lys Pro Arg Ala Pro Arg
    210                 215                 220

Thr Thr Pro Ser Phe His Leu Asn Glu Thr Lys Asp Val Glu His Asp
225                 230                 235                 240

Asp Phe Pro Ala Asp Cys Thr Thr Ile Tyr Asn Arg Gly Glu His Thr
                245                 250                 255

Ser Gly Ile Tyr Ser Ile Lys Pro Ser Asn Ser Gln Val Phe Asn Val
            260                 265                 270

Tyr Cys Asp Val Ile Ser Gly Ser Ser Trp Ile Leu Ile Gln Arg Arg
        275                 280                 285

Ile Asp Gly Ser Gln Asn Phe Asn Glu Thr Trp Gln Asn Tyr Lys Tyr
    290                 295                 300

Gly Phe Gly Arg Leu Asp Phe Glu Phe Trp Leu Gly Leu Glu Lys Ile
305                 310                 315                 320

Tyr Ser Ile Val Lys Arg Ser Asn Tyr Ile Leu Arg Ile Glu Leu Glu
                325                 330                 335

Asp Trp Lys Asp Asn Lys His Thr Ile Glu Tyr Ser Phe His Leu Gly
```

```
            340                 345                 350

Asn His Glu Thr Asn Tyr Thr Leu His Leu Val Glu Ile Thr Gly Asn
        355                 360                 365

Val Pro Asn Ala Leu Pro Glu His Lys Asp Leu Val Phe Ser Thr Trp
    370                 375                 380

Asp His Lys Ala Lys Gly Gln Leu Asn Cys Leu Glu Ser Tyr Ser Gly
385                 390                 395                 400

Gly Trp Trp Trp His Asp Val Cys Gly Gly Asp Asn Pro Asn Gly Lys
                405                 410                 415

Tyr Asn Lys Pro Arg Ser Lys Thr Lys Pro Glu Arg Arg Arg Gly Ile
            420                 425                 430

Cys Trp Lys Ser Gln Asn Gly Arg Leu Tyr Thr Ile Lys Ser Thr Lys
        435                 440                 445

Met Leu Ile His Pro Ile Asp Ser Glu Ser Phe Glu Leu Arg Gln Ile
    450                 455                 460

Lys Lys Pro Met Asn
465


<210> SEQ ID NO 6
<211> LENGTH: 459
<212> TYPE: PRT
<213> ORGANISM: Bos taurus

<400> SEQUENCE: 6

Met Tyr Thr Ile Lys Leu Phe Leu Ile Ile Ala Pro Leu Val Ile Ser
1               5                   10                  15

Ser Arg Thr Asp Gln Asp Tyr Thr Ser Leu Asp Ser Ile Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Asn Glu Ile Lys Glu Glu Glu
                85                  90                  95

Lys Glu Leu Arg Arg Ala Thr Ser Lys Leu Gln Val Lys Asn Glu Glu
            100                 105                 110

Val Lys Asn Met Ser Leu Glu Leu Asp Ser Lys Leu Glu Ser Leu Leu
        115                 120                 125

Glu Glu Lys Ile Leu Leu Gln Gln Lys Val Arg Tyr Leu Glu Asp Gln
    130                 135                 140

Leu Thr Asp Leu Ile Lys Asn Gln Pro Gln Ile Gln Glu Tyr Leu Glu
145                 150                 155                 160

Val Thr Ser Leu Lys Thr Leu Val Glu Gln Gln Asp Asn Ser Ile Lys
                165                 170                 175

Asp Leu Leu Gln Ile Val Glu Glu Gln Tyr Arg Gln Leu Asn Gln Gln
            180                 185                 190

Gln Ser Gln Ile Lys Glu Ile Glu Asn Gln Leu Arg Arg Thr Gly Ile
        195                 200                 205

Lys Glu Ser Thr Glu Ile Ser Leu Ser Ser Lys Pro Arg Ala Pro Arg
    210                 215                 220

Thr Thr Pro Ser Phe His Ser Asn Glu Thr Lys Asn Val Glu His Asp
225                 230                 235                 240
```

-continued

Asp Ile Pro Ala Asp Cys Thr Ile Ile Tyr Asn Gln Gly Lys His Thr
245 250 255

Ser Gly Ile Tyr Ser Ile Arg Pro Ser Asn Ser Gln Val Phe Asn Val
260 265 270

Tyr Cys Asp Val Lys Ser Gly Ser Ser Trp Thr Leu Ile Gln His Arg
275 280 285

Ile Asp Gly Ser Gln Asn Phe Asn Glu Thr Trp Glu Asn Tyr Lys Tyr
290 295 300

Gly Phe Gly Arg Leu Asp Gly Glu Phe Trp Leu Gly Leu Glu Lys Ile
305 310 315 320

Tyr Ser Ile Val Met Gln Ser Asn Tyr Ile Leu Arg Ile Glu Leu Glu
325 330 335

Asp Trp Lys Asp Lys Tyr Tyr Thr Glu Tyr Ser Phe His Leu Gly Asp
340 345 350

His Glu Thr Asn Tyr Thr Leu His Leu Ala Glu Ile Ser Gly Asn Gly
355 360 365

Pro Lys Ala Phe Pro Glu His Lys Asp Leu Met Phe Ser Thr Trp Asp
370 375 380

His Lys Ala Lys Gly His Phe Asn Cys Pro Glu Ser Asn Ser Gly Gly
385 390 395 400

Trp Trp Tyr His Asp Val Cys Gly Glu Asn Asn Leu Asn Gly Lys Tyr
405 410 415

Asn Lys Pro Lys Ala Lys Ala Lys Pro Glu Arg Lys Glu Gly Ile Cys
420 425 430

Trp Lys Ser Gln Asp Gly Arg Leu Tyr Ser Ile Lys Ala Thr Lys Met
435 440 445

Leu Ile His Pro Ser Asp Ser Glu Asn Ser Glu
450 455

<210> SEQ ID NO 7
<211> LENGTH: 248
<212> TYPE: PRT
<213> ORGANISM: Artificial Sequence
<220> FEATURE:
<223> OTHER INFORMATION: 207-455WT

<400> SEQUENCE: 7

Ile Gln Glu Pro Thr Glu Ile Ser Leu Ser Ser Lys Pro Arg Ala Pro
1 5 10 15

Arg Thr Thr Pro Phe Leu Gln Leu Asn Glu Ile Arg Asn Val Lys His
20 25 30

Asp Gly Ile Pro Ala Glu Cys Thr Thr Ile Tyr Asn Arg Gly Glu His
35 40 45

Thr Ser Gly Met Tyr Ala Ile Arg Pro Ser Asn Ser Gln Val Phe His
50 55 60

Val Tyr Cys Asp Val Ile Ser Gly Ser Pro Trp Thr Leu Ile Gln His
65 70 75 80

Arg Ile Asp Gly Ser Gln Asn Phe Asn Glu Thr Trp Glu Asn Tyr Lys
85 90 95

Tyr Gly Phe Gly Arg Leu Asp Gly Glu Phe Trp Leu Gly Leu Glu Lys
100 105 110

Ile Tyr Ser Ile Val Lys Gln Ser Asn Tyr Val Leu Arg Ile Glu Leu
115 120 125

Glu Asp Trp Lys Asp Asn Lys His Tyr Ile Glu Tyr Ser Phe Tyr Leu
130 135 140

```
Gly Asn His Glu Thr Asn Tyr Thr Leu His Leu Val Ala Ile Thr Gly
145                 150                 155                 160

Asn Val Pro Asn Ala Ile Pro Glu Asn Lys Asp Leu Val Phe Ser Thr
                165                 170                 175

Trp Asp His Lys Ala Lys Gly His Phe Asn Cys Pro Glu Gly Tyr Ser
            180                 185                 190

Gly Gly Trp Trp Trp His Asp Glu Cys Gly Glu Asn Asn Leu Asn Gly
        195                 200                 205

Lys Tyr Asn Lys Pro Arg Ala Lys Ser Lys Pro Glu Arg Arg Arg Gly
    210                 215                 220

Leu Ser Trp Lys Ser Gln Asn Gly Arg Leu Tyr Ser Ile Lys Ser Thr
225                 230                 235                 240

Lys Met Leu Ile His Pro Thr Asp
                245


<210> SEQ ID NO 8
<211> LENGTH: 231
<212> TYPE: PRT
<213> ORGANISM: Artificial Sequence
<220> FEATURE:
<223> OTHER INFORMATION: 225-455WT

<400> SEQUENCE: 8

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
        115                 120                 125

Asn His Glu Thr Asn Tyr Thr Leu His Leu Val Ala Ile Thr Gly Asn
    130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Lys Ser Lys Pro Glu Arg Arg Arg Gly Leu
        195                 200                 205

Ser Trp Lys Ser Gln Asn Gly Arg Leu Tyr Ser Ile Lys Ser Thr Lys
    210                 215                 220

Met Leu Ile His Pro Thr Asp
225                 230


<210> SEQ ID NO 9
<211> LENGTH: 228
```

```
<212> TYPE: PRT
<213> ORGANISM: Artificial Sequence
<220> FEATURE:
<223> OTHER INFORMATION: 228-455WT

<400> SEQUENCE: 9

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Lys Ser Lys Pro Glu Arg Arg Arg Gly Leu Ser Trp Lys
        195                 200                 205

Ser Gln Asn Gly Arg Leu Tyr Ser Ile Lys Ser Thr Lys Met Leu Ile
    210                 215                 220

His Pro Thr Asp
225


<210> SEQ ID NO 10
<211> LENGTH: 223
<212> TYPE: PRT
<213> ORGANISM: Artificial Sequence
<220> FEATURE:
<223> OTHER INFORMATION: 233-455WT

<400> SEQUENCE: 10

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
    50                  55                  60

Glu Thr Trp Glu Asn Tyr Lys Tyr Gly Phe Gly Arg Leu Asp Gly Glu
65                  70                  75                  80

Phe Trp Leu Gly Leu Glu Lys Ile Tyr Ser Ile Val Lys Gln Ser Asn
                85                  90                  95
```

```
Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
        115                 120                 125

His Leu Val Ala Ile Thr Gly Asn Val Pro Asn Ala Ile Pro Glu Asn
    130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp Trp His Asp Glu Cys
                165                 170                 175

Gly Glu Asn Asn Leu Asn Gly Lys Tyr Asn Lys Pro Arg Ala Lys Ser
            180                 185                 190

Lys Pro Glu Arg Arg Arg Gly Leu Ser Trp Lys Ser Gln Asn Gly Arg
        195                 200                 205

Leu Tyr Ser Ile Lys Ser Thr Lys Met Leu Ile His Pro Thr Asp
    210                 215                 220


<210> SEQ ID NO 11
<211> LENGTH: 215
<212> TYPE: PRT
<213> ORGANISM: Artificial Sequence
<220> FEATURE:
<223> OTHER INFORMATION: 241-455WT

<400> SEQUENCE: 11

Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Lys Ser Lys Pro Glu Arg Arg Arg Gly Leu
            180                 185                 190

Ser Trp Lys Ser Gln Asn Gly Arg Leu Tyr Ser Ile Lys Ser Thr Lys
        195                 200                 205

Met Leu Ile His Pro Thr Asp
    210                 215


<210> SEQ ID NO 12
```

-continued

```
<211> LENGTH: 460
<212> TYPE: PRT
<213> ORGANISM: Artificial Sequence
<220> FEATURE:
<223> OTHER INFORMATION: K423Q

<400> SEQUENCE: 12

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380
```

```
Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Gln Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460


<210> SEQ ID NO 13
<211> LENGTH: 460
<212> TYPE: PRT
<213> ORGANISM: Artificial Sequence
<220> FEATURE:
<223> OTHER INFORMATION: K423S

<400> SEQUENCE: 13

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285
```

-continued

```
Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Ser Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460


<210> SEQ ID NO 14
<211> LENGTH: 253
<212> TYPE: PRT
<213> ORGANISM: Artificial Sequence
<220> FEATURE:
<223> OTHER INFORMATION: 207-460 K423Q

<400> SEQUENCE: 14

Ile Gln Glu Pro Thr Glu Ile Ser Leu Ser Ser Lys Pro Arg Ala Pro
1               5                   10                  15

Arg Thr Thr Pro Phe Leu Gln Leu Asn Glu Ile Arg Asn Val Lys His
            20                  25                  30

Asp Gly Ile Pro Ala Glu Cys Thr Thr Ile Tyr Asn Arg Gly Glu His
        35                  40                  45

Thr Ser Gly Met Tyr Ala Ile Arg Pro Ser Asn Ser Gln Val Phe His
    50                  55                  60

Val Tyr Cys Asp Val Ile Ser Gly Ser Pro Trp Thr Leu Ile Gln His
65                  70                  75                  80

Arg Ile Asp Gly Ser Gln Asn Phe Asn Glu Thr Trp Glu Asn Tyr Lys
                85                  90                  95

Tyr Gly Phe Gly Arg Leu Asp Gly Glu Phe Trp Leu Gly Leu Glu Lys
            100                 105                 110

Ile Tyr Ser Ile Val Lys Gln Ser Asn Tyr Val Leu Arg Ile Glu Leu
        115                 120                 125

Glu Asp Trp Lys Asp Asn Lys His Tyr Ile Glu Tyr Ser Phe Tyr Leu
    130                 135                 140

Gly Asn His Glu Thr Asn Tyr Thr Leu His Leu Val Ala Ile Thr Gly
145                 150                 155                 160

Asn Val Pro Asn Ala Ile Pro Glu Asn Lys Asp Leu Val Phe Ser Thr
                165                 170                 175

Trp Asp His Lys Ala Lys Gly His Phe Asn Cys Pro Glu Gly Tyr Ser
            180                 185                 190
```

-continued

```
Gly Gly Trp Trp Trp His Asp Glu Cys Gly Glu Asn Asn Leu Asn Gly
        195                 200                 205

Lys Tyr Asn Lys Pro Arg Ala Gln Ser Lys Pro Glu Arg Arg Arg Gly
    210                 215                 220

Leu Ser Trp Lys Ser Gln Asn Gly Arg Leu Tyr Ser Ile Lys Ser Thr
225                 230                 235                 240

Lys Met Leu Ile His Pro Thr Asp Ser Glu Ser Phe Glu
                245                 250
```

<210> SEQ ID NO 15
<211> LENGTH: 253
<212> TYPE: PRT
<213> ORGANISM: Artificial Sequence
<220> FEATURE:
<223> OTHER INFORMATION: 207-460 K423S

<400> SEQUENCE: 15

```
Ile Gln Glu Pro Thr Glu Ile Ser Leu Ser Ser Lys Pro Arg Ala Pro
1               5                   10                  15

Arg Thr Thr Pro Phe Leu Gln Leu Asn Glu Ile Arg Asn Val Lys His
            20                  25                  30

Asp Gly Ile Pro Ala Glu Cys Thr Thr Ile Tyr Asn Arg Gly Glu His
        35                  40                  45

Thr Ser Gly Met Tyr Ala Ile Arg Pro Ser Asn Ser Gln Val Phe His
    50                  55                  60

Val Tyr Cys Asp Val Ile Ser Gly Ser Pro Trp Thr Leu Ile Gln His
65                  70                  75                  80

Arg Ile Asp Gly Ser Gln Asn Phe Asn Glu Thr Trp Glu Asn Tyr Lys
                85                  90                  95

Tyr Gly Phe Gly Arg Leu Asp Gly Glu Phe Trp Leu Gly Leu Glu Lys
            100                 105                 110

Ile Tyr Ser Ile Val Lys Gln Ser Asn Tyr Val Leu Arg Ile Glu Leu
        115                 120                 125

Glu Asp Trp Lys Asp Asn Lys His Tyr Ile Glu Tyr Ser Phe Tyr Leu
    130                 135                 140

Gly Asn His Glu Thr Asn Tyr Thr Leu His Leu Val Ala Ile Thr Gly
145                 150                 155                 160

Asn Val Pro Asn Ala Ile Pro Glu Asn Lys Asp Leu Val Phe Ser Thr
                165                 170                 175

Trp Asp His Lys Ala Lys Gly His Phe Asn Cys Pro Glu Gly Tyr Ser
            180                 185                 190

Gly Gly Trp Trp Trp His Asp Glu Cys Gly Glu Asn Asn Leu Asn Gly
        195                 200                 205

Lys Tyr Asn Lys Pro Arg Ala Ser Ser Lys Pro Glu Arg Arg Arg Gly
    210                 215                 220

Leu Ser Trp Lys Ser Gln Asn Gly Arg Leu Tyr Ser Ile Lys Ser Thr
225                 230                 235                 240

Lys Met Leu Ile His Pro Thr Asp Ser Glu Ser Phe Glu
                245                 250
```

<210> SEQ ID NO 16
<211> LENGTH: 236
<212> TYPE: PRT
<213> ORGANISM: Artificial Sequence
<220> FEATURE:
<223> OTHER INFORMATION: 225-460 K423Q

<400> SEQUENCE: 16

Thr Thr Pro Phe Leu Gln Leu Asn Glu Ile Arg Asn Val Lys His Asp
1 5 10 15

Gly Ile Pro Ala Glu Cys Thr Thr Ile Tyr Asn Arg Gly Glu His Thr
20 25 30

Ser Gly Met Tyr Ala Ile Arg Pro Ser Asn Ser Gln Val Phe His Val
35 40 45

Tyr Cys Asp Val Ile Ser Gly Ser Pro Trp Thr Leu Ile Gln His Arg
50 55 60

Ile Asp Gly Ser Gln Asn Phe Asn Glu Thr Trp Glu Asn Tyr Lys Tyr
65 70 75 80

Gly Phe Gly Arg Leu Asp Gly Glu Phe Trp Leu Gly Leu Glu Lys Ile
85 90 95

Tyr Ser Ile Val Lys Gln Ser Asn Tyr Val Leu Arg Ile Glu Leu Glu
100 105 110

Asp Trp Lys Asp Asn Lys His Tyr Ile Glu Tyr Ser Phe Tyr Leu Gly
115 120 125

Asn His Glu Thr Asn Tyr Thr Leu His Leu Val Ala Ile Thr Gly Asn
130 135 140

Val Pro Asn Ala Ile Pro Glu Asn Lys Asp Leu Val Phe Ser Thr Trp
145 150 155 160

Asp His Lys Ala Lys Gly His Phe Asn Cys Pro Glu Gly Tyr Ser Gly
165 170 175

Gly Trp Trp Trp His Asp Glu Cys Gly Glu Asn Asn Leu Asn Gly Lys
180 185 190

Tyr Asn Lys Pro Arg Ala Gln Ser Lys Pro Glu Arg Arg Arg Gly Leu
195 200 205

Ser Trp Lys Ser Gln Asn Gly Arg Leu Tyr Ser Ile Lys Ser Thr Lys
210 215 220

Met Leu Ile His Pro Thr Asp Ser Glu Ser Phe Glu
225 230 235

<210> SEQ ID NO 17
<211> LENGTH: 236
<212> TYPE: PRT
<213> ORGANISM: Artificial Sequence
<220> FEATURE:
<223> OTHER INFORMATION: 225-460 K423S

<400> SEQUENCE: 17

Thr Thr Pro Phe Leu Gln Leu Asn Glu Ile Arg Asn Val Lys His Asp
1 5 10 15

Gly Ile Pro Ala Glu Cys Thr Thr Ile Tyr Asn Arg Gly Glu His Thr
20 25 30

Ser Gly Met Tyr Ala Ile Arg Pro Ser Asn Ser Gln Val Phe His Val
35 40 45

Tyr Cys Asp Val Ile Ser Gly Ser Pro Trp Thr Leu Ile Gln His Arg
50 55 60

Ile Asp Gly Ser Gln Asn Phe Asn Glu Thr Trp Glu Asn Tyr Lys Tyr
65 70 75 80

Gly Phe Gly Arg Leu Asp Gly Glu Phe Trp Leu Gly Leu Glu Lys Ile
85 90 95

Tyr Ser Ile Val Lys Gln Ser Asn Tyr Val Leu Arg Ile Glu Leu Glu
100 105 110

Asp Trp Lys Asp Asn Lys His Tyr Ile Glu Tyr Ser Phe Tyr Leu Gly

```
        115                 120                 125

Asn His Glu Thr Asn Tyr Thr Leu His Leu Val Ala Ile Thr Gly Asn
    130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Ser Ser Lys Pro Glu Arg Arg Arg Gly Leu
        195                 200                 205

Ser Trp Lys Ser Gln Asn Gly Arg Leu Tyr Ser Ile Lys Ser Thr Lys
    210                 215                 220

Met Leu Ile His Pro Thr Asp Ser Glu Ser Phe Glu
225                 230                 235


<210> SEQ ID NO 18
<211> LENGTH: 236
<212> TYPE: PRT
<213> ORGANISM: Artificial Sequence
<220> FEATURE:
<223> OTHER INFORMATION: 225-460 S424T

<400> SEQUENCE: 18

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
        115                 120                 125

Asn His Glu Thr Asn Tyr Thr Leu His Leu Val Ala Ile Thr Gly Asn
    130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Lys Thr Lys Pro Glu Arg Arg Arg Gly Leu
        195                 200                 205

Ser Trp Lys Ser Gln Asn Gly Arg Leu Tyr Ser Ile Lys Ser Thr Lys
    210                 215                 220

Met Leu Ile His Pro Thr Asp Ser Glu Ser Phe Glu
225                 230                 235
```

<210> SEQ ID NO 19
<211> LENGTH: 235
<212> TYPE: PRT
<213> ORGANISM: Artificial Sequence
<220> FEATURE:
<223> OTHER INFORMATION: 226-460 K423-Q

<400> SEQUENCE: 19

```
Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
            20                  25                  30

Gly Met Tyr Ala Ile Arg Pro Ser Asn Ser Gln Val Phe His Val Tyr
        35                  40                  45

Cys Asp Val Ile Ser Gly Ser Pro Trp Thr Leu Ile Gln His Arg Ile
    50                  55                  60

Asp Gly Ser Gln Asn Phe Asn Glu Thr Trp Glu Asn Tyr Lys Tyr Gly
65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
        115                 120                 125

His Glu Thr Asn Tyr Thr Leu His Leu Val Ala Ile Thr Gly Asn Val
    130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Gln Ser Lys Pro Glu Arg Arg Arg Gly Leu Ser
        195                 200                 205

Trp Lys Ser Gln Asn Gly Arg Leu Tyr Ser Ile Lys Ser Thr Lys Met
    210                 215                 220

Leu Ile His Pro Thr Asp Ser Glu Ser Phe Glu
225                 230                 235
```

<210> SEQ ID NO 20
<211> LENGTH: 235
<212> TYPE: PRT
<213> ORGANISM: Artificial Sequence
<220> FEATURE:
<223> OTHER INFORMATION: 226-460 K423S

<400> SEQUENCE: 20

```
Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
            20                  25                  30

Gly Met Tyr Ala Ile Arg Pro Ser Asn Ser Gln Val Phe His Val Tyr
        35                  40                  45

Cys Asp Val Ile Ser Gly Ser Pro Trp Thr Leu Ile Gln His Arg Ile
    50                  55                  60

Asp Gly Ser Gln Asn Phe Asn Glu Thr Trp Glu Asn Tyr Lys Tyr Gly
65                  70                  75                  80
```

-continued

```
Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
        115                 120                 125

His Glu Thr Asn Tyr Thr Leu His Leu Val Ala Ile Thr Gly Asn Val
    130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Ser Ser Lys Pro Glu Arg Arg Arg Gly Leu Ser
        195                 200                 205

Trp Lys Ser Gln Asn Gly Arg Leu Tyr Ser Ile Lys Ser Thr Lys Met
    210                 215                 220

Leu Ile His Pro Thr Asp Ser Glu Ser Phe Glu
225                 230                 235


<210> SEQ ID NO 21
<211> LENGTH: 233
<212> TYPE: PRT
<213> ORGANISM: Artificial Sequence
<220> FEATURE:
<223> OTHER INFORMATION: 228-460 K423Q

<400> SEQUENCE: 21

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Gln Ser Lys Pro Glu Arg Arg Arg Gly Leu Ser Trp Lys
        195                 200                 205
```

-continued

```
Ser Gln Asn Gly Arg Leu Tyr Ser Ile Lys Ser Thr Lys Met Leu Ile
    210                 215                 220

His Pro Thr Asp Ser Glu Ser Phe Glu
225                 230


<210> SEQ ID NO 22
<211> LENGTH: 233
<212> TYPE: PRT
<213> ORGANISM: Artificial Sequence
<220> FEATURE:
<223> OTHER INFORMATION: 228-460 K423S

<400> SEQUENCE: 22

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Ser Ser Lys Pro Glu Arg Arg Arg Gly Leu Ser Trp Lys
        195                 200                 205

Ser Gln Asn Gly Arg Leu Tyr Ser Ile Lys Ser Thr Lys Met Leu Ile
    210                 215                 220

His Pro Thr Asp Ser Glu Ser Phe Glu
225                 230


<210> SEQ ID NO 23
<211> LENGTH: 233
<212> TYPE: PRT
<213> ORGANISM: Artificial Sequence
<220> FEATURE:
<223> OTHER INFORMATION: 228-460 S424T

<400> SEQUENCE: 23

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45
```

```
Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Lys Thr Lys Pro Glu Arg Arg Arg Gly Leu Ser Trp Lys
        195                 200                 205

Ser Gln Asn Gly Arg Leu Tyr Ser Ile Lys Ser Thr Lys Met Leu Ile
    210                 215                 220

His Pro Thr Asp Ser Glu Ser Phe Glu
225                 230
```

<210> SEQ ID NO 24
<211> LENGTH: 228
<212> TYPE: PRT
<213> ORGANISM: Artificial Sequence
<220> FEATURE:
<223> OTHER INFORMATION: 233-460 K423Q

<400> SEQUENCE: 24

```
Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
    50                  55                  60

Glu Thr Trp Glu Asn Tyr Lys Tyr Gly Phe Gly Arg Leu Asp Gly Glu
65                  70                  75                  80

Phe Trp Leu Gly Leu Glu Lys Ile Tyr Ser Ile Val Lys Gln Ser Asn
                85                  90                  95

Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
        115                 120                 125

His Leu Val Ala Ile Thr Gly Asn Val Pro Asn Ala Ile Pro Glu Asn
    130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp Trp His Asp Glu Cys
                165                 170                 175
```

Gly Glu Asn Asn Leu Asn Gly Lys Tyr Asn Lys Pro Arg Ala Gln Ser
180 185 190

Lys Pro Glu Arg Arg Arg Gly Leu Ser Trp Lys Ser Gln Asn Gly Arg
195 200 205

Leu Tyr Ser Ile Lys Ser Thr Lys Met Leu Ile His Pro Thr Asp Ser
210 215 220

Glu Ser Phe Glu
225

<210> SEQ ID NO 25
<211> LENGTH: 228
<212> TYPE: PRT
<213> ORGANISM: Artificial Sequence
<220> FEATURE:
<223> OTHER INFORMATION: 233-460 K423S

<400> SEQUENCE: 25

Glu Ile Arg Asn Val Lys His Asp Gly Ile Pro Ala Glu Cys Thr Thr
1 5 10 15

Ile Tyr Asn Arg Gly Glu His Thr Ser Gly Met Tyr Ala Ile Arg Pro
20 25 30

Ser Asn Ser Gln Val Phe His Val Tyr Cys Asp Val Ile Ser Gly Ser
35 40 45

Pro Trp Thr Leu Ile Gln His Arg Ile Asp Gly Ser Gln Asn Phe Asn
50 55 60

Glu Thr Trp Glu Asn Tyr Lys Tyr Gly Phe Gly Arg Leu Asp Gly Glu
65 70 75 80

Phe Trp Leu Gly Leu Glu Lys Ile Tyr Ser Ile Val Lys Gln Ser Asn
85 90 95

Tyr Val Leu Arg Ile Glu Leu Glu Asp Trp Lys Asp Asn Lys His Tyr
100 105 110

Ile Glu Tyr Ser Phe Tyr Leu Gly Asn His Glu Thr Asn Tyr Thr Leu
115 120 125

His Leu Val Ala Ile Thr Gly Asn Val Pro Asn Ala Ile Pro Glu Asn
130 135 140

Lys Asp Leu Val Phe Ser Thr Trp Asp His Lys Ala Lys Gly His Phe
145 150 155 160

Asn Cys Pro Glu Gly Tyr Ser Gly Gly Trp Trp Trp His Asp Glu Cys
165 170 175

Gly Glu Asn Asn Leu Asn Gly Lys Tyr Asn Lys Pro Arg Ala Ser Ser
180 185 190

Lys Pro Glu Arg Arg Arg Gly Leu Ser Trp Lys Ser Gln Asn Gly Arg
195 200 205

Leu Tyr Ser Ile Lys Ser Thr Lys Met Leu Ile His Pro Thr Asp Ser
210 215 220

Glu Ser Phe Glu
225

<210> SEQ ID NO 26
<211> LENGTH: 220
<212> TYPE: PRT
<213> ORGANISM: Artificial Sequence
<220> FEATURE:
<223> OTHER INFORMATION: 241-460 K423Q

<400> SEQUENCE: 26

Gly Ile Pro Ala Glu Cys Thr Thr Ile Tyr Asn Arg Gly Glu His Thr

```
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Gln Ser Lys Pro Glu Arg Arg Arg Gly Leu
            180                 185                 190

Ser Trp Lys Ser Gln Asn Gly Arg Leu Tyr Ser Ile Lys Ser Thr Lys
        195                 200                 205

Met Leu Ile His Pro Thr Asp Ser Glu Ser Phe Glu
    210                 215                 220


<210> SEQ ID NO 27
<211> LENGTH: 220
<212> TYPE: PRT
<213> ORGANISM: Artificial Sequence
<220> FEATURE:
<223> OTHER INFORMATION: 241-460 K423S

<400> SEQUENCE: 27

Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
```

```
145                 150                 155                 160

Gly Trp Trp Trp His Asp Glu Cys Gly Glu Asn Asn Leu Asn Gly Lys
                165                 170                 175

Tyr Asn Lys Pro Arg Ala Ser Ser Lys Pro Glu Arg Arg Arg Gly Leu
            180                 185                 190

Ser Trp Lys Ser Gln Asn Gly Arg Leu Tyr Ser Ile Lys Ser Thr Lys
        195                 200                 205

Met Leu Ile His Pro Thr Asp Ser Glu Ser Phe Glu
    210                 215                 220


<210> SEQ ID NO 28
<211> LENGTH: 219
<212> TYPE: PRT
<213> ORGANISM: Artificial Sequence
<220> FEATURE:
<223> OTHER INFORMATION: 242-460 K423Q

<400> SEQUENCE: 28

Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
            20                  25                  30

Cys Asp Val Ile Ser Gly Ser Pro Trp Thr Leu Ile Gln His Arg Ile
        35                  40                  45

Asp Gly Ser Gln Asn Phe Asn Glu Thr Trp Glu Asn Tyr Lys Tyr Gly
    50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95

Trp Lys Asp Asn Lys His Tyr Ile Glu Tyr Ser Phe Tyr Leu Gly Asn
            100                 105                 110

His Glu Thr Asn Tyr Thr Leu His Leu Val Ala Ile Thr Gly Asn Val
        115                 120                 125

Pro Asn Ala Ile Pro Glu Asn Lys Asp Leu Val Phe Ser Thr Trp Asp
    130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
                165                 170                 175

Asn Lys Pro Arg Ala Gln Ser Lys Pro Glu Arg Arg Arg Gly Leu Ser
            180                 185                 190

Trp Lys Ser Gln Asn Gly Arg Leu Tyr Ser Ile Lys Ser Thr Lys Met
        195                 200                 205

Leu Ile His Pro Thr Asp Ser Glu Ser Phe Glu
    210                 215


<210> SEQ ID NO 29
<211> LENGTH: 219
<212> TYPE: PRT
<213> ORGANISM: Artificial Sequence
<220> FEATURE:
<223> OTHER INFORMATION: 242-460 K423S

<400> SEQUENCE: 29

Ile Pro Ala Glu Cys Thr Thr Ile Tyr Asn Arg Gly Glu His Thr Ser
1               5                   10                  15
```

```
Gly Met Tyr Ala Ile Arg Pro Ser Asn Ser Gln Val Phe His Val Tyr
            20                  25                  30

Cys Asp Val Ile Ser Gly Ser Pro Trp Thr Leu Ile Gln His Arg Ile
        35                  40                  45

Asp Gly Ser Gln Asn Phe Asn Glu Thr Trp Glu Asn Tyr Lys Tyr Gly
    50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95

Trp Lys Asp Asn Lys His Tyr Ile Glu Tyr Ser Phe Tyr Leu Gly Asn
            100                 105                 110

His Glu Thr Asn Tyr Thr Leu His Leu Val Ala Ile Thr Gly Asn Val
        115                 120                 125

Pro Asn Ala Ile Pro Glu Asn Lys Asp Leu Val Phe Ser Thr Trp Asp
    130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
                165                 170                 175

Asn Lys Pro Arg Ala Ser Ser Lys Pro Glu Arg Arg Arg Gly Leu Ser
            180                 185                 190

Trp Lys Ser Gln Asn Gly Arg Leu Tyr Ser Ile Lys Ser Thr Lys Met
        195                 200                 205

Leu Ile His Pro Thr Asp Ser Glu Ser Phe Glu
    210                 215


<210> SEQ ID NO 30
<211> LENGTH: 231
<212> TYPE: PRT
<213> ORGANISM: Artificial Sequence
<220> FEATURE:
<223> OTHER INFORMATION: 225-455 K423Q

<400> SEQUENCE: 30

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
        115                 120                 125

Asn His Glu Thr Asn Tyr Thr Leu His Leu Val Ala Ile Thr Gly Asn
    130                 135                 140

Val Pro Asn Ala Ile Pro Glu Asn Lys Asp Leu Val Phe Ser Thr Trp
145                 150                 155                 160
```

-continued

```
Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Gln Ser Lys Pro Glu Arg Arg Arg Gly Leu
        195                 200                 205

Ser Trp Lys Ser Gln Asn Gly Arg Leu Tyr Ser Ile Lys Ser Thr Lys
    210                 215                 220

Met Leu Ile His Pro Thr Asp
225                 230


<210> SEQ ID NO 31
<211> LENGTH: 231
<212> TYPE: PRT
<213> ORGANISM: Artificial Sequence
<220> FEATURE:
<223> OTHER INFORMATION: 225-455 K423S

<400> SEQUENCE: 31

Thr Thr Pro Phe Leu Gln Leu Asn Glu Ile Arg Asn Val Lys His Asp
1               5                   10                  15

Gly Ile Pro Ala Glu Cys Thr Thr Ile Tyr Asn Arg Gly Glu His Thr
            20                  25                  30

Ser Gly Met Tyr Ala Ile Arg Pro Ser Asn Ser Gln Val Phe His Val
        35                  40                  45

Tyr Cys Asp Val Ile Ser Gly Ser Pro Trp Thr Leu Ile Gln His Arg
    50                  55                  60

Ile Asp Gly Ser Gln Asn Phe Asn Glu Thr Trp Glu Asn Tyr Lys Tyr
65                  70                  75                  80

Gly Phe Gly Arg Leu Asp Gly Glu Phe Trp Leu Gly Leu Glu Lys Ile
                85                  90                  95

Tyr Ser Ile Val Lys Gln Ser Asn Tyr Val Leu Arg Ile Glu Leu Glu
            100                 105                 110

Asp Trp Lys Asp Asn Lys His Tyr Ile Glu Tyr Ser Phe Tyr Leu Gly
        115                 120                 125

Asn His Glu Thr Asn Tyr Thr Leu His Leu Val Ala Ile Thr Gly Asn
    130                 135                 140

Val Pro Asn Ala Ile Pro Glu Asn Lys Asp Leu Val Phe Ser Thr Trp
145                 150                 155                 160

Asp His Lys Ala Lys Gly His Phe Asn Cys Pro Glu Gly Tyr Ser Gly
                165                 170                 175

Gly Trp Trp Trp His Asp Glu Cys Gly Glu Asn Asn Leu Asn Gly Lys
            180                 185                 190

Tyr Asn Lys Pro Arg Ala Ser Ser Lys Pro Glu Arg Arg Arg Gly Leu
        195                 200                 205

Ser Trp Lys Ser Gln Asn Gly Arg Leu Tyr Ser Ile Lys Ser Thr Lys
    210                 215                 220

Met Leu Ile His Pro Thr Asp
225                 230


<210> SEQ ID NO 32
<211> LENGTH: 230
<212> TYPE: PRT
<213> ORGANISM: Artificial Sequence
<220> FEATURE:
<223> OTHER INFORMATION: 226-455 K423Q

<400> SEQUENCE: 32
```

```
Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
            20                  25                  30

Gly Met Tyr Ala Ile Arg Pro Ser Asn Ser Gln Val Phe His Val Tyr
        35                  40                  45

Cys Asp Val Ile Ser Gly Ser Pro Trp Thr Leu Ile Gln His Arg Ile
    50                  55                  60

Asp Gly Ser Gln Asn Phe Asn Glu Thr Trp Glu Asn Tyr Lys Tyr Gly
65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
        115                 120                 125

His Glu Thr Asn Tyr Thr Leu His Leu Val Ala Ile Thr Gly Asn Val
    130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Gln Ser Lys Pro Glu Arg Arg Arg Gly Leu Ser
        195                 200                 205

Trp Lys Ser Gln Asn Gly Arg Leu Tyr Ser Ile Lys Ser Thr Lys Met
    210                 215                 220

Leu Ile His Pro Thr Asp
225                 230


<210> SEQ ID NO 33
<211> LENGTH: 230
<212> TYPE: PRT
<213> ORGANISM: Artificial Sequence
<220> FEATURE:
<223> OTHER INFORMATION: 226-455 K423S

<400> SEQUENCE: 33

Thr Pro Phe Leu Gln Leu Asn Glu Ile Arg Asn Val Lys His Asp Gly
1               5                   10                  15

Ile Pro Ala Glu Cys Thr Thr Ile Tyr Asn Arg Gly Glu His Thr Ser
            20                  25                  30

Gly Met Tyr Ala Ile Arg Pro Ser Asn Ser Gln Val Phe His Val Tyr
        35                  40                  45

Cys Asp Val Ile Ser Gly Ser Pro Trp Thr Leu Ile Gln His Arg Ile
    50                  55                  60

Asp Gly Ser Gln Asn Phe Asn Glu Thr Trp Glu Asn Tyr Lys Tyr Gly
65                  70                  75                  80

Phe Gly Arg Leu Asp Gly Glu Phe Trp Leu Gly Leu Glu Lys Ile Tyr
                85                  90                  95

Ser Ile Val Lys Gln Ser Asn Tyr Val Leu Arg Ile Glu Leu Glu Asp
            100                 105                 110

Trp Lys Asp Asn Lys His Tyr Ile Glu Tyr Ser Phe Tyr Leu Gly Asn
        115                 120                 125
```

```
His Glu Thr Asn Tyr Thr Leu His Leu Val Ala Ile Thr Gly Asn Val
    130                 135                 140

Pro Asn Ala Ile Pro Glu Asn Lys Asp Leu Val Phe Ser Thr Trp Asp
145                 150                 155                 160

His Lys Ala Lys Gly His Phe Asn Cys Pro Glu Gly Tyr Ser Gly Gly
                165                 170                 175

Trp Trp Trp His Asp Glu Cys Gly Glu Asn Asn Leu Asn Gly Lys Tyr
            180                 185                 190

Asn Lys Pro Arg Ala Ser Ser Lys Pro Glu Arg Arg Arg Gly Leu Ser
        195                 200                 205

Trp Lys Ser Gln Asn Gly Arg Leu Tyr Ser Ile Lys Ser Thr Lys Met
    210                 215                 220

Leu Ile His Pro Thr Asp
225                 230


<210> SEQ ID NO 34
<211> LENGTH: 228
<212> TYPE: PRT
<213> ORGANISM: Artificial Sequence
<220> FEATURE:
<223> OTHER INFORMATION: 228-455 K423Q

<400> SEQUENCE: 34

Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Gln Ser Lys Pro Glu Arg Arg Arg Gly Leu Ser Trp Lys
        195                 200                 205

Ser Gln Asn Gly Arg Leu Tyr Ser Ile Lys Ser Thr Lys Met Leu Ile
    210                 215                 220

His Pro Thr Asp
225


<210> SEQ ID NO 35
```

<211> LENGTH: 228
<212> TYPE: PRT
<213> ORGANISM: Artificial Sequence
<220> FEATURE:
<223> OTHER INFORMATION: 228-455 K423S

<400> SEQUENCE: 35

```
Phe Leu Gln Leu Asn Glu Ile Arg Asn Val Lys His Asp Gly Ile Pro
1               5                   10                  15

Ala Glu Cys Thr Thr Ile Tyr Asn Arg Gly Glu His Thr Ser Gly Met
            20                  25                  30

Tyr Ala Ile Arg Pro Ser Asn Ser Gln Val Phe His Val Tyr Cys Asp
        35                  40                  45

Val Ile Ser Gly Ser Pro Trp Thr Leu Ile Gln His Arg Ile Asp Gly
    50                  55                  60

Ser Gln Asn Phe Asn Glu Thr Trp Glu Asn Tyr Lys Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Val Leu Arg Ile Glu Leu Glu Asp Trp Lys
            100                 105                 110

Asp Asn Lys His Tyr Ile Glu Tyr Ser Phe Tyr Leu Gly Asn His Glu
        115                 120                 125

Thr Asn Tyr Thr Leu His Leu Val Ala Ile Thr Gly Asn Val Pro Asn
    130                 135                 140

Ala Ile Pro Glu Asn Lys Asp Leu Val Phe Ser Thr Trp Asp His Lys
145                 150                 155                 160

Ala Lys Gly His Phe Asn Cys Pro Glu Gly Tyr Ser Gly Gly Trp Trp
                165                 170                 175

Trp His Asp Glu Cys Gly Glu Asn Asn Leu Asn Gly Lys Tyr Asn Lys
            180                 185                 190

Pro Arg Ala Ser Ser Lys Pro Glu Arg Arg Arg Gly Leu Ser Trp Lys
        195                 200                 205

Ser Gln Asn Gly Arg Leu Tyr Ser Ile Lys Ser Thr Lys Met Leu Ile
    210                 215                 220

His Pro Thr Asp
225
```

<210> SEQ ID NO 36
<211> LENGTH: 223
<212> TYPE: PRT
<213> ORGANISM: Artificial Sequence
<220> FEATURE:
<223> OTHER INFORMATION: 233-455 K423Q

<400> SEQUENCE: 36

```
Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
    50                  55                  60

Glu Thr Trp Glu Asn Tyr Lys Tyr Gly Phe Gly Arg Leu Asp Gly Glu
65                  70                  75                  80

Phe Trp Leu Gly Leu Glu Lys Ile Tyr Ser Ile Val Lys Gln Ser Asn
```

```
                85                  90                  95

Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
        115                 120                 125

His Leu Val Ala Ile Thr Gly Asn Val Pro Asn Ala Ile Pro Glu Asn
    130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp Trp His Asp Glu Cys
                165                 170                 175

Gly Glu Asn Asn Leu Asn Gly Lys Tyr Asn Lys Pro Arg Ala Gln Ser
            180                 185                 190

Lys Pro Glu Arg Arg Arg Gly Leu Ser Trp Lys Ser Gln Asn Gly Arg
        195                 200                 205

Leu Tyr Ser Ile Lys Ser Thr Lys Met Leu Ile His Pro Thr Asp
    210                 215                 220


<210> SEQ ID NO 37
<211> LENGTH: 223
<212> TYPE: PRT
<213> ORGANISM: Artificial Sequence
<220> FEATURE:
<223> OTHER INFORMATION: 233-455 K423S

<400> SEQUENCE: 37

Glu Ile Arg Asn Val Lys His Asp Gly Ile Pro Ala Glu Cys Thr Thr
1               5                   10                  15

Ile Tyr Asn Arg Gly Glu His Thr Ser Gly Met Tyr Ala Ile Arg Pro
            20                  25                  30

Ser Asn Ser Gln Val Phe His Val Tyr Cys Asp Val Ile Ser Gly Ser
        35                  40                  45

Pro Trp Thr Leu Ile Gln His Arg Ile Asp Gly Ser Gln Asn Phe Asn
    50                  55                  60

Glu Thr Trp Glu Asn Tyr Lys Tyr Gly Phe Gly Arg Leu Asp Gly Glu
65                  70                  75                  80

Phe Trp Leu Gly Leu Glu Lys Ile Tyr Ser Ile Val Lys Gln Ser Asn
                85                  90                  95

Tyr Val Leu Arg Ile Glu Leu Glu Asp Trp Lys Asp Asn Lys His Tyr
            100                 105                 110

Ile Glu Tyr Ser Phe Tyr Leu Gly Asn His Glu Thr Asn Tyr Thr Leu
        115                 120                 125

His Leu Val Ala Ile Thr Gly Asn Val Pro Asn Ala Ile Pro Glu Asn
    130                 135                 140

Lys Asp Leu Val Phe Ser Thr Trp Asp His Lys Ala Lys Gly His Phe
145                 150                 155                 160

Asn Cys Pro Glu Gly Tyr Ser Gly Gly Trp Trp Trp His Asp Glu Cys
                165                 170                 175

Gly Glu Asn Asn Leu Asn Gly Lys Tyr Asn Lys Pro Arg Ala Ser Ser
            180                 185                 190

Lys Pro Glu Arg Arg Arg Gly Leu Ser Trp Lys Ser Gln Asn Gly Arg
        195                 200                 205

Leu Tyr Ser Ile Lys Ser Thr Lys Met Leu Ile His Pro Thr Asp
    210                 215                 220
```

<210> SEQ ID NO 38
<211> LENGTH: 215
<212> TYPE: PRT
<213> ORGANISM: Artificial Sequence
<220> FEATURE:
<223> OTHER INFORMATION: 241-455 K423Q

<400> SEQUENCE: 38

```
Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95

Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Gln Ser Lys Pro Glu Arg Arg Arg Gly Leu
            180                 185                 190

Ser Trp Lys Ser Gln Asn Gly Arg Leu Tyr Ser Ile Lys Ser Thr Lys
        195                 200                 205

Met Leu Ile His Pro Thr Asp
    210                 215
```

<210> SEQ ID NO 39
<211> LENGTH: 215
<212> TYPE: PRT
<213> ORGANISM: Artificial Sequence
<220> FEATURE:
<223> OTHER INFORMATION: 241-455 K423S

<400> SEQUENCE: 39

```
Gly Ile Pro Ala Glu Cys Thr Thr Ile Tyr Asn Arg Gly Glu His Thr
1               5                   10                  15

Ser Gly Met Tyr Ala Ile Arg Pro Ser Asn Ser Gln Val Phe His Val
            20                  25                  30

Tyr Cys Asp Val Ile Ser Gly Ser Pro Trp Thr Leu Ile Gln His Arg
        35                  40                  45

Ile Asp Gly Ser Gln Asn Phe Asn Glu Thr Trp Glu Asn Tyr Lys Tyr
    50                  55                  60

Gly Phe Gly Arg Leu Asp Gly Glu Phe Trp Leu Gly Leu Glu Lys Ile
65                  70                  75                  80

Tyr Ser Ile Val Lys Gln Ser Asn Tyr Val Leu Arg Ile Glu Leu Glu
                85                  90                  95
```

```
Asp Trp Lys Asp Asn Lys His Tyr Ile Glu Tyr Ser Phe Tyr Leu Gly
            100                 105                 110

Asn His Glu Thr Asn Tyr Thr Leu His Leu Val Ala Ile Thr Gly Asn
        115                 120                 125

Val Pro Asn Ala Ile Pro Glu Asn Lys Asp Leu Val Phe Ser Thr Trp
    130                 135                 140

Asp His Lys Ala Lys Gly His Phe Asn Cys Pro Glu Gly Tyr Ser Gly
145                 150                 155                 160

Gly Trp Trp Trp His Asp Glu Cys Gly Glu Asn Asn Leu Asn Gly Lys
                165                 170                 175

Tyr Asn Lys Pro Arg Ala Ser Ser Lys Pro Glu Arg Arg Arg Gly Leu
            180                 185                 190

Ser Trp Lys Ser Gln Asn Gly Arg Leu Tyr Ser Ile Lys Ser Thr Lys
        195                 200                 205

Met Leu Ile His Pro Thr Asp
    210                 215


<210> SEQ ID NO 40
<211> LENGTH: 214
<212> TYPE: PRT
<213> ORGANISM: Artificial Sequence
<220> FEATURE:
<223> OTHER INFORMATION: 242-455 K423Q

<400> SEQUENCE: 40

Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
            20                  25                  30

Cys Asp Val Ile Ser Gly Ser Pro Trp Thr Leu Ile Gln His Arg Ile
        35                  40                  45

Asp Gly Ser Gln Asn Phe Asn Glu Thr Trp Glu Asn Tyr Lys Tyr Gly
    50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95

Trp Lys Asp Asn Lys His Tyr Ile Glu Tyr Ser Phe Tyr Leu Gly Asn
            100                 105                 110

His Glu Thr Asn Tyr Thr Leu His Leu Val Ala Ile Thr Gly Asn Val
        115                 120                 125

Pro Asn Ala Ile Pro Glu Asn Lys Asp Leu Val Phe Ser Thr Trp Asp
    130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
                165                 170                 175

Asn Lys Pro Arg Ala Gln Ser Lys Pro Glu Arg Arg Arg Gly Leu Ser
            180                 185                 190

Trp Lys Ser Gln Asn Gly Arg Leu Tyr Ser Ile Lys Ser Thr Lys Met
        195                 200                 205

Leu Ile His Pro Thr Asp
    210


<210> SEQ ID NO 41
<211> LENGTH: 214
```

<212> TYPE: PRT
<213> ORGANISM: Artificial Sequence
<220> FEATURE:
<223> OTHER INFORMATION: 242-455 K423S

<400> SEQUENCE: 41

```
Ile Pro Ala Glu Cys Thr Thr Ile Tyr Asn Arg Gly Glu His Thr Ser
1               5                   10                  15

Gly Met Tyr Ala Ile Arg Pro Ser Asn Ser Gln Val Phe His Val Tyr
            20                  25                  30

Cys Asp Val Ile Ser Gly Ser Pro Trp Thr Leu Ile Gln His Arg Ile
        35                  40                  45

Asp Gly Ser Gln Asn Phe Asn Glu Thr Trp Glu Asn Tyr Lys Tyr Gly
    50                  55                  60

Phe Gly Arg Leu Asp Gly Glu Phe Trp Leu Gly Leu Glu Lys Ile Tyr
65                  70                  75                  80

Ser Ile Val Lys Gln Ser Asn Tyr Val Leu Arg Ile Glu Leu Glu Asp
                85                  90                  95

Trp Lys Asp Asn Lys His Tyr Ile Glu Tyr Ser Phe Tyr Leu Gly Asn
            100                 105                 110

His Glu Thr Asn Tyr Thr Leu His Leu Val Ala Ile Thr Gly Asn Val
        115                 120                 125

Pro Asn Ala Ile Pro Glu Asn Lys Asp Leu Val Phe Ser Thr Trp Asp
    130                 135                 140

His Lys Ala Lys Gly His Phe Asn Cys Pro Glu Gly Tyr Ser Gly Gly
145                 150                 155                 160

Trp Trp Trp His Asp Glu Cys Gly Glu Asn Asn Leu Asn Gly Lys Tyr
                165                 170                 175

Asn Lys Pro Arg Ala Ser Ser Lys Pro Glu Arg Arg Arg Gly Leu Ser
            180                 185                 190

Trp Lys Ser Gln Asn Gly Arg Leu Tyr Ser Ile Lys Ser Thr Lys Met
        195                 200                 205

Leu Ile His Pro Thr Asp
    210
```

<210> SEQ ID NO 42
<211> LENGTH: 233
<212> TYPE: PRT
<213> ORGANISM: Artificial Sequence
<220> FEATURE:
<223> OTHER INFORMATION: canine 227 K423Q

<400> SEQUENCE: 42

```
Phe Leu His Leu Asn Glu Thr Lys Asn Val Glu His Asn Asp Ile Pro
1               5                   10                  15

Ala Asn Cys Thr Thr Ile Tyr Asn Arg Gly Glu His Thr Ser Gly Ile
            20                  25                  30

Tyr Ser Ile Arg Pro Ser Asn Ser Gln Val Phe Asn Val Tyr Cys Asp
        35                  40                  45

Val Lys Ser Gly Ser Ser Trp Thr Leu Ile Gln His Arg Ile Asp Gly
    50                  55                  60

Ser Gln Asn Phe Asn Glu Thr Trp Glu Asn Tyr Arg Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Ile Leu Arg Ile Glu Leu Glu Asp Trp Asn
            100                 105                 110
```

```
Asp Asn Lys His Tyr Ile Glu Tyr Phe Phe His Leu Gly Asn His Glu
        115                 120                 125

Thr Asn Tyr Thr Leu His Leu Val Glu Ile Thr Gly Asn Ile Leu Asn
    130                 135                 140

Ala Leu Pro Glu His Lys Asp Leu Val Phe Ser Thr Trp Asp His Lys
145                 150                 155                 160

Ala Lys Gly His Val Asn Cys Pro Glu Ser Tyr Ser Gly Gly Trp Trp
                165                 170                 175

Trp His Asn Val Cys Gly Glu Asn Asn Leu Asn Gly Lys Tyr Asn Lys
            180                 185                 190

Gln Arg Ala Gln Thr Lys Pro Glu Arg Arg Arg Gly Leu Tyr Trp Lys
        195                 200                 205

Ser Gln Asn Gly Arg Leu Tyr Ser Ile Lys Ser Thr Lys Met Leu Ile
    210                 215                 220

His Pro Ile Asp Ser Glu Ser Ser Glu
225                 230


<210> SEQ ID NO 43
<211> LENGTH: 233
<212> TYPE: PRT
<213> ORGANISM: Artificial Sequence
<220> FEATURE:
<223> OTHER INFORMATION: canine 227 K423S

<400> SEQUENCE: 43

Phe Leu His Leu Asn Glu Thr Lys Asn Val Glu His Asn Asp Ile Pro
1               5                   10                  15

Ala Asn Cys Thr Thr Ile Tyr Asn Arg Gly Glu His Thr Ser Gly Ile
            20                  25                  30

Tyr Ser Ile Arg Pro Ser Asn Ser Gln Val Phe Asn Val Tyr Cys Asp
        35                  40                  45

Val Lys Ser Gly Ser Ser Trp Thr Leu Ile Gln His Arg Ile Asp Gly
    50                  55                  60

Ser Gln Asn Phe Asn Glu Thr Trp Glu Asn Tyr Arg Tyr Gly Phe Gly
65                  70                  75                  80

Arg Leu Asp Gly Glu Phe Trp Leu Gly Leu Glu Lys Ile Tyr Ser Ile
                85                  90                  95

Val Lys Gln Ser Asn Tyr Ile Leu Arg Ile Glu Leu Glu Asp Trp Asn
            100                 105                 110

Asp Asn Lys His Tyr Ile Glu Tyr Phe Phe His Leu Gly Asn His Glu
        115                 120                 125

Thr Asn Tyr Thr Leu His Leu Val Glu Ile Thr Gly Asn Ile Leu Asn
    130                 135                 140

Ala Leu Pro Glu His Lys Asp Leu Val Phe Ser Thr Trp Asp His Lys
145                 150                 155                 160

Ala Lys Gly His Val Asn Cys Pro Glu Ser Tyr Ser Gly Gly Trp Trp
                165                 170                 175

Trp His Asn Val Cys Gly Glu Asn Asn Leu Asn Gly Lys Tyr Asn Lys
            180                 185                 190

Gln Arg Ala Ser Thr Lys Pro Glu Arg Arg Arg Gly Leu Tyr Trp Lys
        195                 200                 205

Ser Gln Asn Gly Arg Leu Tyr Ser Ile Lys Ser Thr Lys Met Leu Ile
    210                 215                 220

His Pro Ile Asp Ser Glu Ser Ser Glu
225                 230
```

<210> SEQ ID NO 44
<211> LENGTH: 708
<212> TYPE: DNA
<213> ORGANISM: Artificial Sequence
<220> FEATURE:
<223> OTHER INFORMATION: nucleic acid encoding 225WT

<400> SEQUENCE: 44
actactccct ttcttcagtt gaatgaaata agaaatgtaa aacatgatgg cattcctgct 60
gaatgtacca ccatttataa cagaggtgaa catacaagtg gcatgtatgc catcagaccc 120
agcaactctc aagtttttca tgtctactgt gatgttatat caggtagtcc atggacatta 180
attcaacatc gaatagatgg atcacaaaac ttcaatgaaa cgtgggagaa ctacaaatat 240
ggttttggga ggcttgatgg agaattttgg ttgggcctag agaagatata ctccatagtg 300
aagcaatcta attatgtttt acgaattgag ttggaagact ggaaagacaa caaacattat 360
attgaatatt ctttttactt gggaaatcac gaaaccaact atacgctaca tctagttgcg 420
attactggca atgtccccaa tgcaatcccg gaaaacaaag atttggtgtt ttctacttgg 480
gatcacaaag caaaaggaca cttcaactgt ccagagggtt attcaggagg ctggtggtgg 540
catgatgagt gtggagaaaa caacctaaat ggtaaatata acaaaccaag agcaaaatct 600
aagccagaga ggagaagagg attatcttgg aagtctcaaa atggaaggtt atactctata 660
aaatcaacca aaatgttgat ccatccaaca gattcagaaa gctttgaa 708

<210> SEQ ID NO 45
<211> LENGTH: 708
<212> TYPE: DNA
<213> ORGANISM: Artificial Sequence
<220> FEATURE:
<223> OTHER INFORMATION: nucleic acid encoding 225 K423Q

<400> SEQUENCE: 45
actactccct ttcttcagtt gaatgaaata agaaatgtaa aacatgatgg cattcctgct 60
gaatgtacca ccatttataa cagaggtgaa catacaagtg gcatgtatgc catcagaccc 120
agcaactctc aagtttttca tgtctactgt gatgttatat caggtagtcc atggacatta 180
attcaacatc gaatagatgg atcacaaaac ttcaatgaaa cgtgggagaa ctacaaatat 240
ggttttggga ggcttgatgg agaattttgg ttgggcctag agaagatata ctccatagtg 300
aagcaatcta attatgtttt acgaattgag ttggaagact ggaaagacaa caaacattat 360
attgaatatt ctttttactt gggaaatcac gaaaccaact atacgctaca tctagttgcg 420
attactggca atgtccccaa tgcaatcccg gaaaacaaag atttggtgtt ttctacttgg 480
gatcacaaag caaaaggaca cttcaactgt ccagagggtt attcaggagg ctggtggtgg 540
catgatgagt gtggagaaaa caacctaaat ggtaaatata acaaaccaag agcacaatct 600
aagccagaga ggagaagagg attatcttgg aagtctcaaa atggaaggtt atactctata 660
aaatcaacca aaatgttgat ccatccaaca gattcagaaa gctttgaa 708

<210> SEQ ID NO 46
<211> LENGTH: 708
<212> TYPE: DNA
<213> ORGANISM: Artificial Sequence
<220> FEATURE:
<223> OTHER INFORMATION: nucleic acid encoding 225 K423S

<400> SEQUENCE: 46

-continued

```
actactccct ttcttcagtt gaatgaaata agaaatgtaa aacatgatgg cattcctgct     60

gaatgtacca ccatttataa cagaggtgaa catacaagtg gcatgtatgc catcagaccc    120

agcaactctc aagtttttca tgtctactgt gatgttatat caggtagtcc atggacatta    180

attcaacatc gaatagatgg atcacaaaac ttcaatgaaa cgtgggagaa ctacaaatat    240

ggttttggga ggcttgatgg agaattttgg ttgggcctag agaagatata ctccatagtg    300

aagcaatcta attatgtttt acgaattgag ttggaagact ggaaagacaa caaacattat    360

attgaatatt ctttttactt gggaaatcac gaaaccaact atacgctaca tctagttgcg    420

attactggca atgtccccaa tgcaatcccg gaaaacaaag atttggtgtt ttctacttgg    480

gatcacaaag caaaaggaca cttcaactgt ccagagggtt attcaggagg ctggtggtgg    540

catgatgagt gtggagaaaa caacctaaat ggtaaatata acaaaccaag agcaagctct    600

aagccagaga ggagaagagg attatcttgg aagtctcaaa atggaaggtt atactctata    660

aaatcaacca aaatgttgat ccatccaaca gattcagaaa gctttgaa                708
```

<210> SEQ ID NO 47
<211> LENGTH: 705
<212> TYPE: DNA
<213> ORGANISM: Artificial Sequence
<220> FEATURE:
<223> OTHER INFORMATION: nucleic acid encoding 226 K423Q

<400> SEQUENCE: 47

```
actccctttc ttcagttgaa tgaaataaga aatgtaaaac atgatggcat tcctgctgaa     60

tgtaccacca tttataacag aggtgaacat acaagtggca tgtatgccat cagacccagc    120

aactctcaag tttttcatgt ctactgtgat gttatatcag gtagtccatg gacattaatt    180

caacatcgaa tagatggatc acaaaacttc aatgaaacgt gggagaacta caaatatggt    240

tttgggaggc ttgatggaga attttggttg ggcctagaga agatatactc catagtgaag    300

caatctaatt atgttttacg aattgagttg gaagactgga aagacaacaa acattatatt    360

gaatattctt tttacttggg aaatcacgaa accaactata cgctacatct agttgcgatt    420

actggcaatg tccccaatgc aatcccggaa aacaaagatt tggtgttttc tacttgggat    480

cacaaagcaa aaggacactt caactgtcca gagggttatt caggaggctg gtggtggcat    540

gatgagtgtg gagaaaacaa cctaaatggt aaatataaca aaccaagagc acaatctaag    600

ccagagagga gaagaggatt atcttggaag tctcaaaatg gaaggttata ctctataaaa    660

tcaaccaaaa tgttgatcca tccaacagat tcagaaagct ttgaa                    705
```

<210> SEQ ID NO 48
<211> LENGTH: 705
<212> TYPE: DNA
<213> ORGANISM: Artificial Sequence
<220> FEATURE:
<223> OTHER INFORMATION: nucleic acid encoding 226 K423S

<400> SEQUENCE: 48

```
actccctttc ttcagttgaa tgaaataaga aatgtaaaac atgatggcat tcctgctgaa     60

tgtaccacca tttataacag aggtgaacat acaagtggca tgtatgccat cagacccagc    120

aactctcaag tttttcatgt ctactgtgat gttatatcag gtagtccatg gacattaatt    180

caacatcgaa tagatggatc acaaaacttc aatgaaacgt gggagaacta caaatatggt    240

tttgggaggc ttgatggaga attttggttg ggcctagaga agatatactc catagtgaag    300

caatctaatt atgttttacg aattgagttg gaagactgga aagacaacaa acattatatt    360
```

gaatattctt tttacttggg aaatcacgaa accaactata cgctacatct agttgcgatt 420
actggcaatg tccccaatgc aatcccggaa aacaaagatt tggtgttttc tacttgggat 480
cacaaagcaa aaggacactt caactgtcca gagggttatt caggaggctg gtggtggcat 540
gatgagtgtg gagaaaacaa cctaaatggt aaatataaca aaccaagagc aagctctaag 600
ccagagagga gaagaggatt atcttggaag tctcaaaatg gaaggttata ctctataaaa 660
tcaaccaaaa tgttgatcca tccaacagat tcagaaagct ttgaa 705

<210> SEQ ID NO 49
<211> LENGTH: 699
<212> TYPE: DNA
<213> ORGANISM: Artificial Sequence
<220> FEATURE:
<223> OTHER INFORMATION: nucleic acid encoding 228 K423Q

<400> SEQUENCE: 49
tttcttcagt tgaatgaaat aagaaatgta aaacatgatg gcattcctgc tgaatgtacc 60
accatttata acagaggtga acatacaagt ggcatgtatg ccatcagacc cagcaactct 120
caagtttttc atgtctactg tgatgttata tcaggtagtc catggacatt aattcaacat 180
cgaatagatg gatcacaaaa cttcaatgaa acgtgggaga actacaaata tggttttggg 240
aggcttgatg gagaattttg gttgggccta gagaagatat actccatagt gaagcaatct 300
aattatgttt tacgaattga gttggaagac tggaaagaca acaaacatta tattgaatat 360
tctttttact tgggaaatca cgaaaccaac tatacgctac atctagttgc gattactggc 420
aatgtcccca atgcaatccc ggaaaacaaa gatttggtgt tttctacttg ggatcacaaa 480
gcaaaaggac acttcaactg tccagagggt tattcaggag gctggtggtg gcatgatgag 540
tgtggagaaa acaacctaaa tggtaaatat aacaaaccaa gagcacaatc taagccagag 600
aggagaagag gattatcttg gaagtctcaa aatggaaggt tatactctat aaaatcaacc 660
aaaatgttga tccatccaac agattcagaa agctttgaa 699

<210> SEQ ID NO 50
<211> LENGTH: 699
<212> TYPE: DNA
<213> ORGANISM: Artificial Sequence
<220> FEATURE:
<223> OTHER INFORMATION: nucleic acid encoding 228 K423S

<400> SEQUENCE: 50
tttcttcagt tgaatgaaat aagaaatgta aaacatgatg gcattcctgc tgaatgtacc 60
accatttata acagaggtga acatacaagt ggcatgtatg ccatcagacc cagcaactct 120
caagtttttc atgtctactg tgatgttata tcaggtagtc catggacatt aattcaacat 180
cgaatagatg gatcacaaaa cttcaatgaa acgtgggaga actacaaata tggttttggg 240
aggcttgatg gagaattttg gttgggccta gagaagatat actccatagt gaagcaatct 300
aattatgttt tacgaattga gttggaagac tggaaagaca acaaacatta tattgaatat 360
tctttttact tgggaaatca cgaaaccaac tatacgctac atctagttgc gattactggc 420
aatgtcccca atgcaatccc ggaaaacaaa gatttggtgt tttctacttg ggatcacaaa 480
gcaaaaggac acttcaactg tccagagggt tattcaggag gctggtggtg gcatgatgag 540
tgtggagaaa acaacctaaa tggtaaatat aacaaaccaa gagcaagctc taagccagag 600
aggagaagag gattatcttg gaagtctcaa aatggaaggt tatactctat aaaatcaacc 660

-continued aaaatgttga tccatccaac agattcagaa agctttgaa 699

<210> SEQ ID NO 51
<211> LENGTH: 684
<212> TYPE: DNA
<213> ORGANISM: Artificial Sequence
<220> FEATURE:
<223> OTHER INFORMATION: nucleic acid encoding 233 K423Q

<400> SEQUENCE: 51
gaaataagaa atgtaaaaca tgatggcatt cctgctgaat gtaccaccat ttataacaga 60
ggtgaacata caagtggcat gtatgccatc agacccagca actctcaagt ttttcatgtc 120
tactgtgatg ttatatcagg tagtccatgg acattaattc aacatcgaat agatggatca 180
caaaacttca atgaaacgtg ggagaactac aaatatggtt ttgggaggct tgatggagaa 240
ttttggttgg gcctagagaa gatatactcc atagtgaagc aatctaatta tgttttacga 300
attgagttgg aagactggaa agacaacaaa cattatattg aatattcttt ttacttggga 360
aatcacgaaa ccaactatac gctacatcta gttgcgatta ctggcaatgt ccccaatgca 420
atcccggaaa acaaagattt ggtgttttct acttgggatc acaaagcaaa aggacacttc 480
aactgtccag agggttattc aggaggctgg tggtggcatg atgagtgtgg agaaaacaac 540
ctaaatggta aatataacaa accaagagca caatctaagc cagagaggag aagaggatta 600
tcttggaagt ctcaaaatgg aaggttatac tctataaaat caaccaaaat gttgatccat 660
ccaacagatt cagaaagctt tgaa 684

<210> SEQ ID NO 52
<211> LENGTH: 684
<212> TYPE: DNA
<213> ORGANISM: Artificial Sequence
<220> FEATURE:
<223> OTHER INFORMATION: nucleic acid encoding 233 K423S

<400> SEQUENCE: 52
gaaataagaa atgtaaaaca tgatggcatt cctgctgaat gtaccaccat ttataacaga 60
ggtgaacata caagtggcat gtatgccatc agacccagca actctcaagt ttttcatgtc 120
tactgtgatg ttatatcagg tagtccatgg acattaattc aacatcgaat agatggatca 180
caaaacttca atgaaacgtg ggagaactac aaatatggtt ttgggaggct tgatggagaa 240
ttttggttgg gcctagagaa gatatactcc atagtgaagc aatctaatta tgttttacga 300
attgagttgg aagactggaa agacaacaaa cattatattg aatattcttt ttacttggga 360
aatcacgaaa ccaactatac gctacatcta gttgcgatta ctggcaatgt ccccaatgca 420
atcccggaaa acaaagattt ggtgttttct acttgggatc acaaagcaaa aggacacttc 480
aactgtccag agggttattc aggaggctgg tggtggcatg atgagtgtgg agaaaacaac 540
ctaaatggta aatataacaa accaagagca agctctaagc cagagaggag aagaggatta 600
tcttggaagt ctcaaaatgg aaggttatac tctataaaat caaccaaaat gttgatccat 660
ccaacagatt cagaaagctt tgaa 684

<210> SEQ ID NO 53
<211> LENGTH: 660
<212> TYPE: DNA
<213> ORGANISM: Artificial Sequence
<220> FEATURE:
<223> OTHER INFORMATION: nucleic acid encoding 241 K423Q

<400> SEQUENCE: 53

```
ggcattcctg ctgaatgtac caccatttat aacagaggtg aacatacaag tggcatgtat     60

gccatcagac ccagcaactc tcaagttttt catgtctact gtgatgttat atcaggtagt    120

ccatggacat taattcaaca tcgaatagat ggatcacaaa acttcaatga aacgtgggag    180

aactacaaat atggttttgg gaggcttgat ggagaatttt ggttgggcct agagaagata    240

tactccatag tgaagcaatc taattatgtt ttacgaattg agttggaaga ctggaaagac    300

aacaaacatt atattgaata ttctttttac ttgggaaatc acgaaaccaa ctatacgcta    360

catctagttg cgattactgg caatgtcccc aatgcaatcc cggaaaacaa agatttggtg    420

ttttctactt gggatcacaa agcaaaagga cacttcaact gtccagaggg ttattcagga    480

ggctggtggt ggcatgatga gtgtggagaa aacaacctaa atggtaaata taacaaacca    540

agagcacaat ctaagccaga gaggagaaga ggattatctt ggaagtctca aaatggaagg    600

ttatactcta taaaatcaac caaaatgttg atccatccaa cagattcaga aagctttgaa    660
```

<210> SEQ ID NO 54
<211> LENGTH: 660
<212> TYPE: DNA
<213> ORGANISM: Artificial Sequence
<220> FEATURE:
<223> OTHER INFORMATION: nucleic acid encoding 241 K423S

<400> SEQUENCE: 54

```
ggcattcctg ctgaatgtac caccatttat aacagaggtg aacatacaag tggcatgtat     60

gccatcagac ccagcaactc tcaagttttt catgtctact gtgatgttat atcaggtagt    120

ccatggacat taattcaaca tcgaatagat ggatcacaaa acttcaatga aacgtgggag    180

aactacaaat atggttttgg gaggcttgat ggagaatttt ggttgggcct agagaagata    240

tactccatag tgaagcaatc taattatgtt ttacgaattg agttggaaga ctggaaagac    300

aacaaacatt atattgaata ttctttttac ttgggaaatc acgaaaccaa ctatacgcta    360

catctagttg cgattactgg caatgtcccc aatgcaatcc cggaaaacaa agatttggtg    420

ttttctactt gggatcacaa agcaaaagga cacttcaact gtccagaggg ttattcagga    480

ggctggtggt ggcatgatga gtgtggagaa aacaacctaa atggtaaata taacaaacca    540

agagcaagct ctaagccaga gaggagaaga ggattatctt ggaagtctca aaatggaagg    600

ttatactcta taaaatcaac caaaatgttg atccatccaa cagattcaga aagctttgaa    660
```

<210> SEQ ID NO 55
<211> LENGTH: 657
<212> TYPE: DNA
<213> ORGANISM: Artificial Sequence
<220> FEATURE:
<223> OTHER INFORMATION: nucleic acid encoding 242 K423Q

<400> SEQUENCE: 55

```
attcctgctg aatgtaccac catttataac agaggtgaac atacaagtgg catgtatgcc     60

atcagaccca gcaactctca agtttttcat gtctactgtg atgttatatc aggtagtcca    120

tggacattaa ttcaacatcg aatagatgga tcacaaaact tcaatgaaac gtgggagaac    180

tacaaatatg gttttgggag gcttgatgga gaattttggt tgggcctaga gaagatatac    240

tccatagtga agcaatctaa ttatgtttta cgaattgagt tggaagactg gaaagacaac    300

aaacattata ttgaatattc tttttacttg ggaaatcacg aaaccaacta tacgctacat    360

ctagttgcga ttactggcaa tgtccccaat gcaatcccgg aaaacaaaga tttggtgttt    420
```

-continued

```
tctacttggg atcacaaagc aaaaggacac ttcaactgtc cagagggtta ttcaggaggc    480

tggtggtggc atgatgagtg tggagaaaac aacctaaatg gtaaatataa caaaccaaga    540

gcacaatcta agccagagag gagaagagga ttatcttgga agtctcaaaa tggaaggtta    600

tactctataa aatcaaccaa aatgttgatc catccaacag attcagaaag ctttgaa       657


<210> SEQ ID NO 56
<211> LENGTH: 657
<212> TYPE: DNA
<213> ORGANISM: Artificial Sequence
<220> FEATURE:
<223> OTHER INFORMATION: nucleic acid encoding 242 K423S

<400> SEQUENCE: 56

attcctgctg aatgtaccac catttataac agaggtgaac atacaagtgg catgtatgcc     60

atcagaccca gcaactctca agtttttcat gtctactgtg atgttatatc aggtagtcca    120

tggacattaa ttcaacatcg aatagatgga tcacaaaact tcaatgaaac gtgggagaac    180

tacaaatatg gttttgggag gcttgatgga gaattttggt tgggcctaga gaagatatac    240

tccatagtga agcaatctaa ttatgtttta cgaattgagt tggaagactg gaaagacaac    300

aaacattata ttgaatattc tttttacttg ggaaatcacg aaaccaacta tacgctacat    360

ctagttgcga ttactggcaa tgtccccaat gcaatcccgg aaaacaaaga tttggtgttt    420

tctacttggg atcacaaagc aaaaggacac ttcaactgtc cagagggtta ttcaggaggc    480

tggtggtggc atgatgagtg tggagaaaac aacctaaatg gtaaatataa caaaccaaga    540

gcaagctcta agccagagag gagaagagga ttatcttgga agtctcaaaa tggaaggtta    600

tactctataa aatcaaccaa aatgttgatc catccaacag attcagaaag ctttgaa       657


<210> SEQ ID NO 57
<211> LENGTH: 699
<212> TYPE: DNA
<213> ORGANISM: Artificial Sequence
<220> FEATURE:
<223> OTHER INFORMATION: nucleic acid encoding canine 227 K423Q

<400> SEQUENCE: 57

tttttgcatc tcaacgaaac gaagaatgtc gaacacaacg acattccggc aaattgcaca     60

actatctaca atagaggcga acatacgtcc ggtatctact ccattagacc ttcaaacagc    120

caggtattca atgtgtactg cgatgtaaag tcaggatcgt catggacact gatccagcat    180

aggatcgacg ggtcccagaa cttcaacgag acatgggaga actaccgcta tggatttgga    240

aggctggatg gggagttctg gttgggactt gagaaaatct acagcattgt gaagcagtcg    300

aactacattc tccggattga actggaggac tggaatgaca acaaacacta catcgagtat    360

ttctttcatc tcggcaacca tgaaacgaat tacaccttgc accttgtgga aatcacgggc    420

aacattttga acgcgctgcc agaacacaaa gacctggtgt tttcgacatg ggatcacaaa    480

gcaaaggggc acgtgaactg tcccgaatca tatagcgggg gatggtggtg gcacaatgtc    540

tgtggtgaga acaatctcaa cgggaaatac aataagcagc gagctcagac gaaacccgag    600

cggcggagag gtctgtattg gaagtcgcag aatggacgcc tgtattcgat caaatcgacg    660

aaaatgctca tccaccccat cgactccgaa tcgtcggag                           699
```

PEPTIDES AND COMPOSITIONS FOR TREATMENT OF JOINT DAMAGE

RELATED APPLICATIONS

This application is a divisional application of U.S. patent application Ser. No. 14/201,694 filed on Mar. 7, 2014, now U.S. Pat. No. 9,301,971, which claims priority to and the benefit under 35 USC 119(e) to U.S. Provisional Patent Application No. 61/775,400, filed on Mar. 8, 2013, both of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Mar. 7, 2014, is named PAT055625_US_NP_sequence_listing_ST25.txt and is 155,980 bytes in size.

BACKGROUND OF THE INVENTION

Osteoarthritis (OA) represents the most common musculoskeletal disorder. Approximately 40 million Americans are currently affected; a number predicted to increase to 60 million within the next twenty years as a result of aging population and an increase in life expectancy, making it the fourth leading cause of disability. OA is characterized by a slow degenerative breakdown of a joint including both articular cartilage (containing the cells and matrix which produce lubrication and cushioning for the joint) and subchondral bone underlying the articular cartilage. OA can be considered a consequence of various etiologic factors. For example, it can be caused by abnormal biomechanical stress or genetic or acquired abnormalities of articular cartilage or bone. Current OA therapies include pain relief with oral NSAIDs or selective cyclooxygenase 2 (COX-2) inhibitors, intra-articular (IA) injection with agents such as corticosteroids and hyaluronan, and surgical approaches.

Joint damage, e.g., acute joint injury, such as a meniscal or ligament tear, or an intra-articular fracture can also lead to arthritis, e.g., posttraumatic arthritis. Because articular cartilage has a limited ability to repair, even small undetectable damage can often get worse over time and lead to OA. Current treatments for joint injury can include surgery and other invasive procedures focused on regeneration of damaged joints as well as treatment with agents to reduce pain and inflammation.

Mesenchymal stem cells (MSCs) are present in adult articular cartilage and upon isolation can be programmed in vitro to undergo differentiation to chondrocytes and other mesenchymal cell lineages, and may be used for cartilage regeneration. In part, the process is regulated by growth factors (TGFβs, BMPs), serum conditions and cell-cell contact. WO2011/008773 describes peptide compositions and use of those compositions for treating or preventing arthritis and joint injury and for inducing differentiation of mesenchymal cells into chondrocytes. Additionally, WO2012/129562 describes small molecule compounds, compositions and use of those compositions for amelioration of arthritis and joint injury and for inducing differentiation of mesenchymal cells into chondrocytes.

Though surgical techniques, and regenerative technology have made some progress in restoration of cartilage, slowing degeneration, and improved repair of joint damage, a continued need exists for improvement of compositions and methods for effective cartilage regeneration, treatment of joint damage and amelioration or prevention of OA.

BRIEF SUMMARY OF THE INVENTION

The present invention relates to the identification of new polypeptide and protein variants of angiopoietin-like 3 (ANGPTL3) that have improved pharmaceutical properties, e.g., are more stable, less susceptible to proteolysis and enzymatic degradation than wild-type ANGPTL3. Also provided are pharmaceutical compositions and methods for treatment of joint damage or joint injury, and methods of ameliorating or preventing arthritis, joint damage or joint injury in a mammal.

Thus, provided are protease-resistant polypeptides comprising an amino acid sequence that has at least 95% amino acid sequence identity, or at least 96%, 97%, 98%, 99% or 100% amino acid sequence identity to an amino acid sequence selected from any one or more of the sequences of TABLE 1, and as further described herein. The modified polypeptides of TABLE 1 include an amino acid that is a polar amino acid other than K or R at position 423, as determined with reference to the full length ANGPTL3 polypeptide sequence, SEQ ID NO:1. In some embodiments the amino acid at position 423 as determined with reference to SEQ ID NO:1 is Q or S. In certain embodiments the amino acid at position 423 as determined with reference to SEQ ID NO:1 is Q. In certain embodiments the amino acid at position 423 as determined with reference to SEQ ID NO:1 is S. In addition, provided polypeptides have chondrogenic activity.

In some embodiments, the polypeptide comprises a sequence having at least 95% identity or at least 96%, 97%, 98%, 99% or 100% to any one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, and SEQ ID NO:41. In some embodiments the polypeptide comprises a sequence having at least 95% identity or at least 96%, 97%, 98%, 99% or 100% to any one of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29. In some embodiments, the polypeptide comprises any one of the sequences of TABLE 1. In some embodiments, the polypeptide comprises any one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, and SEQ ID NO:41. In some embodiments the polypeptide comprises any one of SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, and SEQ ID NO:29. In some embodiments, the polypeptide is any one of the sequences of TABLE 1. In some embodiments, the polypeptide is any one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, and SEQ ID NO:41. In some embodiments the polypeptide is any one of SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, and SEQ ID NO:29.

Polypeptides of the invention may incorporate one or more chemical modifications (e.g., PEGylation). In some embodiments, polypeptides of the invention may comprise a heterologous peptide as a fusion protein, which may optionally be fused at the amino-terminal or the carboxy-terminal end of the polypeptide. Also provided are polynucleotides encoding the polypeptides of the invention; vectors containing polynucleotides encoding the polypeptides; and host cells comprising such vectors.

The present invention also provides pharmaceutical compositions comprising the polypeptides of the invention and a pharmaceutically acceptable carrier. Such compositions can be used in methods provided herein for treating, ameliorating or preventing arthritis or joint damage in a patient, where the method comprises administering to a joint of a patient a therapeutically effective amount of a pharmaceutical composition of the invention. Examples of conditions that can benefit from such methods include, but are not limited to arthritis (e.g., osteoarthritis, traumatic arthritis), and joint damage (e.g., acute joint injury).

The present invention further provides methods of treating a subject comprising administering a therapeutically effectively amount of a polypeptide of the invention. Provided methods include treating a subject having or at risk of having joint damage and/or arthritis, comprising administering to the subject a therapeutically effective amount of one or more polypeptides of the invention or a pharmaceutical composition thereof. Still further provided are methods of inducing differentiation of mesenchymal stem cells into chondrocytes, comprising contacting mesenchymal stem cells with an effective amount of a polypeptide of the invention to induce differentiation of the mesenchymal stem cells into chondrocytes.

These and other aspects of the invention, including additional features, advantages, and embodiments of the invention, will be described and elucidated in further detail in the following detailed description and appended claims of the invention.

BRIEF DESCRIPTION OF THE DRAWINGS

FIG. 9 depicts results in a rat meniscal tear model of joint damage following treatment with ANGPTL3 construct.

DETAILED DESCRIPTION

Figure 1:
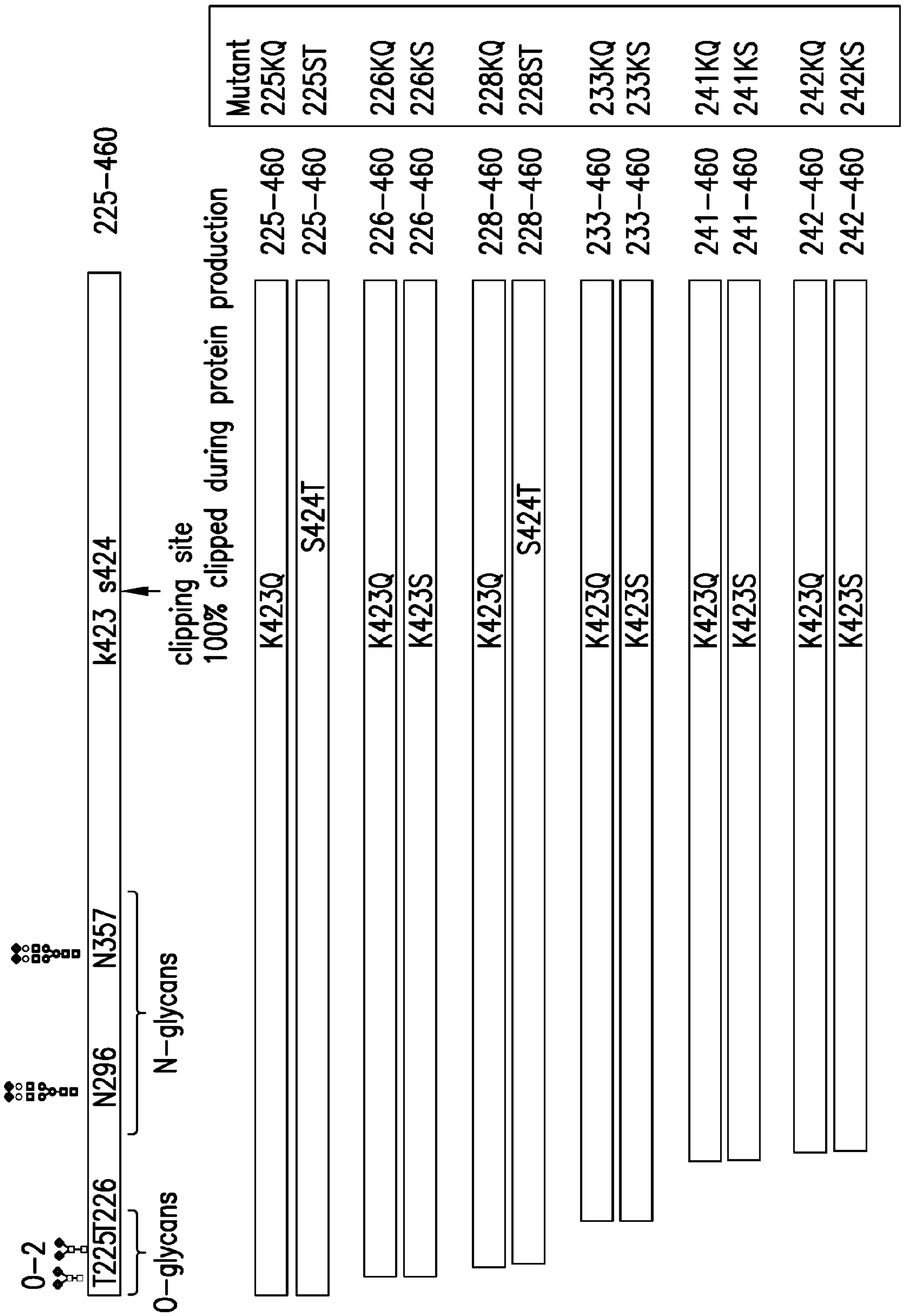
FIG. 1 depicts a schematic of hANGPTL3 proteins engineered to improve protein stability and enhance proteolytic resistance. During protein production of wild type protein and peptide sequences, 100% cleavage was observed between Lys423 and Ser424. To mitigate proteolysis, various mutant peptides were generated wherein Lys 423 was mutated to Gln or Ser or Ser424 was mutated to Thr.

The present invention is based, at least in part, on the identification of Angiopoietin-like 3 (ANGPTL3) polypeptides that stimulate chondrocyte differentiation of mesenchymal stem cells and that are resistant to cleavage by proteases (e.g., trypsin-like proteases). WO2011/008773, describes ANGPTL3 peptide compositions and use of peptide compositions for treating or preventing arthritis and joint injury and for inducing differentiation of mesenchymal cells into chondrocytes. We found that wild type ANGPTL3 proteins are subject to protease clipping and instability and have identified sequence variants to mitigate this effect. The present invention thus provides improved peptide compositions for repairing cartilage. In particular, provided are ANGPTL3 peptides modified in accordance with the present invention to have increased protease-resistance as compared to a wildtype ANGPTL3 polypeptide. Also provided are compositions and methods for administration of ANGPTL3 polypeptides to prevent or ameliorate arthritis or joint injury by administering a polypeptide of the invention into a joint, a cartilage tissue or a cartilage proximal tissue, or systemically. Further, the invention provides compositions and methods for induction of mesenchymal stem cell differentiation into chondrocytes.

I. Definitions

The term “protease-resistant” as used herein refers to a polypeptide comprising a modification that renders the polypeptide less susceptible to cleavage by a trypsin-like protease than a corresponding non-modified wildtype polypeptide. In specific embodiments a protease-resistant polypeptide is an ANGPTL3 polypeptide that has an amino acid substitution, relative to a native wildtype peptide sequence, at an R or a K residue.

“ANGPTL3” refers to a member of the angoipoietin protein family. An amino acid sequence of ANGPTL3 (GenBank Accession No. NP 055310.1) is set forth in SEQ ID NO:1; and the corresponding polynucleotide sequence of which is set forth as SEQ ID NO: 2 (NCBI reference sequence number NM014495.2, wherein the ANGPTL3 coding sequence comprises nt 52-1434 of SEQ ID NO:2). “ANGPTL3 polypeptide” refers to a naturally occurring expressed polypeptide. For the purposes of the present disclosure, the numbering of an amino acid is typically determined with reference to the full-length wildtype human ANGPTL3 polypeptide sequence (SEQ ID NO:1). Thus, in embodiments in which a polypeptide of the invention contains only a C-terminal portion of full-length ANGPTL3, but not the N-terminal portion, although the peptide is less than 460 amino acids in length, the numbering of the positions is based on SEQ ID NO:1. For example, reference to position 423 of an ANGPTL3 polypeptide of the invention refers to position 423 of SEQ ID NO:1, even though the ANGPTL3 polypeptide of the invention itself may only be 200 amino acids in length. In determining an amino acid in a sequence of interest that “corresponds to” a position in a reference sequence, such as SEQ ID NO:1, this is performed by optimally aligning the sequences, e.g., using the default CLUSTAL alignment parameters or default BLAST 2 alignment parameters and comparing the sequences. For example, position 423 in a sequence of interest that is “determined with reference to SEQ ID NO:1”, or an amino acid that “corresponds to” position 423 of SEQ ID NO:1, means the amino acid that aligns with position 423 of SEQ ID NO:1 when the sequence of interest is optimally aligned with SEQ ID NO:1.

The terms “peptidomimetic” and “mimetic” refer to a synthetic chemical compound that has substantially the same functional characteristics of a naturally or non-naturally occurring polypeptide (e.g., ANGPTL3), but different (though typically similar) structural characteristics. Peptide analogs are commonly used in the field as non-peptide active compounds (e.g., drugs) with properties analogous to those of a template peptide. Such non-peptide compounds are termed “peptide mimetics” or “peptidomimetics” (Fauchere, *J. Adv. Drug Res.* 15:29 (1986); Veber and Freidinger *TINS* p. 392 (1985); and Evans et al. *J. Med. Chem.* 30:1229 (1987)). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as found in a polypeptide of interest, but have one or more peptide linkages optionally replaced by a linkage selected from the group consisting of, e.g., $—CH_2NH—$, $—CH_2S—$, $—CH_2—CH_2—$, —CH=CH— (cis and trans), $—COCH_2—$, $—CH(OH)CH_2—$, and $—CH_2SO—$. A mimetic can be either entirely composed of synthetic, non-natural analogues of amino acids, or, is a chimeric molecule of partly natural peptide amino acids and partly non-natural analogs of amino acids. A mimetic can also incorporate any amount of natural amino acid conservative substitutions as long as such substitutions also do not substantially alter the mimetic’s structure and/or activity. For example, a mimetic composition is within the scope of the invention if it is capable of chondrogenic activity of an ANGPTL3 polypeptide.

The terms “polypeptide,” “peptide” and “protein” are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Polypeptides, peptides, and proteins of the invention comprise protease resistant ANGPTL3 peptidomimetics having chondrogenic activity.

The term “amino acid” refers to naturally occurring and synthetic amino acids, as well as amino acid analogs and amino acid mimetics that function in a manner similar to naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) as well as pyrrolysine, pyrroline-carboxy-lysine, and selenocysteine.

“Conservatively modified variants” applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are “silent variations,” which are one species of conservatively modified variations. Every polypeptide sequence herein which is encoded by a polynucleotide encompasses every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

One of skill will recognize that individual substitutions, deletions or additions to a nucleic acid, peptide, polypeptide, or protein sequence which alters, adds or deletes a single amino acid or a small percentage of amino acids with reference to an original encoded amino acid sequence results in a "conservatively modified variant" where the alteration produces substitution of an amino acid with a chemically similar amino acid and/or a polypeptide sequence that produces a structurally similar protein having similar functional activity to the original protein. Conservative substitution tables providing functionally similar amino acids are well known in the art. Such conservatively modified variants are in addition to and do not exclude polymorphic variants, interspecies homologs, and alleles of the invention.

The term "conservative amino acid substitutions" refers to the substitution (conceptually or otherwise) of an amino acid from one such group with a different amino acid from the same group. One example of substitutions is based on analyzing the normalized frequencies of amino acid changes between corresponding proteins of homologous organisms (see, e.g., Schulz, G. E. and R. H. Schirmer, Principles of Protein Structure, Springer-Verlag). According to such analyses, groups of amino acids may be defined where amino acids within a group exchange preferentially with each other and, therefore, resemble each other most in their impact on the overall protein structure (see, e.g., Schulz, G. E. and R. H. Schirmer, Principles of Protein Structure, Springer-Verlag). One example of a set of amino acid groups defined in this manner include: (i) a charged group, consisting of Glu and Asp, Lys, Arg and His; (ii) a positively-charged group, consisting of Lys, Arg and His; (iii) a negatively-charged group, consisting of Glu and Asp; (iv) an aromatic group, consisting of Phe, Tyr and Trp; (v) a nitrogen ring group, consisting of His and Trp; (vi) a large aliphatic nonpolar group, consisting of Val, Leu and Ile; (vii) a slightly-polar group, consisting of Met and Cys; (viii) a small-residue group, consisting of Ser, Thr, Asp, Asn, Gly, Ala, Glu, Gln and Pro; (ix) an aliphatic group consisting of Val, Leu, Ile, Met and Cys; and (x) a small hydroxyl group consisting of Ser and Thr. Other examples of conservative substitutions based on shared physical properties are the substitutions within the following groups: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

"Percentage of sequence identity" is determined by comparing two optimally aligned sequences over a comparison window, wherein the portion of the amino acid sequence or polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 95% identity, optionally 96%, 97%, 98%, or 99% identity over a specified region, or, when not specified, over the entire sequence), when compared and aligned for maximum correspondence over a comparison window, or designated region as measured using one of the following sequence comparison algorithms or by manual alignment and visual inspection. The invention provides polypeptides that are substantially identical to the polypeptides, respectively, exemplified herein (e.g., any of SEQ ID NOs: 11-42), as well as uses thereof including but not limited to use for treating or preventing arthritis or joint injury. Optionally, for nucleic acids, the identity exists over a region that is at least about 150 nucleotides in length, or more preferably over a region that is 300 to 450 or 600 or more nucleotides in length, or the entire length of the reference sequence. For amino acid sequence, optionally, identity exists over a region that is at least about 50 amino acids in length, or more preferably over a region that is 100 to 150 or 200 or more amino acids in length, or the entire length of the reference sequence.

For sequence comparison, typically one sequence acts as a reference sequence to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 50 to 600, usually about 75 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0)

and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "isolated," when applied to a nucleic acid or protein, denotes that the nucleic acid or protein is purified to be essentially free of other cellular components with which it is associated in the natural state. It is often in a homogeneous or nearly homogeneous state. It can be in either a dry or aqueous solution. Purity and homogeneity may be determined using analytical chemistry techniques known and used typically in the art, e.g., polyacrylamide gel electrophoresis, high performance liquid chromatography, etc. A protein that is the predominant species present in a preparation is substantially purified. The term "purified" in some embodiments denotes that a protein gives rise to essentially one band in an electrophoretic gel. Typically, it means that a protein is at least 85% pure, more preferably at least 95% pure, and most preferably at least 99% pure.

The term "hyaluronic acid" are used herein to include derivatives of hyaluronic acid that include esters of hyaluronic acid, salts of hyaluronic acid and also includes the term hyaluronan. The designation also includes both low and high molecular weight forms of hyaluronans and cross-linked hyaluronans or hylans. Examples of such hyaluronans are Synvisc™ (Genzyme Corp. Cambridge, Mass.), ORTHOVISC™ (Anika Therapeutics, Woburn, Mass.), HYALGAN™ (Sanofi-Synthelabo Inc., Malvern, Pa.), and ProVisc (Alcon/Novartis).

As used in this specification and the appended claims, the singular forms "a," "an," and "the" include plural referents unless the context clearly dictates otherwise.

II. Angiopoietin-like 3 protease-resistant polypeptides

Angiopoietin-like 3 is a member of the angiopoietin-like family of secreted factors. It is predominantly expressed in the liver, and has the characteristic structure of angiopoietins, consisting of a signal peptide, N-terminal coiled-coil domain (CCD) and the C-terminal fibrinogen (FBN)-like domain. Angiopoietin-like 3 was shown to bind $\alpha V/\beta 3$ integrins and FBN-like domain alone was sufficient to induce endothelial cell adhesion and in vivo angiogenesis (Camenisch et al., *J. Biol. Chem.* 277: 17281-17290, 2002). Endogenous ANGPTL3 is generally cleaved in vivo into amino-terminal and carboxy-terminal fragments. As summarized above and further described herein, the present invention contemplates use of various protease-resistant ANGPTL3 proteins having chondrogenic activity.

In some embodiments, an isolated polypeptide comprises an amino acid sequence that has at least 95% identity, or at least 96%, 97%, 98%, or 99% identity, to an amino acid sequence selected from any one of the sequences of TABLE 1, wherein the polypeptide comprises an amino acid that is a polar amino acid other than K or R at position 423, as determined with reference to SEQ ID NO:1. The polypeptides of the invention have chondrogenic activity. In some embodiments, a polypeptide comprises the amino acid sequence that has at least 95% identity, or at least or at least 96%, 97%, 98%, or 99% identity, to an amino acid sequence selected from any one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41 wherein the polypeptide comprises an amino acid that is a polar amino acid other than K or R at position 423, as determined with reference to SEQ ID NO:1, and the polypeptide has chondrogenic activity. In a further embodiment, a polypeptide comprises the amino acid sequence that has at least 95% identity, or at least or at least 96%, 97%, 98%, or 99% identity, to an amino acid sequence selected from any one of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29 wherein the polypeptide comprises an amino acid that is a polar amino acid other than K or R at position 423, as determined with reference to SEQ ID NO:1, and the polypeptide has chondrogenic activity.

In some embodiments, an isolated polypeptide comprises an amino acid sequence selected from any one of the sequences of TABLE 1, wherein the polypeptide comprises an amino acid that is a polar amino acid other than K or R at position 423, as determined with reference to SEQ ID NO:1, and the polypeptide has chondrogenic activity. In some embodiments, a polypeptide comprises an amino acid sequence selected from any one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41 wherein the polypeptide comprises an amino acid that is a polar amino acid other than K or R at position 423, as determined with reference to SEQ ID NO:1, and the polypeptide has chondrogenic activity. In a further embodiment, a polypeptide comprises an amino acid sequence selected from any one of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29 wherein the polypeptide comprises an amino acid that is a polar amino acid other than K or R at position 423, as determined with reference to SEQ ID NO:1, and the polypeptide has chondrogenic activity.

In some embodiments, an isolated polypeptide has at least 95% identity, or at least 96%, 97%, 98%, or 99% identity, to an amino acid sequence selected from any one of the sequences of TABLE 1, wherein the polypeptide comprises an amino acid that is a polar amino acid other than K or R at position 423, as determined with reference to SEQ ID NO:1, and the polypeptide has chondrogenic activity. In some embodiments, a polypeptide has at least 95% identity, or at least or at least 96%, 97%, 98%, or 99% identity, to an amino acid sequence selected from any one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41 wherein the polypeptide comprises an amino acid that is a polar amino acid other than K or R at position 423, as determined with reference to SEQ ID NO:1, and the polypeptide has chondrogenic activity. In a further embodiment, a polypeptide has at least 95% identity, or at least or at least 96%, 97%, 98%, or 99% identity, to an amino acid sequence selected from any one of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29 wherein the polypeptide comprises an amino acid that is a polar amino acid other than K or R at position 423, as determined with reference to SEQ ID NO:1, and the polypeptide has chondrogenic activity.

In some embodiments, an isolated polypeptide is an amino acid sequence selected from any one of the sequences of TABLE 1. In some embodiments, a polypeptide is an amino acid sequence selected from any one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41. In a further embodiment, a polypeptide is an amino acid sequence selected from any one of SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, or SEQ ID NO:29.

TABLE 1

ANGPTL3 variant constructs

| SEQ ID | Construct | Sequence |
|---|---|---|
| 14 | 207KQ | IQEPTEISLSSKPRAPRTTPFLQLNEIRNVKHDGIPAECTTIYNRGEHTSGMYAI RPSNSQVFHVYCDVISGSPWTLIQHRIDGSQNFNETWENYKYGFGRLDGEFWLGL EKIYSIVKQSNYVLRIELEDWKDNKHYIEYSFYLGNHETNYTLHLVAITGNVPNA IPENKDLVFSTWDHKAKGHFNCPEGYSGGWWWHDECGENNLNGKYNKPRAQSKPE RRRGLSWKSQNGRLYSIKSTKMLIHPTDSESFE |
| 15 | 207KS | IQEPTEISLSSKPRAPRTTPFLQLNEIRNVKHDGIPAECTTIYNRGEHTSGMYAI RPSNSQVFHVYCDVISGSPWTLIQHRIDGSQNFNETWENYKYGFGRLDGEFWLGL EKIYSIVKQSNYVLRIELEDWKDNKHYIEYSFYLGNHETNYTLHLVAITGNVPNA IPENKDLVFSTWDHKAKGHFNCPEGYSGGWWWHDECGENNLNGKYNKPRASSKPE RRRGLSWKSQNGRLYSIKSTKMLIHPTDSESFE |
| 16 | 225KQ | TTPFLQLNEIRNVKHDGIPAECTTIYNRGEHTSGMYAIRPSNSQVFHVYCDVISG SPWTLIQHRIDGSQNFNETWENYKYGFGRLDGEFWLGLEKIYSIVKQSNYVLRIE LEDWKDNKHYIEYSFYLGNHETNYTLHLVAITGNVPNAIPENKDLVFSTWDHKAK GHFNCPEGYSGGWWWHDECGENNLNGKYNKPRAQSKPERRRGLSWKSQNGRLYSI KSTKMLIHPTDSESFE |
| 17 | 225KS | TTPFLQLNEIRNVKHDGIPAECTTIYNRGEHTSGMYAIRPSNSQVFHVYCDVISG SPWTLIQHRIDGSQNFNETWENYKYGFGRLDGEFWLGLEKIYSIVKQSNYVLRIE LEDWKDNKHYIEYSFYLGNHETNYTLHLVAITGNVPNAIPENKDLVFSTWDHKAK GHFNCPEGYSGGWWWHDECGENNLNGKYNKPRASSKPERRRGLSWKSQNGRLYSI KSTKMLIHPTDSESFE |
| 18 | 225ST | TTPFLQLNEIRNVKHDGIPAECTTIYNRGEHTSGMYAIRPSNSQVFHVYCDVISG SPWTLIQHRIDGSQNFNETWENYKYGFGRLDGEFWLGLEKIYSIVKQSNYVLRIE LEDWKDNKHYIEYSFYLGNHETNYTLHLVAITGNVPNAIPENKDLVFSTWDHKAK GHFNCPEGYSGGWWWHDECGENNLNGKYNKPRAKTKPERRRGLSWKSQNGRLYSI KSTKMLIHPTDSESFE |
| 19 | 226KQ | TPFLQLNEIRNVKHDGIPAECTTIYNRGEHTSGMYAIRPSNSQVFHVYCDVISGS PWTLIQHRIDGSQNFNETWENYKYGFGRLDGEFWLGLEKIYSIVKQSNYVLRIEL EDWKDNKHYIEYSFYLGNHETNYTLHLVAITGNVPNAIPENKDLVFSTWDHKAKG HFNCPEGYSGGWWWHDECGENNLNGKYNKPRAQSKPERRRGLSWKSQNGRLYSIK STKMLIHPTDSESFE |
| 20 | 226KS | TPFLQLNEIRNVKHDGIPAECTTIYNRGEHTSGMYAIRPSNSQVFHVYCDVISGS PWTLIQHRIDGSQNFNETWENYKYGFGRLDGEFWLGLEKIYSIVKQSNYVLRIEL EDWKDNKHYIEYSFYLGNHETNYTLHLVAITGNVPNAIPENKDLVFSTWDHKAKG HFNCPEGYSGGWWWHDECGENNLNGKYNKPRASSKPERRRGLSWKSQNGRLYSIK STKMLIHPTDSESFE |
| 21 | 228KQ | FLQLNEIRNVKHDGIPAECTTIYNRGEHTSGMYAIRPSNSQVFHVYCDVISGSPW TLIQHRIDGSQNFNETWENYKYGFGRLDGEFWLGLEKIYSIVKQSNYVLRIELED WKDNKHYIEYSFYLGNHETNYTLHLVAITGNVPNAIPENKDLVFSTWDHKAKGHF NCPEGYSGGWWWHDECGENNLNGKYNKPRAQSKPERRRGLSWKSQNGRLYSIKST KMLIHPTDSESFE |
| 22 | 228KS | FLQLNEIRNVKHDGIPAECTTIYNRGEHTSGMYAIRPSNSQVFHVYCDVISGSPW TLIQHRIDGSQNFNETWENYKYGFGRLDGEFWLGLEKIYSIVKQSNYVLRIELED WKDNKHYIEYSFYLGNHETNYTLHLVAITGNVPNAIPENKDLVFSTWDHKAKGHF |

TABLE 1 -continued

ANGPTL3 variant constructs

| SEQ ID | Construct | Sequence |
|---|---|---|
| | | NCPEGYSGGWWWHDECGENNLNGKYNKPRASSKPERRRGLSWKSQNGRLYSIKST KMLIHPTDSESFE |
| 23 | 228ST | FLQLNEIRNVKHDGIPAECTTIYNRGEHTSGMYAIRPSNSQVFHVYCDVISGSPW TLIQHRIDGSQNFNETWENYKYGFGRLDGEFWLGLEKIYSIVKQSNYVLRIELED WKDNKHYIEYSFYLGNHETNYTLHLVAITGNVPNAIPENKDLVFSTWDHKAKGHF NCPEGYSGGWWWHDECGENNLNGKYNKPRAKTKPERRRGLSWKSQNGRLYSIKST KMLIHPTDSESFE |
| 24 | 233KQ | EIRNVKHDGIPAECTTIYNRGEHTSGMYAIRPSNSQVFHVYCDVISGSPWTLIQH RIDGSQNFNETWENYKYGFGRLDGEFWLGLEKIYSIVKQSNYVLRIELEDWKDNK HYIEYSFYLGNHETNYTLHLVAITGNVPNAIPENKDLVFSTWDHKAKGHFNCPEG YSGGWWWHDECGENNLNGKYNKPRAQSKPERRRGLSWKSQNGRLYSIKSTKMLIH PTDSESFE |
| 25 | 233KS | EIRNVKHDGIPAECTTIYNRGEHTSGMYAIRPSNSQVFHVYCDVISGSPWTLIQH RIDGSQNFNETWENYKYGFGRLDGEFWLGLEKIYSIVKQSNYVLRIELEDWKDNK HYIEYSFYLGNHETNYTLHLVAITGNVPNAIPENKDLVFSTWDHKAKGHFNCPEG YSGGWWWHDECGENNLNGKYNKPRASSKPERRRGLSWKSQNGRLYSIKSTKMLIH PTDSESFE |
| 26 | 241KQ | GIPAECTTIYNRGEHTSGMYAIRPSNSQVFHVYCDVISGSPWTLIQHRIDGSQNF NETWENYKYGFGRLDGEFWLGLEKIYSIVKQSNYVLRIELEDWKDNKHYIEYSFY LGNHETNYTLHLVAITGNVPNAIPENKDLVFSTWDHKAKGHFNCPEGYSGGWWWH DECGENNLNGKYNKPRAQSKPERRRGLSWKSQNGRLYSIKSTKMLIHPTDSESFE |
| 27 | 241KS | GIPAECTTIYNRGEHTSGMYAIRPSNSQVFHVYCDVISGSPWTLIQHRIDGSQNF NETWENYKYGFGRLDGEFWLGLEKIYSIVKQSNYVLRIELEDWKDNKHYIEYSFY LGNHETNYTLHLVAITGNVPNAIPENKDLVFSTWDHKAKGHFNCPEGYSGGWWWH DECGENNLNGKYNKPRASSKPERRRGLSWKSQNGRLYSIKSTKMLIHPTDSESFE |
| 28 | 242KQ | IPAECTTIYNRGEHTSGMYAIRPSNSQVFHVYCDVISGSPWTLIQHRIDGSQNFN ETWENYKYGFGRLDGEFWLGLEKIYSIVKQSNYVLRIELEDWKDNKHYIEYSFYL GNHETNYTLHLVAITGNVPNAIPENKDLVFSTWDHKAKGHFNCPEGYSGGWWWHD ECGENNLNGKYNKPRAQSKPERRRGLSWKSQNGRLYSIKSTKMLIHPTDSESFE |
| 29 | 242KS | IPAECTTIYNRGEHTSGMYAIRPSNSQVFHVYCDVISGSPWTLIQHRIDGSQNFN ETWENYKYGFGRLDGEFWLGLEKIYSIVKQSNYVLRIELEDWKDNKHYIEYSFYL GNHETNYTLHLVAITGNVPNAIPENKDLVFSTWDHKAKGHFNCPEGYSGGWWWHD ECGENNLNGKYNKPRASSKPERRRGLSWKSQNGRLYSIKSTKMLIHPTDSESFE |
| 30 | 225-455KQ | TTPFLQLNEIRNVKHDGIPAECTTIYNRGEHTSGMYAIRPSNSQVFHVYCDVISG SPWTLIQHRIDGSQNFNETWENYKYGFGRLDGEFWLGLEKIYSIVKQSNYVLRIE LEDWKDNKHYIEYSFYLGNHETNYTLHLVAITGNVPNAIPENKDLVFSTWDHKAK GHFNCPEGYSGGWWWHDECGENNLNGKYNKPRAQSKPERRRGLSWKSQNGRLYSI KSTKMLIHPTD |
| 31 | 225-455KS | TTPFLQLNEIRNVKHDGIPAECTTIYNRGEHTSGMYAIRPSNSQVFHVYCDVISG SPWTLIQHRIDGSQNFNETWENYKYGFGRLDGEFWLGLEKIYSIVKQSNYVLRIE LEDWKDNKHYIEYSFYLGNHETNYTLHLVAITGNVPNAIPENKDLVFSTWDHKAK GHFNCPEGYSGGWWWHDECGENNLNGKYNKPRASSKPERRRGLSWKSQNGRLYSI KSTKMLIHPTD |
| 32 | 226-455KQ | TPFLQLNEIRNVKHDGIPAECTTIYNRGEHTSGMYAIRPSNSQVFHVYCDVISGS PWTLIQHRIDGSQNFNETWENYKYGFGRLDGEFWLGLEKIYSIVKQSNYVLRIEL EDWKDNKHYIEYSFYLGNHETNYTLHLVAITGNVPNAIPENKDLVFSTWDHKAKG HFNCPEGYSGGWWWHDECGENNLNGKYNKPRAQSKPERRRGLSWKSQNGRLYSIK STKMLIHPTD |
| 33 | 226-455KS | TPFLQLNEIRNVKHDGIPAECTTIYNRGEHTSGMYAIRPSNSQVFHVYCDVISGS PWTLIQHRIDGSQNFNETWENYKYGFGRLDGEFWLGLEKIYSIVKQSNYVLRIEL EDWKDNKHYIEYSFYLGNHETNYTLHLVAITGNVPNAIPENKDLVFSTWDHKAKG HFNCPEGYSGGWWWHDECGENNLNGKYNKPRASSKPERRRGLSWKSQNGRLYSIK STKMLIHPTD |
| 34 | 228-455KQ | FLQLNEIRNVKHDGIPAECTTIYNRGEHTSGMYAIRPSNSQVFHVYCDVISGSPW TLIQHRIDGSQNFNETWENYKYGFGRLDGEFWLGLEKIYSIVKQSNYVLRIELED WKDNKHYIEYSFYLGNHETNYTLHLVAITGNVPNAIPENKDLVFSTWDHKAKGHF NCPEGYSGGWWWHDECGENNLNGKYNKPRAQSKPERRRGLSWKSQNGRLYSIKST KMLIHPTD |
| 35 | 228-455KS | FLQLNEIRNVKHDGIPAECTTIYNRGEHTSGMYAIRPSNSQVFHVYCDVISGSPW TLIQHRIDGSQNFNETWENYKYGFGRLDGEFWLGLEKIYSIVKQSNYVLRIELED WKDNKHYIEYSFYLGNHETNYTLHLVAITGNVPNAIPENKDLVFSTWDHKAKGHF |

TABLE 1 -continued

ANGPTL3 variant constructs

| SEQ ID | Construct | Sequence |
|---|---|---|
| | | NCPEGYSGGWWWHDECGENNLNGKYNKPRASSKPERRRGLSWKSQNGRLYSIKSTKMLIHPTD |
| 36 | 233-455KQ | EIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRAQSKPERRRGLSWKSQNGRLYSIKSTKMLIHPTD |
| 37 | 233-455KS | EIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRASSKPERRRGLSWKSQNGRLYSIKSTKMLIHPTD |
| 38 | 241-455KQ | GIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRAQSKPERRRGLSWKSQNGRLYSIKSTKMLIHPTD |
| 39 | 241-455KS | GIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRASSKPERRRGLSWKSQNGRLYSIKSTKMLIHPTD |
| 40 | 242-455KQ | IPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRAQSKPERRRGLSWKSQNGRLYSIKSTKMLIHPTD |
| 41 | 242-455KS | IPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRASSKPERRRGLSWKSQNGRLYSIKSTKMLIHPTD |

Modified ANGPTL3 polypeptides of the invention have at least one substitution in the C-terminal portion of the polypeptide to render the polypeptide protease resistant. The substitution is at an R or K residue so that polypeptides have increased resistance, e.g., to trypsin-like proteases. Any amino acid may be substituted for an R or K in a protease resistant ANGPTL3 polypeptide of the invention. In some embodiments, a substitution is a polar amino acid, e.g., H, N, Q, S, T, A, or Y. In some embodiments, a substitution is H, N, Q, S, T, or Y. In some embodiments, a substitution is S or Q. In some embodiments, the substitution is Q. In some embodiments the substitution is S. In some embodiments, a protease-resistant peptide has an amino acid at position 423, with reference to SEQ ID NO:1, that is other than K or R. In some embodiments, a polypeptide of the invention comprises an amino acid at position 423 that is a polar amino acid. For example, the amino acid at position 423 may be Q or S or another polar amino acid. In certain embodiments a polypeptide of the invention has a Q at position 423. In other embodiments a polypeptide of the invention has an S at position 423. In some embodiments, in addition to substitution at 423, the protease-resistant peptide has a substitution of another R or K in the C-terminus of SEQ ID NO:1, or a variant thereof, wherein the substitution is a polar amino acid other than R or K. In some embodiments, the substitution at position 423 as determined with reference to SEQ ID NO:1, is Q or S.

In some embodiments, a polypeptide of the invention is 250 amino acids or less in length and comprises the amino acid sequence of SEQ ID NO:16, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, or SEQ ID NO:29.

In some embodiments, the invention provides for use of full-length protease-resistant, chondrogenic ANGPTL3 proteins. In some embodiments, the invention provides for protease-resistant ANGPTL3 proteins comprising a C-terminal portion of the ANGPTL3 sequence, or a chondrogenic variant thereof. In certain embodiments ANGPTL3 proteins lack the amino-terminal end of the native protein. In some embodiments, protease-resistant ANGPTL3 proteins of the invention lack the CCD domain and/or lacks significant CCD activity. Thus, in some embodiments, the protease-resistant ANGPTL3 proteins of the invention comprise at least a fragment (e.g., at least 100, 150, 200, 220 or 215 contiguous amino acids) of a human ANGPTL3 protein carboxy-terminal domain, or a substantially identical sequence to the human carboxy-terminal ANGPTL3 protein sequence, wherein the polypeptide and variants thereof retains chondrogenic activity. In some embodiments, a protease-resistant polypeptide of the invention lacks at least a portion of the C-terminal sequence, e.g., lacks 5, 10, 15, or 20 amino acids from the C-terminal end of SEQ ID NO:1 (i.e., lacks 456-460, 451-460, 446-460 or 441-460 of SEQ ID NO:1).

In some embodiments, a protease-resistant ANGPTL3 polypeptide of the invention comprises contiguous amino acids corresponding to the amino acid regions: amino acids 241-455, or 241-460 of SEQ ID NO:1; amino acids 242-455, or 242-460 of SEQ ID NO:1; amino acids 233-455 or 233-460 of SEQ ID NO:1; amino acids 228-455 or 228-460 of SEQ ID NO:1, amino acids 226-455- or 226-260 or amino acids 225-455- or 225-260 of SEQ ID NO:1 in which an amino acid is substituted for an R or K. In some embodiments, a substitution is at position 423 as determined with reference to SEQ ID NO:1. In some embodiments, a protease-resistant polypeptide comprises contiguous amino acids corresponding to the amino acid regions 207-455 or 207-460 of SEQ ID NO:1 in which an amino acid is substituted for R or K. In some embodiments, a substitution is at position 423. In some embodiments, a substitution is a polar amino acid, e.g., H, N, Q, S, T, A, or Y. In some embodiments, a substitution is H, N, Q, S, T, or Y. In some embodiments, a substitution is S or Q. In some embodiments, a substitution is Q.

The invention additionally provides a protease-resistant polypeptide, wherein the polypeptide comprises an amino acid sequence having at least 95% identity, or at least 96%, 97%, 98%, or 99% identity, to amino acids 240-454 of SEQ ID NO:1, amino acids 241-455 of SEQ ID NO:1, or amino acids 242-455 of SEQ ID NO:1 with a substitution at the amino acid corresponding to position 423 of SEQ ID NO:1, where the substituted amino acid is not R, and wherein the polypeptide has chondrogenic activity. In other embodiments, the polypeptide comprises amino acids 240-454 of SEQ ID NO:1, amino acids 241-455 of SEQ ID NO:1, or amino acids 242-455 of SEQ ID NO:1, each polypeptide with a substitution at the amino acid corresponding to position 423 of SEQ ID NO:1, where the substituted amino acid is Q or S.

In some embodiments, a protease-resistant ANGPTL3 polypeptide of the invention comprises an amino acid sequence having at least 95%, or at least 96%, at least 97%, at least 98%, or at least 99% identity to amino acids amino acids 242-455 or 242-460 of SEQ ID NO:1; 241-455 or 241-460 of SEQ ID NO:1; amino acids 233-455 or 233-460 of SEQ ID NO:1; amino acids 228-455 or 228-460 of SEQ ID NO:1, amino acids 226-455- or 226-260 of SEQ ID NO:1, or amino acids 225-455- or 225-260 of SEQ ID NO:1 in which an amino acid is substituted for an R or K. In some embodiments, the substitution is at position 423. In some embodiments, a substitution is a polar amino acid, e.g., H, N, Q, S, T, A, or Y. In some embodiments, a substitution is H, N, Q, S, T, or Y. In some embodiments, the substitution is S or Q. In some embodiments, the substitution is a Q.

In some embodiments, a protease-resistant ANGPTL3 polypeptide of the invention is 250 or 240 or fewer amino acids in length and comprises the amino acid sequence of SEQ ID NO:16, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41. In some embodiments, a protease-resistant ANGPTL3 polypeptide of the invention is 230 or 225 or fewer amino acids in length and comprises the amino acid sequence of SEQ ID NO:24, SEQ ID NO:25, SEQ ID NO:26, SEQ ID NO:27, SEQ ID NO:28, SEQ ID NO:29, SEQ ID NO:36, SEQ ID NO:37, SEQ ID NO:38, SEQ ID NO:39, SEQ ID NO:40, or SEQ ID NO:41.

In some embodiments the protease resistant ANGPTL3 proteins of the invention comprise an amino acid sequence having at least 95% identity, or at least 96%, 97%, 98%, or 99% identity, to the C-terminal canine, bovine, or equine ANGPTL3 protein sequence. In some embodiments, the protease-resistant ANGPTL3 proteins of the invention comprise at least a fragment (e.g., at least 100, 150, 200, 215 contiguous amino acids) of a native canine (SEQ ID NO:4), equine (SEQ ID NO:5), or bovine (SEQ ID NO:6) ANGPTL3 protein sequence, or a substantially identical sequence to the native canine, bovine, or equine ANGPTL3 protein sequence wherein the polypeptide comprises an amino acid that is a polar amino acid other than K or R at position 423, as determined with reference to SEQ ID NO:1, and the polypeptide has chondrogenic activity. In some embodiments, an isolated polypeptide comprises an amino acid sequence having at least 95% identity, or at least 96%, 97%, 98%, or 99% identity, to SEQ ID NO:42 or SEQ ID NO:43, wherein the polypeptide comprises an amino acid that is a polar amino acid other than K or R at position 423, as determined with reference to SEQ ID NO:1, and the polypeptide has chondrogenic activity. In some embodiments, a polypeptide has at least 95% identity, or at least or at least 96%, 97%, 98%, or 99% identity, to SEQ ID NO:42, or SEQ ID NO:43 wherein the polypeptide comprises an amino acid that is a polar amino acid other than K or R at position 423, as determined with reference to SEQ ID NO:1, and the polypeptide has chondrogenic activity. In certain embodiments a polypeptide comprises SEQ ID NO:42, or SEQ ID NO:43. In a further embodiment, a polypeptide is SEQ ID NO:42, or SEQ ID NO:43.

In some embodiments, a protease-resistant ANGPTL3 of the invention comprises an amino acid sequence that has at least 95%, or at least 96%, 97%, 98%, or at least 99% identity to amino acids 232-454 of SEQ ID NO:4, amino acids 240-454 of SEQ ID NO:4, amino acids 227-454 of SEQ ID NO:4, or amino acids 224-454 of SEQ ID NO:4 in which an amino acid is substituted for an R or K. In some embodiments, the substitution is at position 422 of SEQ ID NO:4, which corresponds to position 423 of SEQ ID NO:1. In some embodiments, a substitution is a polar amino acid, e.g., H, N, Q, S, T, A, or Y. In some embodiments, a substitution is H, N, Q, S, T, or Y. In some embodiments, the substitution is S or Q. In some embodiments, the substitution is a Q.

In some embodiments, a protease-resistant ANGPTL3 of the invention comprises an amino acid sequence that has at least 95%, or at least 96%, 97%, 98%, or at least 99% identity to amino acids 233-455 of SEQ ID NO:5, amino acids 241-455 of SEQ ID NO:5, amino acids 228-455 of SEQ ID NO:5, or amino acids 225-455 of SEQ ID NO:5 in which an amino acid is substituted for an R or K. In some embodiments, the substitution is at position 423 of SEQ ID NO:5, which corresponds to position 423 of SEQ ID NO:1. In some embodiments, a substitution is a polar amino acid, e.g., H, N, Q, S, T, A, or Y. In some embodiments, a substitution is H, N, Q, S, T, or Y. In some embodiments, the substitution is S or Q. In some embodiments, the substitution is a Q.

In some embodiments, a protease-resistant ANGPTL3 of the invention comprises an amino acid sequence that has at least 95%, or at least 96%, 97%, 98%, or at least 99% identity to amino acids 233-455 of SEQ ID NO:6, amino acids 241-455 of SEQ ID NO:6, amino acids 228-455 of SEQ ID NO:6, or amino acids 225-455 of SEQ ID NO:6 in which an amino acid is substituted for an R or K. In some embodiments, the substitution is at position 422 of SEQ ID NO:6, which corresponds to position 423 of SEQ ID NO:1. In some embodiments, a substitution is a polar amino acid, e.g., H, N, Q, S, T, A, or Y. In some embodiments, a substitution is H, N, Q, S, T, or Y. In some embodiments, the substitution is S or Q. In some embodiments, the substitution is a Q.

In some embodiments, a protease-resistant ANGPTL3 polypeptide of the invention comprises contiguous amino acids corresponding to the amino acid regions: amino acids 240-454 of SEQ ID NO:4; amino acids 232-454 of SEQ ID NO:4; amino acids 227-454 of SEQ ID NO:4, or amino acids 224-454 of SEQ ID NO:4 in which an amino acid is substituted for an R or K. In some embodiments, the substitution is at position 422 of SEQ ID NO:4 (which is position 423 as determined with reference to SEQ ID NO:1). In some embodiments, a substitution is a polar amino acid, e.g., H, N, Q, S, T, A, or Y. In some embodiments, a substitution is H, N, Q, S, T, or Y. In some embodiments, the substitution is S or Q. In some embodiments, the substitution is Q.

In some embodiments, a protease-resistant ANGPTL3 polypeptide of the invention comprises contiguous amino acids corresponding to the amino acid regions: amino acids 241-455 of SEQ ID NO:5; amino acids 233-455 of SEQ ID NO:5; amino acids 228-455 of SEQ ID NO:5, or amino acids 225-455 of SEQ ID NO:5 in which an amino acid is substituted for an R or K. In some embodiments, the substitution is at position 423 (which corresponds to position 423 as determined with reference to SEQ ID NO:1). In some embodiments, a substitution is a polar amino acid, e.g., H, N, Q, S, T, A, or Y. In some embodiments, a substitution is H, N, Q, S, T, or Y. In some embodiments, the substitution is S or Q. In some embodiments, the substitution is Q.

In some embodiments, a protease-resistant ANGPTL3 polypeptide of the invention comprises contiguous amino acids corresponding to the amino acid regions: amino acids 241-455 of SEQ ID NO:6; amino acids 233-455 of SEQ ID NO:6; amino acids 228-455 of SEQ ID NO:6, or amino acids 225-455 of SEQ ID NO:6 in which an amino acid is substituted for an R or K. In some embodiments, the substitution is at position 422 of SEQ ID NO:6 (which is position 423 as determined with reference to SEQ ID NO:1). In some embodiments, a substitution is a polar amino acid, e.g., H, N, Q, S, T, A, or Y. In some embodiments, a substitution is H, N, Q, S, T, or Y. In some embodiments, the substitution is S or Q. In some embodiments, the substitution is Q.

The ANGPTL3 proteins of the invention as described above may include native ANGPTL3 protein sequences flanking the regions described above. Alternatively, in some embodiments, the ANGPTL3 proteins of the invention can include non-native ANGPTL3 protein flanking sequences. For example, the chondrogenic active portion of an ANGPTL3 protein can be fused to one or more fusion partners and/or heterologous amino acids to form a fusion protein. Fusion partner sequences can include, but are not limited to, amino acid tags, non-L (e.g., D-) amino acids or other amino acid mimetics to extend in vivo half-life and/or protease resistance, targeting sequences or other sequences.

In some embodiments, a polypeptide of the invention is PEGylated. In some embodiments, a polypeptide of the invention is fused to a heterologous peptide. In certain embodiments a polypeptide is fused to any one of human serum albumin (HSA), an immunoglobulin heavy chain constant region (Fc), a polyhistidine, a glutathione S transferase (GST), a thioredoxin, a protein A, a protein G, a maltose binding protein (MBP), or a fragment of any of the foregoing heterologous polypeptide(s). In particular embodiments a heterologous polypeptide is fused at the amino-terminal end of the polyptide of the invention. In additional or alternative embodiments a heterologous polypeptide is fused at the carboxy-terminal end of the polypeptide of the invention.

ANGPTL3 proteins of the invention have chondrogenic activity and are protease-resistant. As defined herein, chondrogenesis or chondrogenic activity refers to the development of chondrocytes from MSCs. Indicators of chondrogenic activity include, but are not limited to, cartilage matrix production. Cartilage matrix production may be measured by various markers, for example, such as Sox9, type II collagen, or glycosaminoglycan (GAG) production. In some embodiments, GAG production is measured as a marker for cartilage matrix production. In some embodiments, a 3-fold increase in GAG production with cartilage specific protein expression indicates positive cartilage matrix production.

A polypeptide may be evaluated for protease resistance using any known assay that measures cleavage by a serine protease such as trypsin. In some embodiments, the protease employed to evaluate proteolysis susceptibility is the serine protease trypsin. A polypeptide is considered to be protease-resistant if it has reduced sensitivity to trypsin when compared to its wild-type counterpart. An example of an assay is to measure the amount of cleaved product that is generated when a polypeptide is exposed to trypsin over a period of time in comparison to a corresponding native human peptide. Cleavage can be measured using any known assay, e.g., SDS PAGE or LCMS. An illustrative assay is provided in the Examples section.

In an illustrative assay, limited proteolysis by trypsinolysis is performed by incubating 10 ng of the protein to be evaluated with trypsin at mass ratio of 8000:1 (Protein: Trypsin) for 1 hr at room temperature. The trypsinolysis reaction can then be quenched by addition of acetic acid to bring the reaction to pH 3.0. The quenched samples are then separated analyzed by SDS-PAGE, e.g., on a 4-12% Tris-Bis gel to identify proteins which are resistant to cleavage from those that are cleaved by the appearance of a fragment that is generated by trypsin cleavage. The cleavage product is absent or reduced in the protease-resistant polypeptides in comparison to their wildtype counterparts.

In some embodiments, the ANGPTL3 polypeptides of the invention will comprise at least one non-naturally encoded amino acid. In some embodiments, a polypeptide comprises 1, 2, 3, 4, or more unnatural amino acids. Methods of making and introducing a non-naturally-occurring amino acid into a protein are known. See, e.g., U.S. Pat. Nos. 7,083,970; and 7,524,647. The general principles for the production of orthogonal translation systems that are suitable for making proteins that comprise one or more desired unnatural amino acid are known in the art, as are the general methods for producing orthogonal translation systems. For example, see International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" WO 2004/094593, entitled "EXPANDING THE EUKARYOTIC GENETIC CODE;" WO 2005/019415, filed Jul. 7, 2004; WO 2005/007870, filed Jul. 7, 2004; WO 2005/007624, filed Jul. 7, 2004; WO 2006/110182, filed Oct. 27, 2005, entitled "ORTHOGONAL TRANSLATION COMPONENTS FOR THE VIVO INCORPORATION OF UNNATURAL AMINO ACIDS" and WO 2007/103490, filed Mar. 7, 2007, entitled "SYSTEMS FOR THE EXPRESSION OF ORTHOGONAL TRANSLATION COMPONENTS IN EUBACTERIAL HOST CELLS." For discussion of orthogonal translation systems that incorporate unnatural amino acids, and methods for their production and use, see also, Wang and Schultz, (2005) "Expanding the Genetic Code." Angewandte Chemie Int Ed 44: 34-66; Xie and Schultz, (2005) "An Expanding Genetic Code." Methods 36: 227-238; Xie and Schultz, (2005) "Adding Amino Acids to the Genetic Repertoire." Curr Opinion in Chemical Biology 9: 548-554; and Wang, et al., (2006) "Expanding the Genetic Code." Annu Rev Biophys Biomol Struct 35: 225-249; Deiters, et al, (2005) "In vivo incorporation of an alkyne into proteins in *Escherichia coli*." Bioorganic & Medicinal Chemistry Letters 15:1521-1524; Chin, et al., (2002) "Addition of p-Azido-L-phenylalanine to the Genetic Code of *Escherichia coli*." J Am Chem Soc 124: 9026-9027; and International Publication No. WO2006/034332, filed on Sep. 20, 2005. Additional details are found in U.S. Pat. Nos. 7,045,337; 7,083,970; 7,238,510; 7,129,333; 7,262,040; 7,183,082; 7,199,222; and 7,217,809.

A "non-naturally encoded amino acid" refers to an amino acid that is not one of the common amino acids or pyrolysine, pyrroline-carboxy-lysine, or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine, pyrroline-carboxy-lysine, and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

A non-naturally encoded amino acid is typically any structure having any substituent side chain other than one used in the twenty natural amino acids. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Another type of modification that can optionally be introduced into the ANGPTL3 proteins of the invention (e.g. within the polypeptide chain or at either the N- or C-terminal), e.g., to extend in vivo half-life, is PEGylation or incorporation of long-chain polyethylene glycol polymers (PEG). Introduction of PEG or long chain polymers of PEG increases the effective molecular weight of the present polypeptides, for example, to prevent rapid filtration into the urine. In some embodiments, a Lysine residue in the ANGPTL3 sequence is conjugated to PEG directly or through a linker. Such linker can be, for example, a Glu residue or an acyl residue containing a thiol functional group for linkage to the appropriately modified PEG chain. An alternative method for introducing a PEG chain is to first introduce a Cys residue at the C-terminus or at solvent exposed residues such as replacements for Arg or Lys residues. This Cys residue is then site-specifically attached to a PEG chain containing, for example, a maleimide function. Methods for incorporating PEG or long chain polymers of PEG are well known in the art (described, for example, in Veronese, F. M., et al., *Drug Disc. Today* 10: 1451-8 (2005); Greenwald, R. B., et al., *Adv. Drug Deliv. Rev.* 55: 217-50 (2003); Roberts, M. J., et al., *Adv. Drug Deliv. Rev.,* 54: 459-76 (2002)), the contents of which is incorporated herein by reference. Other methods of polymer conjugations known in the art can also be used in the present invention. In some embodiments, poly(2-methacryloyloxyethyl phosphorylcholine) (PMPC) is introduced as a polymer conjugate with the ANGPTL3 proteins of the invention (see, e.g., WO2008/098930; Lewis, et al., *Bioconjug Chem.,* 19: 2144-55 (2008)). In some embodiments, a phosphorylcholine-containing polymer conjugate with the ANGPTL3 proteins can be used in the present invention. A person of skill would readily recognize that other biocompatible polymer conjugates can be utilized.

A more recently reported alternative approach for incorporating PEG or PEG polymers through incorporation of non-natural amino acids (as described above) can be performed with the present polypeptides. This approach utilizes an evolved tRNA/tRNA synthetase pair and is coded in the expression plasmid by the amber suppressor codon (Deiters, A, et al. (2004). *Bio-org. Med. Chem. Lett.* 14, 5743-5). For example, p-azidophenylalanine can be incorporated into the present polypeptides and then reacted with a PEG polymer having an acetylene moiety in the presence of a reducing agent and copper ions to facilitate an organic reaction known as "Huisgen [3+2]cycloaddition."

In certain embodiments, the present invention also contemplates specific mutations of the ANGPTL3 proteins so as to alter the glycosylation of the polypeptide. Such mutations may be selected so as to introduce or eliminate one or more glycosylation sites, including but not limited to, O-linked or N-linked glycosylation sites. In certain embodiments, the ANGPTL3 proteins of the present invention have glycosylation sites and patterns unaltered relative to the naturally-occurring ANGPTL3 proteins. In certain embodiments, a variant of ANGPTL3 proteins includes a glycosylation variant wherein the number and/or type of glycosylation sites have been altered relative to the naturally-occurring ANGPTL3 proteins. In certain embodiments, a variant of a polypeptide comprises a greater or a lesser number of N-linked glycosylation sites relative to a native polypeptide. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. In certain embodiments, a rearrangement of N-linked carbohydrate chains is provided, wherein one or more N-linked glycosylation sites (typically those that are naturally occurring) are eliminated and one or more new N-linked sites are created.

Exemplary ANGPTL3 proteins variants include cysteine variants wherein one or more cysteine residues are deleted from or substituted for another amino acid (e.g., serine) relative to the amino acid sequence of the naturally-occurring ANGPTL3 proteins. In certain embodiments, cysteine variants may be useful when ANGPTL3 proteins must be refolded into a biologically active conformation such as after the isolation of insoluble inclusion bodies. In certain embodiments, cysteine variants have fewer cysteine residues than the native polypeptide. In certain embodiments, cysteine variants have an even number of cysteine residues to minimize interactions resulting from unpaired cysteines.

In some embodiments, functional variants or modified forms of the ANGPTL3 proteins include fusion proteins of an ANGPTL3 protein of the invention and one or more fusion domains. Well known examples of fusion domains include, but are not limited to, polyhistidine, Glu-Glu, glutathione S transferase (GST), thioredoxin, protein A, protein G, an immunoglobulin heavy chain constant region (Fc), maltose binding protein (MBP), and/or human serum albumin (HSA). A fusion domain or a fragment thereof may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QLAexpress™ system (Qiagen) useful with ($HIS_6$) fusion partners. As another example, a fusion domain may be selected so as to facilitate detection of the ANGPTL3 proteins. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain embodiments, an ANGPTL3 protein is fused with a domain that stabilizes the ANGPTL3 protein in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, as desired). Fusions may be constructed such that the heterologous peptide is fused at the amino terminus of a polypeptide of the invention and/or at the carboxy terminus of a polypeptide of the invention.

III. Nucleic Acids Encoding Angiopoietin-like 3 Protease-Resistant Polypeptides

The invention also provides nucleic acids encoding protease resistant polypeptides of the invention and expression vectors and host cells for expression of a protease resistant polypeptide. In other aspects, the invention provides a polynucleotide encoding a polypeptide of the invention and expression vectors and host cells comprising such a polynucleotide. In some embodiments, the polynucleotide is optimized for expression in the host cells. In some embodiments, the invention provides a method of ameliorating or preventing arthritis or joint injury in a human patient, the method comprising: administering to a joint of the patient an expression vector encoding a polypeptide of the invention whereupon expression of the polypeptide ameliorates or prevents arthritis or joint injury in the patient. In some embodiments, the patient has arthritis or joint injury. In some embodiments, the individual does not have, but is at risk for, arthritis or joint injury. In some embodiments, the arthritis is osteoarthritis, trauma arthritis, or autoimmune arthritis.

Expressing polypeptides of the invention employs routine techniques in the field of recombinant genetics. Basic texts disclosing the general methods of use in this invention include Sambrook and Russell eds. (2001) Molecular Cloning: A Laboratory Manual, 3rd edition; the series Ausubel et al. eds. (2007 with updated through 2010) Current Protocols in Molecular Biology, among others known in the art.

Expression can employ any appropriate host cells known in the art, for example, mammalian host cells, bacterial host cells, yeast host cells, insect host cells, etc. Both prokaryotic and eukaryotic expression systems are widely available. In some embodiments, the expression system is a mammalian cell expression, such as a CHO cell expression system. In some embodiments, a nucleic acid may be codon-optimized to facilitate expression in a desired host cell.

Nonviral vectors and systems include plasmids and episomal vectors, typically comprising an expression cassette for expressing a protein or RNA, and human artificial chromosomes (see, e.g., Harrington et al., Nat Genet 15:345, 1997). For example, nonviral vectors useful for expression of the polypeptides of the invention in mammalian (e.g., human) cells include pThioHis A, B & C, pcDNA3. I/His, pEBVHis A, B & C (Invitrogen, San Diego, Calif.), MPSV vectors, and numerous other vectors known in the art for expressing other proteins. Useful viral vectors include, but are not limited to, vectors based on adenoviruses, adenoassociated viruses, herpes viruses, vectors based on SV40, papilloma virus, HBP Epstein Barr virus, fowpox vectors, vaccinia virus vectors and Semliki Forest virus (SFV).

The choice of expression vector depends on the intended host cells in which the vector is to be expressed. Typically, the expression vectors contain a promoter and other regulatory sequences (e.g., enhancers) that are operably linked to the polynucleotides encoding a polypeptide of the invention. In some embodiments, an inducible promoter is employed to prevent expression of inserted sequences except under inducing conditions. Inducible promoters include, e.g., arabinose, lacZ, a metallothionein promoter, a glucocorticoid promoters or a heat shock promoter. In addition, other regulatory elements may also be incorporated to improve expression of a nucleic acid encoding a polypeptide of the invention, e.g., enhancers, ribosomal binding site, transcription termination sequences, and the like.

In some embodiments, a nucleic acid encoding an polypeptide of the invention may also include a sequence encoding a secretion signal sequence so that the polypeptide is secreted from the host cell. Such a sequence can be provided by the vector, or as part of the ANGPTL3 nucleic acid that is present in the vector.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation: nucleic acid conjugates, naked DNA, artificial virions, fusion to the herpes virus structural protein VP22, agent-enhanced uptake of DNA, and ex vivo transduction. For long-term, high-yield production of recombinant proteins, stable expression will often be desired. For example, cell lines which stably express polypeptides of the invention can be prepared using expression vectors of the invention which contain viral origins of replication or endogenous expression elements and a selectable marker gene.

In some embodiments, nucleic acids encoding protease resistant ANGPTL3 polypeptides of the invention can be delivered to a patient for treatment of a joint-related injury or disease. Delivery of such nucleic acids can be achieved using any means known in the art, but is typically performed using direct injection into the affected joint. In some embodiments, a DNA is delivered as naked DNA using direct injection into the joint. In some embodiments, a viral vector is employed, including, but not limited to, an adenovirus or adenovirus-associated vector, a herpes virus vector, fowlpox virus, or a vaccinia virus vector.

IV. Methods of Therapeutic use of Polypeptides, and Indications

Provided methods of the invention include a method of treating a subject comprising administering to the subject a therapeutically effective amount of a polypeptide of the invention, wherein the subject has or is at risk of joint damage or arthritis. The invention also provides a method of ameliorating or preventing arthritis or joint injury in a human patient, the method comprising: administering to a joint of the patient a composition comprising an effective amount of a polypeptide of the invention, thereby ameliorating or preventing arthritis or joint injury in the patient. In some embodiments, the patient has arthritis or joint injury. In some embodiments, the individual does not have, but is at risk for, arthritis or joint injury. In some embodiments, the arthritis is osteoarthritis, trauma arthritis, or autoimmune arthritis. In some embodiments, the composition administered to the further comprises hyaluronic acid.

In another aspect, the invention provides a method of inducing differentiation of mesenchymal stem cells into chondrocytes, the method comprising, contacting mesenchymal stem cells with a sufficient amount of a polypeptide of the invention to induce differentiation of the stem cells into chondrocytes. In some embodiments, the method is performed in vivo and the stem cells are present in a human patient.

It is contemplated that polypeptides, compositions, and methods of the present invention may be used to treat, ameliorate or prevent any type of articular cartilage damage (e.g., joint damage or injury) including, for example, damage arising from a traumatic event or tendon or ligament tear. In some embodiments, proteins of the invention are administered to prevent or ameliorate arthritis or joint damage, for example where there is a genetic or family history of arthritis or joint damage or joint injury or prior or during joint surgery. In some embodiments polypeptides, compositions and methods are used to treat joint damage. In particular embodiments joint damage is traumatic joint injury. In other embodiments joint damage is damage arising from age or inactivity. In yet other embodiments joint damage is damage arising from an autoimmune disorder. In some embodiments of the invention, polypeptides, compositions, and methods of the present invention may be used to treat, ameliorate or prevent osteoarthritis. In some embodiments, the polypeptides, compositions and methods are used to ameliorate or prevent arthritis in a subject at risk of having or acquiring arthritis. In some embodiments, the polypeptides, compositions and methods are used to ameliorate or prevent joint damage in a subject at risk of having or acquiring joint damage.

In some embodiments, polypeptides, compositions, and methods of the present invention provide a method for stimulating chondrocyte proliferation and cartilage production in cartilagenous tissues that have been damaged, e.g., due to traumatic injury or chondropathy. In particular embodiments polypeptides, compositions, and methods of the present invention are useful for treatment of cartilage damage in joints, e.g., at articulated surfaces, e.g., spine, shoulder, elbow, wrist, joints of the fingers, hip, knee, ankle, and joints of the feet. Examples of diseases or disorders that may benefit from treatment include osteoarthritis, rheumatoid arthritis, other autoimmune diseases, or osteochondritis dessicans. In addition, cartilage damage or disruption occurs as a result of certain genetic or metabolic disorders, cartilage malformation is often seen in forms of dwarfism in humans, and/or cartilage damage or disruption is often a result of reconstructive surgery; thus polypeptides, compositions, and methods would be useful therapy in these patients, whether alone or in connection with other approaches.

It is further contemplated that polypeptides, compositions, and methods of the present invention may be used to treat, ameliorate or prevent various cartilagenous disorders and/or associated symptoms or effects of such conditions. Exemplary conditions or disorders for treatment, amelioration and/or prevention with polypeptides, compositions, and methods of the invention, include, but are not limited to systemic lupus erythematosis, rheumatoid arthritis, juvenile chronic arthritis, osteoarthritis, degenerative disc disease, spondyloarthropathies, Ehlers Danlos syndrome, systemic sclerosis (scleroderma) or tendon disease. Other conditions or disorders that may benefit from treatment with polypeptides for amelioration of associated effects include idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barr syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

A "patient" as used herein refers to any subject that is administered a therapeutic polypeptide of the invention. It is contemplated that the polypeptides, compositions, and methods of the present invention may be used to treat a mammal. As used herein a "subject" refers to any mammal, including humans, domestic and farm animals, and zoo, sports or pet animals, such as cattle (e.g. cows), horses, dogs, sheep, pigs, rabbits, goats, cats, etc. In some embodiments of the invention, the subject is a human. In certain embodiments, the subject is a horse. In other embodiments the subject is a dog.

In some embodiments, the polypeptides of the invention can be heterologous to the mammal to be treated. For example, a human ANGPTL3 protein or fragments thereof, a protein or peptide derived from a human ANGPTL3 protein (e.g., a modified human ANGPTL3 protein, a conservative variant of human ANGPTL3 protein, a peptidomimetic derived from a human ANGPTL3 protein) are used in the treatment of an animal such as an equine, bovine or canine. In some embodiments, a heterologous ANGPTL3 protein can be used to expand chondrocyte populations in culture for transplantation. In some embodiments, expanded cultures will then be optionally admixed with polypeptides and compositions homologous to the mammal to be treated, and placed in the joint space or directly into the cartilage defect. Alternatively, polypeptides of the invention are derived from the same species, i.e., a human ANGPTL3 protein or fragments thereof, a protein or peptide derived from a human ANGPTL3 protein (e.g., a modified human ANGPTL3 protein, a conservative variant of human ANGPTL3 protein, a peptidomimetic derived from a human ANGPTL3 protein) is used in the treatment of a human patient. By using a protein derived from the same species of mammal as is being treated, inadvertent immune responses may be avoided.

In some embodiments, polypeptides and compositions of the present invention are applied by direct injection into the synovial fluid of a joint, systemic administration (oral or intravenously) or directly into a cartilage defect, either alone or complexed with a suitable carrier for extended release of protein. In some embodiments, polypeptides or compositions are administered in a biocompatible matrix or scaffold. Polypeptides, compositions, and methods of the present invention can also be used in conjunction with a surgical procedure at an affected joint. Administration of a polypeptide of the invention may occur prior to, during or in conjunction with, and/or after a surgical procedure. For example, polypeptides, compositions and methods of the invention can be used to expand chondrocyte populations in culture for autologous or allogenic chondrocyte implantation (ACI). Chondrocytes can be optionally implanted with concurrent treatment consisting of administration of polypeptides and compositions of the present invention. In these procedures, for example, chondrocytes can be harvested arthroscopically from an uninjured minor load-bearing area of a damaged joint, and can be cultured in vitro, optionally in the presence of polypeptides and compositions of the present invention and/or other growth factors to increase the number of cells prior to transplantation. Expanded cultures are then optionally admixed with polypeptides and compositions of the present invention and/or placed in the joint space or directly into the defect. In certain embodiments, expanded cultures (optionally with polypeptides of the present invention) are placed in the joint space suspended in a matrix or membrane. In other embodiments, polypeptides and compositions of the present invention can be used in combination with one or more periosteal or perichondrial grafts that contain cartilage forming cells and/or help to hold the transplanted chondrocytes or chondrocyte precursor cells in place. In some embodiments, polypeptides and compositions of the present invention are used to repair cartilage damage in conjunction with other procedures, including but not limited to lavage of a joint, stimulation of bone marrow, abrasion arthroplasty, subchondral drilling, or microfracture of proximal subchondral bone. Optionally, following administration of polypeptides and compositions of the present invention and growth of cartilage, additional surgical treatment may be beneficial to suitably contour newly formed cartilage surface(s).

V. Pharmaceutical Compositions

Therapeutic compositions comprising provided polypeptides are within the scope of the present invention, and are specifically contemplated in light of the identification of several polypeptide sequences exhibiting enhanced stability and protease resistance. Thus, in a further aspect, the invention provides a pharmaceutical composition comprising a therapeutically effective amount of a polypeptide of the invention. In certain embodiments, pharmaceutical compositions further comprise a pharmaceutically or physiologically acceptable carrier. In some embodiments, a pharmaceutical composition further comprises a hyaluronic acid or a derivative thereof.

In addition, the invention provides a method of ameliorating or preventing arthritis or joint injury in a human patient, the method comprising: administering to a joint of the patient a composition comprising an effective amount of a polypeptide of the invention, thereby ameliorating or preventing arthritis or joint injury in the patient. In some embodiments, the patient has arthritis or joint injury. In some embodiments, the individual does not have, but is at risk for, arthritis or joint injury. In some embodiments, the arthritis is osteoarthritis, trauma arthritis, or autoimmune arthritis. In some embodiments, the composition administered to the further comprises hyaluronic acid.

In another aspect, the invention provides a method of inducing differentiation of mesenchymal stem cells into chondrocytes, the method comprising, contacting mesenchymal stem cells with a sufficient amount of a polypeptide of the invention to induce differentiation of the stem cells into chondrocytes. In some embodiments, the method is performed in vivo, the stem cells are present in a human patient, and the contacting comprises administering to a joint of the patient a composition comprising an effective amount of a polypeptide of the invention, thereby inducing differentiation of stem cells into chondrocytes, and generation of cartilage.

Therapeutic compositions comprising nucleic acids encoding polypeptides of the invention can be delivered to a patient for treatment of a joint-related injury or disease, and are also within the scope of the present invention. In some embodiments, pharmaceutical compositions comprise naked DNA encoding a polypeptide of the invention. In some embodiments, a viral vector is employed to effect delivery and a pharmaceutical composition comprises a vector encoding a polypeptide of the invention, including, but not limited to, an adenovirus or adenovirus-associated vector, a herpes virus vector, fowlpox virus, or a vaccinia virus vector. Pharmaceutical compositions comprise a therapeutically effective amount of a nucleic acid encoding a polypeptide of the invention with a pharmaceutically or physiologically acceptable carrier.

In another aspect of the present invention, provided polypeptides for use as a medicament for treatment of joint damage is contemplated. In certain embodiments polypeptides of the invention for use as a medicament for amelioration of arthritis or joint damage are provided. In some embodiments arthritis is osteoarthritis, trauma arthritis or autoimmune arthritis. In some embodiments joint damage is traumatic joint injury, autoimmune damage, age related damage, or damage related to inactivity. In other embodiments, nucleic acid encoding a polypeptide of the invention for use in a medicament is provided.

Formulations suitable for administration include excipients, including but not limited to, aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In certain embodiments pharmaceutical compositions comprise a therapeutically effective amount of a peptide in admixture with a pharmaceutically acceptable formulation agent selected for suitability with the mode of administration, delivery format, and desired dosage. See, e.g., Remington's Pharmaceutical Sciences ($18^{th}$ Ed., A. R. Gennaro, ed., Mack Publishing Company 1990), and subsequent editions of the same. The primary vehicle or carrier in a pharmaceutical composition can be aqueous or non-aqueous in nature. For example, a suitable vehicle or carrier for injection can be water, physiological saline solution or artificial cerebrospinal fluid, optionally supplemented with other materials common in compositions for parenteral administration. For example, buffers may be used, e.g., to maintain the composition at physiological pH or at a slightly lower pH, typically within a range of from about pH 5 to about pH 8, and may optionally include sorbitol, serum albumin or other additional component. In certain embodiments pharmaceutical compositions comprising polypeptides or a nucleic acid encoding a polypeptide of the invention can be prepared for storage in a lyophilized form using appropriate excipients (e.g., sucrose).

In yet other embodiments formulation with an agent, such as injectable microshperes, bio-erodable particles, polymeric compounds, beads, or liposomes or other biocompatible matrix that provides for controlled or sustained release of the polypeptide or a nucleic acid encoding a polypeptide of the invention can then be delivered via a depot injection. For example, polypeptides or nucleic acid encoding a polypeptide of the invention may be encapsulated in liposomes, or formulated as microparticles or microcapsules or may be incorporated into other vehicles, such as biodegradable polymers, hydrogels, cyclodextrins (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722) or by the use of conjugates. Still other suitable delivery mechanisms include implantable delivery devices.

The dose of a compound of the present invention for treating the above-mentioned diseases or disorders varies depending upon the manner of administration, the age and/or the body weight of the subject, and the condition of the subject to be treated, and ultimately will be decided by the attending physician or veterinarian. The dose administered to a subject, in the context of the present invention should be sufficient to effect a beneficial response in the subject over time. Such a dose is a "therapeutically effective amount". Accordingly, an appropriate dose may be determined by the efficacy of the particular protein or a nucleic acid encoding a polypeptide of the invention employed and the condition of the subject, as well as the body weight or surface area of the area to be treated. The size of the dose also will be determined by the existence, nature, and extent of any adverse side-effects that accompany the administration of a particular protein or vector in a particular subject. Administration can be accomplished via single or divided doses, or as a continuous infusion via an implantation device or catheter. Frequency of dosing will depend upon the pharmacokinetic parameters of the polypeptide or a nucleic acid encoding a polypeptide of the invention in the formulation used. A clinician may titer dosage and/or modify administration to achieve the desired therapeutic effects. A typical dosage ranges from about 0.01 μg/kg to about 100 mg/kg, depending on the factors. In certain embodiments, a dosage ranges from about 0.1 μg/kg up to about 10 mg/kg; or about 0.1 μg/kg; about 0.5 μg/kg; about 1 μg/kg; about 2 μg/kg; about 0.5 μg/kg; about 10 μg/kg; about 15 μg/kg; about 20 μg/kg; about 25 μg/kg; about 30 μg/kg; about 35 μg/kg; about 40 μg/kg; about 45 μg/kg; about 50 μg/kg; about 55 μg/kg; about 60 μg/kg; about 65 μg/kg; about 75 μg/kg; about 85 μg/kg; about 100 μg/kg. In certain embodiments a dosage is about 50 μg/kg; about 100 μg/kg; about 150 μg/kg; about 200 μg/kg; about 250 μg/kg; about 300 μg/kg; about 350 μg/kg; about 400 μg/kg; about 450 μg/kg; about 500 μg/kg; about 550 μg/kg; about 600 μg/kg; about 650 μg/kg; about 700 μg/kg; about 750 μg/kg; about 800 μg/kg; about 850 μg/kg; about 900 μg/kg; about 950 μg/kg; about 1 mg/kg; about 2 mg/kg; about 3 mg/kg; about 4 mg/kg; about 5 mg/kg; about 6 mg/kg; about 7 mg/kg; about 8 mg/kg; about 9 mg/kg; about 10 mg/kg.

VI. Methods of Administration

Any method for delivering the proteins or a nucleic acid encoding a polypeptide of the invention of the invention to an affected joint can be used. In the practice of this invention, compositions can be parenterally administered, for example injected, e.g., intra-articularly (i.e., into a joint), intravenously, intramuscularly, subcutaneously; infused, or implanted, e.g., in a membrane, matrix, device, etc. When injected, infused or implanted, delivery can be directed into the suitable tissue or joint, and delivery may be direct bolus delivery or continuous delivery. In some embodiments delivery can be in a suitable tissue located in close proximity to an affected joint. In some embodiments delivery may be via diffusion, or via timed release bolus. In some embodiments, a controlled release system (e.g., a pump) can be placed in proximity of the therapeutic target, e.g., the joint to which the polypeptide is administered. In other embodiments, compositions can be selected for ingestion, e.g., inhalation or oral delivery.

The therapeutic polypeptides or a nucleic acid encoding a polypeptide of the invention of the present invention can also be used effectively in combination with one or more additional active agents (e.g., hyaluronic acid or a derivative or salt thereof, growth factor (e.g., FGF18, BMP7), chondrogenic agent (e.g., oral salmon calcitonin, SD-6010 (iNOS inhibitor), vitamin D3 (choliecalciferol), collagen hydrolyzate, rusalatide acetate, avocado soy unsaponifiables (ASU), a compound described in WO2012/129562, kartogenin), a steroid, a non-steroidal anti-inflammatory agent (NSAID), etc.) depending on the desired therapy or effect to improve or enhance the therapeutic effect of either. This process can involve administering both agents to the patient at the same time, either as a single composition or pharmacological formulation that includes both agents, or by administering two distinct compositions or formulations, wherein one composition includes a polypeptide or a polynucleotide encoding a polypeptide of the invention and the other includes the second agent(s). Administration of a therapeutic composition comprising a polypeptide or a polynucleotide encoding a polypeptide of the invention can precede or follow administration of the second agent by intervals ranging from minutes to weeks.

Formulations of compounds can be stored in sterile vials as a solution, suspension, gel, emulsion, solid, or as a dehydrated or lyophilized powder. Formulations can be presented in unit-dose or multi-dose sealed containers, such as ampules and vials. In some embodiments formulations can be presented in single or multi-chambered pre-filled syringes (e.g., liquid syringes, lysosyringes). Solutions and suspensions can be prepared from sterile powders, granules, and tablets of the kind previously described.

Also provided are kits comprising the polypeptides or a nucleic acid encoding a polypeptide of the invention of the invention. In one embodiment provided are kits for producing a single dose administration unit. The kit comprises a first container comprising a dried polypeptide or a nucleic acid encoding a polypeptide of the invention and a second container having an aqueous reconstitution formula. In certain embodiments one container comprises a single chamber pre-filled syringe. In other embodiments the containers are encompassed as a multi-chambered pre-filled syringe VII. Exemplification The following examples are offered to illustrate, but not to limit the claimed invention.

EXAMPLE 1

Protease-Resistant Angptl3 Peptide Constructs

Various N-terminal truncation mutants were constructed to remove O-linked glycosylations and facilitate biophysical protein characterization. To identify protease-resistant peptides, amino acid substitutions were introduced into various positions of human Angptl3 peptide fragments corresponding to the C-terminal region of the peptide. FIG. 1 shows positions of mutations in the human Angptl3. Constructs were initially prepared with His tags. The mutant proteins were: 225-460 K423Q (225KQ), 225-460 S424T (225ST), 226-460 K423Q (226KQ), 226-460 K423S (226KS), 228-460 K423Q (228KQ), 228-460 S424T (228ST), 233-460 K423Q (233KQ), 233-460 K423S (233KS), 241-460 K423Q (241KQ), 241-460 K423S (241KS), 242-460 K423Q (242KQ), and 242-460 K423S (242KS).

His-tagged proteins were expressed in HEK Freestyle™ cells and purified by Ni-NTA column chromatography. Tag-less C-terminal constructs were also cloned, purified by previously described method (Gonzalez R et al PNAS 2010). Briefly, target protein with signal sequence (1-16) was cloned in a mammalian expression vector with cytomegalovirus promoter. At 96 h after DNA/PEI transfection in HEK 293 Freestyle (Invitrogen), media containing secreted target protein were harvested and purified by HiTrap SP column (GE Healthcare). Protein was eluted between 50 mM MES (pH 6.0), 125 mM NaCl to 50 mM MES (pH 6.0), 150 mM NaCl. SDS-PAGE confirmed that the purified protein was at least 95% pure Protease-resistance was assessed as follows. Limited trypsinolysis was performed by incubating 10 ng of each prepared protein with trypsin at mass ratio of 8000:1 (Protein:Trypsin) for 1 h r at room temperature. The trypsinolysis reaction was then quenched by addition of acetic acid to bring the reaction to pH 3.0, and quenched samples were analyzed by LC/MS. A 5 min RP HPLC peak corresponding to the mass of the C-terminal 43 amino acids (5424-E460) was evident for the respective wild type protein constructs. The clip site was at the same site, i.e., between K423 and S424, as observed during full length wild type ANGPLT3 protein production. This peak was absent when the Lys at the clip site was mutated to Gln. Each of peptide constructs 225KQ, 228KQ, 233KQ, 233KS, 241KQ, and 242KQ; and the wildtype 225 peptide were prepared and analyzed. The peak corresponding to the mass of the C-terminal 43 amino acids was absent when the Lys at the clip site was mutated to Gln or Ser for each of the constructs.

EXAMPLE 2

Integrin Binding Assays $\alpha V\beta 3$ Integrin Prepared peptides 225KQ, 228KQ, 233KQ, 241KQ and 242KQ were tested in vitro for binding to $\alpha V\beta 3$ integrin. Briefly, Maxisorp plates were coated with 2 μg/ml Integrin $\alpha V\beta 3$, and various concentrations of polypeptide construct (indicated) were added. Bound peptide was detected by the addition of Anti-ANGPTL3 mAb followed by horseradish peroxidase-conjugated Goat anti-Mouse IgG antibody. All tested peptides retained or improved integrin binding capacity. $EC_{50}$ for each were determined from the binding data, and results are shown in TABLE 2.

$\alpha 5\beta 1$ Integrin Prepared peptides 225KQ, 228KQ, 233KQ, 241KQ and 242KQ were tested in vitro for binding to $\alpha 5\beta 1$ integrin. Plates were coated with 2 μg/ml as described above but with Integrin $\alpha 5\beta 1$, and various concentrations of polypeptide construct (indicated) were added, and detection carried out as described above. All tested peptides retained or improved integrin binding capacity.

$EC_{50}$ for each were determined from the binding data, and results are shown in TABLE 2.

TABLE 2

In vitro binding of ANGPTL3 and engineered polypeptide constructs to Integrins

| | α5β1 integrin $EC_{50}$ | αVβ3 integrin $EC_{50}$ |
|---|---|---|
| WT | 3.054 | 3.245 |
| 242KQ | 1.566 | 3.076 |
| 241KQ | 2.693 | 4.032 |
| 233KQ | 13.83 | 6.636 |
| 228KQ | 4.26 | 4.051 |
| 225KQ | 19.89 | 11.18 |

EXAMPLE 3

Functional Analysis of Constructs

Chondrogenesis. Peptide constructs were evaluated in functional assays to assess chondrogenesis activity.

Figure 2A:
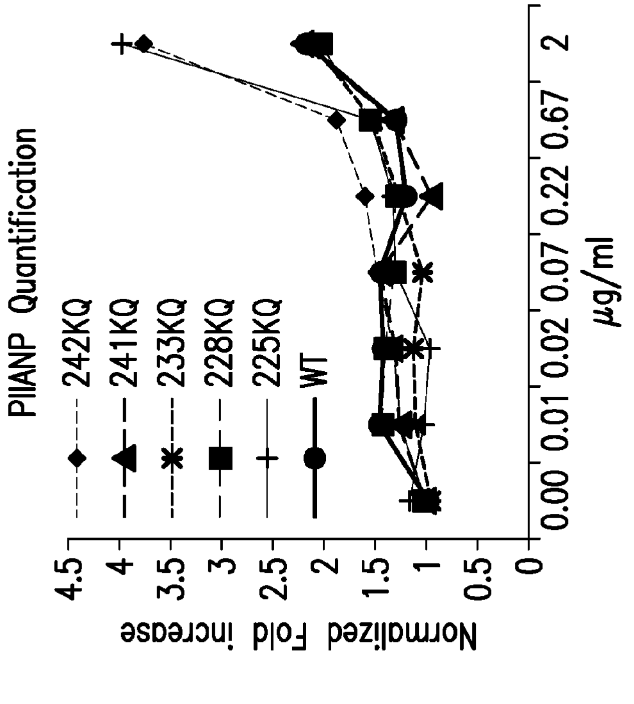
FIG. 2 depicts graphical representation of expression of cartilage specific proteins in the presence or absence of ANGPTL3 and mutant constructs. Fixed cells were stained for-(2A) Pro-collagen Type 2A (PIIANP) or (2B) Type II collagen to determine the % of cells differentiating into chondrocytes following treatment as described (quantitated by IXU high throughput imaging).
Figure 2B:
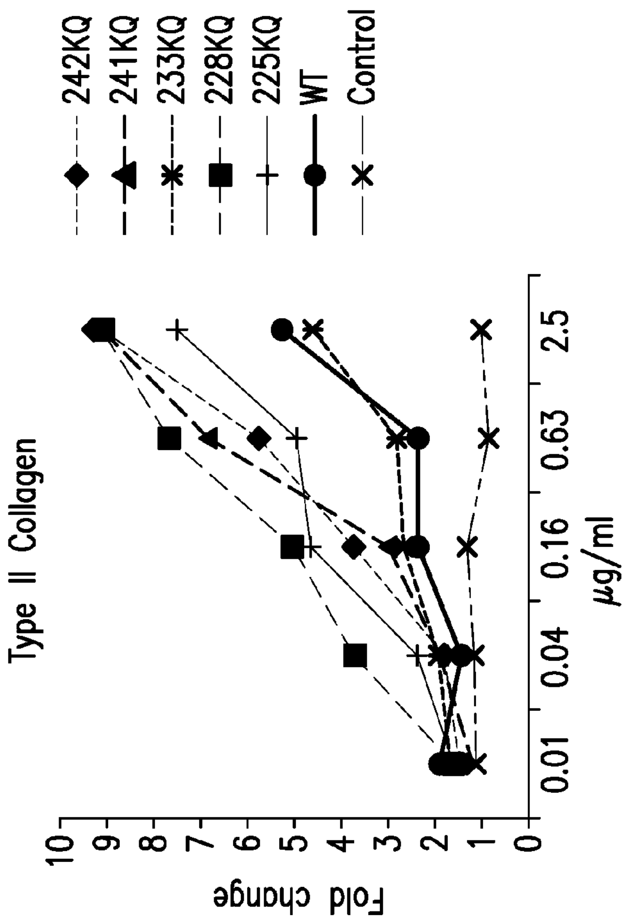

Cell-based 2D chondrogenesis was induced in vitro and assessed as described previously in Johnson, K., et al., (2012) *Science* 336, 717. Briefly, primary human bone marrow derived mesenchymal stem cells (hMSCs) were plated in growth media then subsequently changed to a chondrogenic stimulation media with and without constructs, and cultured for 7 or 14 days. Cells were then fixed with formaldehyde, washed and then stained using standard immuno-cytochemical techniques to detect primary cartilage proteins Pro-collagen Type 2A (PIIANP) and Type II collagen. Immuno-fluorescence for each protein detected was quantified through high content imaging (Image Express Ultra) and as described previously. Results are exemplified in FIG. 2 for control (cells stimulated without construct, diluent alone), WT wild type C-terminal (225-460) ANGPTL3 or mutant constructs. Similar results were seen with experiments using each of 225WT, 225KQ, 226KQ, 228KQ, 233KQ, 241KQ and 242KQ constructs.

Figure 3:
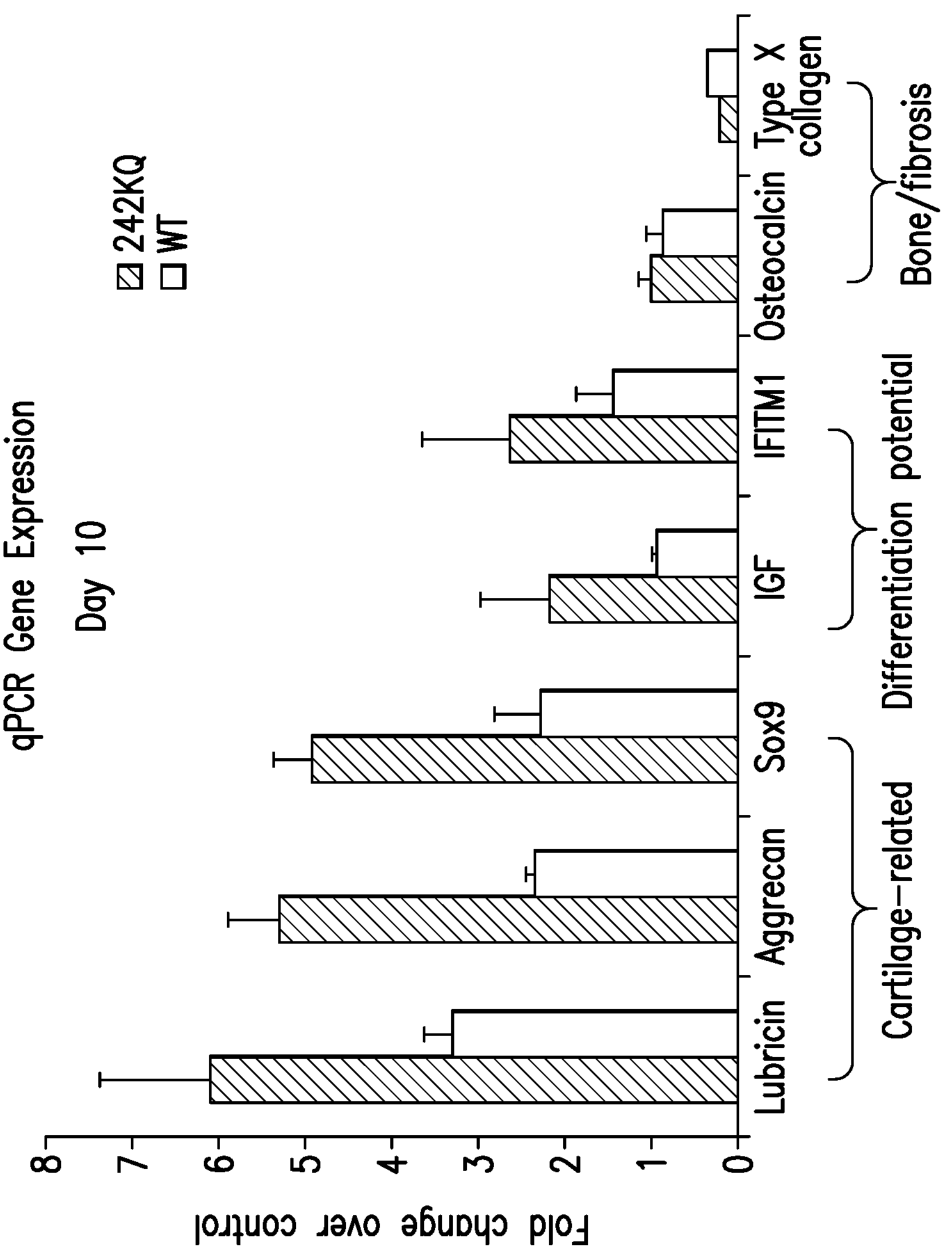
FIG. 3 is a graphical representation showing an increase in expression of cartilage specific proteins in the presence of ANGPTL3 or mutant constructs. Cells were evaluated using qRT-PCR to measure RNA expression for cartilage specific proteins following treatment as described.

RNA expression analysis was also used to evaluate expression of cartilage specific proteins. Briefly, qRT-PCR hMSCs were grown in pellet culture ($1\times10^6$ cells/pellet) for 3, 7, 10, 21 days in serum free DMEM, 1×ITS plus constructs (as indicated). Media was replaced every 3 days. Lubricin, Aggrecan, Sox9, IGF1, IFITM1, Osteocalcin and type X collagen mRNA expression were quantified using Roche LightCycler (data pooled from 3 experiments performed in duplicate (n=6)). FIG. 3 represents expression data at—Day 10 for 242KQ and 225WT. Gene expression data was similar for all genes at days 3, 7 and 21.

Chondroprotection. Peptide constructs were evaluated in functional assays to assess chondroprotective activity.

Figure 4B:
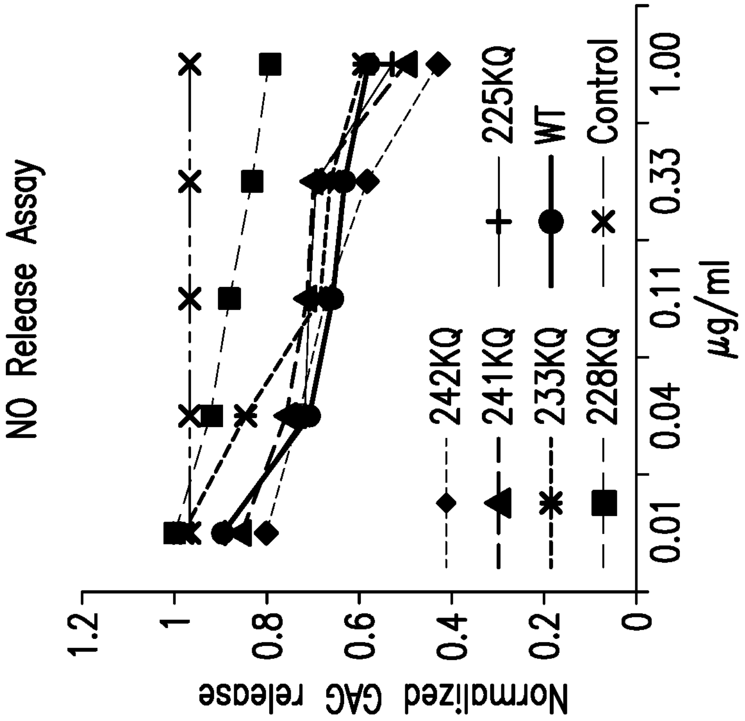
FIG. 4 depicts graphical representations of chondro-protective activity of ANGPTL3 and mutant constructs. (4A) Glycosaminoglycan (GAG) release, an indicator of matrix damage, was inhibited with increasing amount of ANGPTL3 and mutant constructs. Ex vivo GAG release (an indicator of matrix damage) inhibition assays were performed using bovine cartilage treated in the presence or absence of constructs as described. (4B) NO release was inhibited with increasing amount of ANGPTL3 and mutant constructs. Chondrocytes were treated in the presence or absence of constructs as described followed by Greiss reaction assays to determine the inhibition of NO release as an indicator of chondro-protection.
Figure 4A:
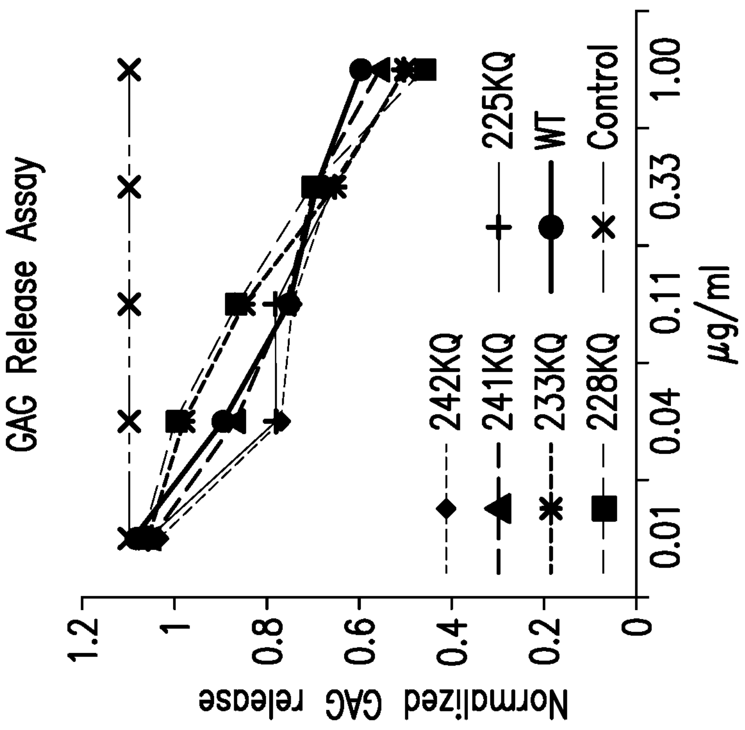

An ex vivo glycosaminoglycan (GAG) release inhibition assay (an indicator of matrix damage) was performed as described in Johnson, K., et al., (2012) *Science* 336, 717-721. Briefly, bovine cartilage was isolated, punched into symmetric circles and put into organ culture. Slices were treated for 48 hours with 20 ng/ml TNFα and 10 ng/ml OSM (inflammatory mediators) to induce degradation of the cartilage matrix in the presence or absence of protein constructs to identify percent inhibition of glycosaminoglycan (GAG) release. Results shown in FIG. 4A depict data pooled from 4 donors, n=12 with the constructs as indicated and WT 425-460.

An in vitro nitric oxide (NO) inhibition assay (an indicator of chondro-protection) was performed as described in Johnson, K., et al., (2012) *Science* 336, 717-721. Briefly, primary chondrocytes were treated for 48 hrs with protein constructs as indicated. Greiss reaction was performed, to determine the effect of constructs on inhibition of NO release as Results shown in FIG. 4B depict results with the constructs 225WT and each of the 225KQ, 228KQ, 233KQ, 241KQ, and 242KQ constructs.

Figure 5:
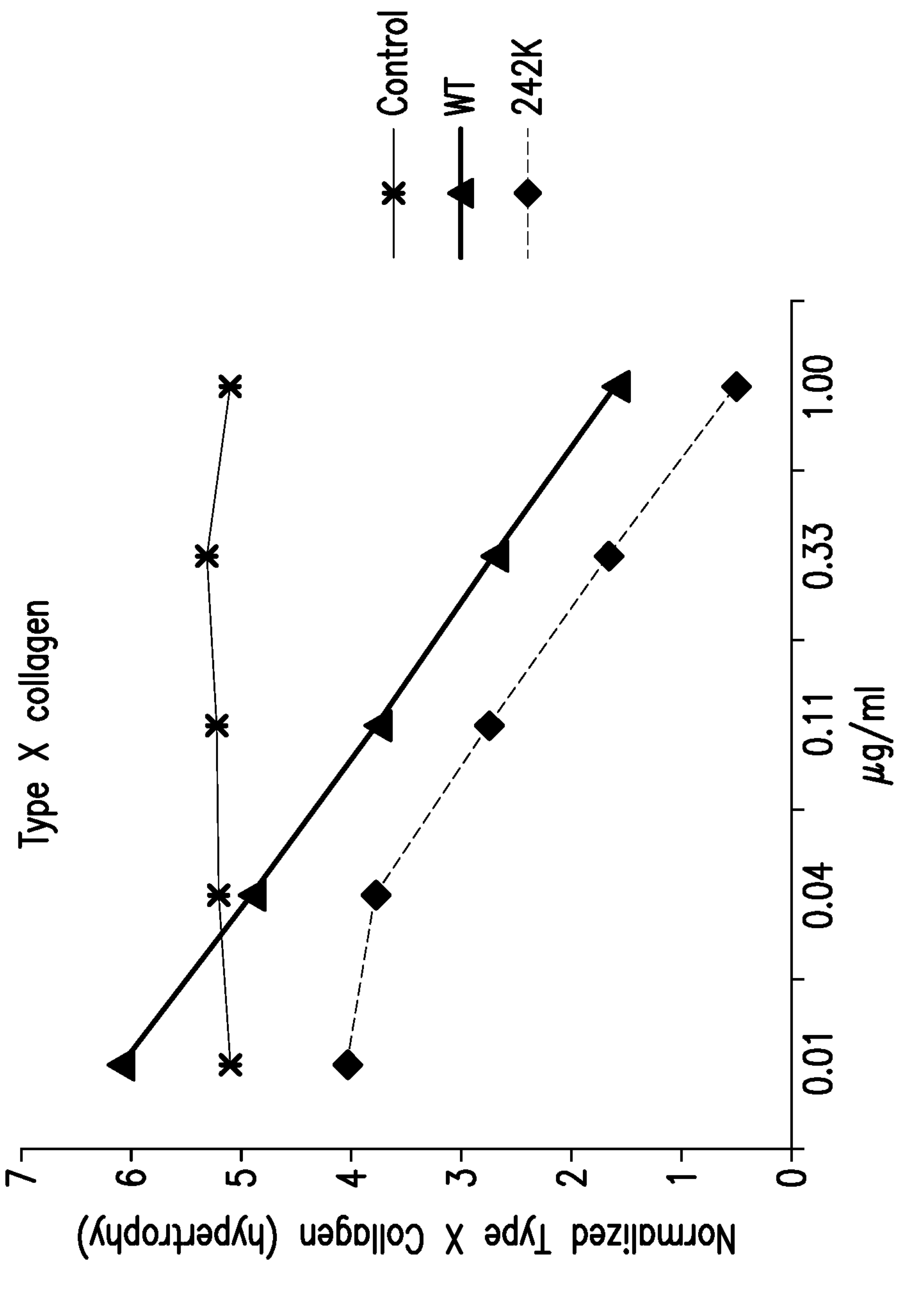
FIG. 5 depicts a graphical representation showing an inhibition of type X collagen expression (an indicator of fibrotic cartilage formation activity) in the presence of ANGPTL3 and mutant constructs under hypertrophic conditions. Primary chondrocytes were treated in the presence of absence of constructs under hypertrophic conditions as described, followed by determination of type X collagen expression, assessed by immunofluorescence, as a measurement of formation of fibrotic and hypertrophic cartilage/chondrocyte differentiation.

Inhibition of Fibrotic Cartilage Formation. Primary human articular chondrocytes were cultured as described above with the addition of ascorbic acid and the presence or absence of constructs (indicated) for 14 days to induce hypertrophy and type X collagen expression was assessed by immunoflurescence. Results shown in FIG. 5 depict data with constructs 225WT or 242KQ as indicated. The presence of wild type or active constructs confer an inhibitory effect on formation of fibrotic cartilage under hypertrophic conditions, as detected by expression of type X collagen.

EXAMPLE 4

In Vivo Analysis of Constructs

Figure 6A:
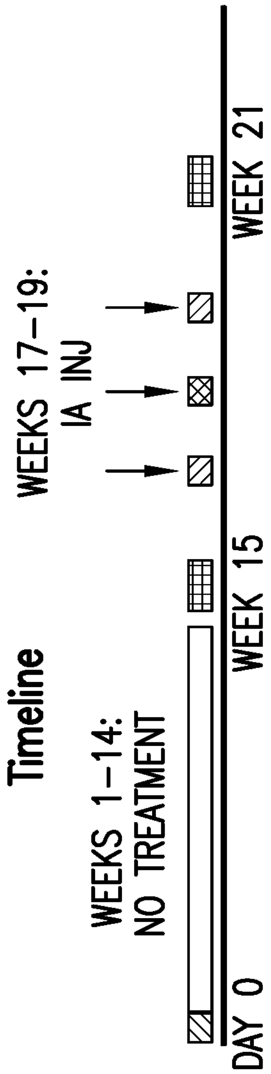
FIG. 6 depicts a schematic representation of the dosing paradigm followed by a graphical representation of the improvement in joint severity after treatment with mouse ANGPTL3 (17-460).
Figure 6B:
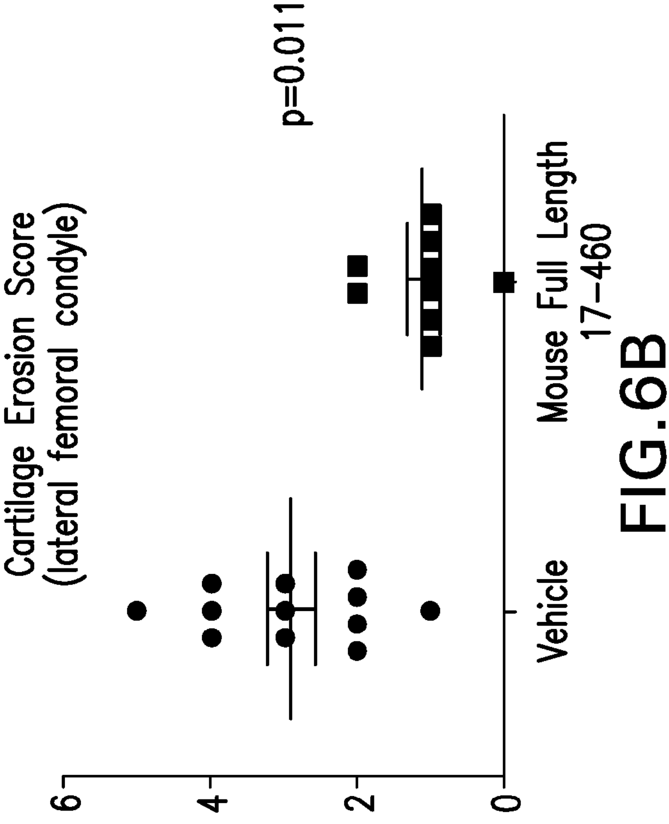

Mouse Acute Injury Surgical Model. Surgical transection of the anterior cruciate ligament (ACL), medial meniscal tibial ligament (MMTL), and medial collateral ligament (MCL) of the right knee from C57BL/6 mice (n=12/group) was performed to induce instability in the knee joint and thus lead to an OA phenotype, adapted from the previously described model Glasson, S. S., et al., *Osteoarthritis Cartilage* 15, 1061 (2007). To evaluate a potential therapeutic benefit of ANGPTL3 treatment, 15 weeks following surgery, mice were dosed intra-articularly as indicated in FIG. 6*a* once/per week on weeks 17-19: mANGPTL3 dose=200 ng/knee. Quantitative assessments of the tibial plateau were made on a 0-4 scale, 0 being normal and 5 being severe osteoarthritis (full thickness disruption of the cartilage). Two sections from each mouse were blindly graded by 2 independent observers (FIG. 6B).

Figure 7A:
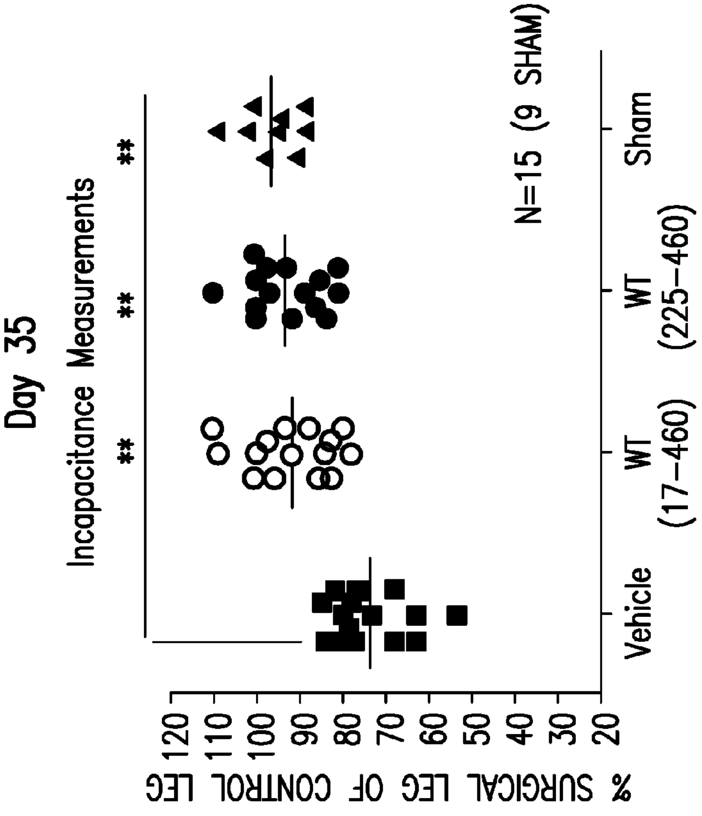
FIG. 7 is a graphical representation of the incapacitance measurement (an indicator of pain) in mice following surgical induction of cartilage damage and subsequent treatment with ANGPTL3 constructs once weekly for three weeks (beginning on day 7). Measurements were performed on day 35 and 56 following surgery.
Figure 7B:
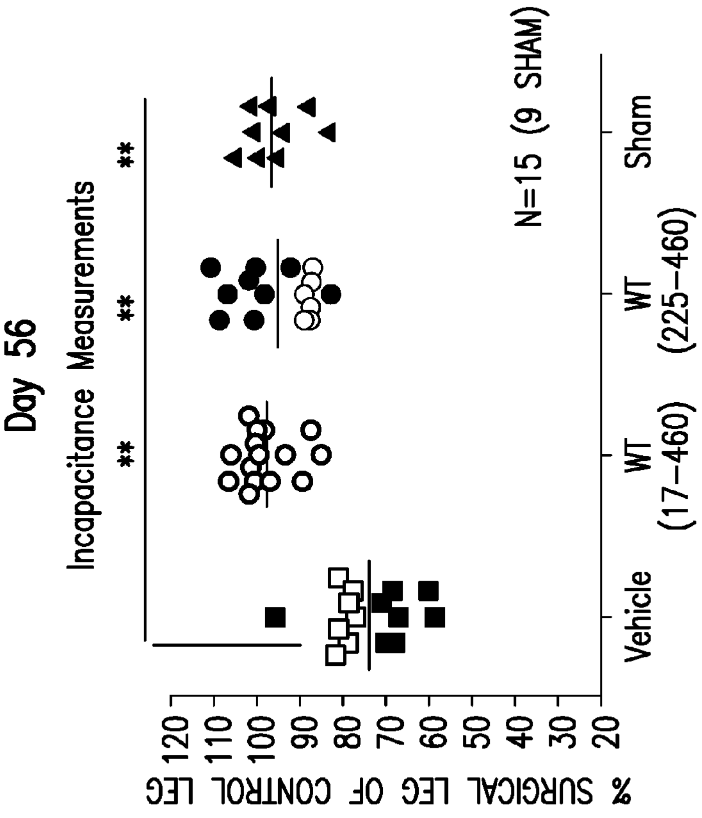

Alleviation of osteoarthritis induced pain for animals was measured by incapacitance testing, or determining the percentage of time the mouse stood on a surgically treated leg vs the non-treated leg using an incapacitance monitoring device. FIG. 7 depicts results of readouts, representing pain response on days 35 and 56 after surgery were reported as a % weight bearing on the surgical limb versus the non surgical limb. Treatment depicts results of animals dosed as described above with full length murine ANGPTL3 (WT17-460) or C-terminal human ANGPTL3 (WT225-460).

Figure 8:
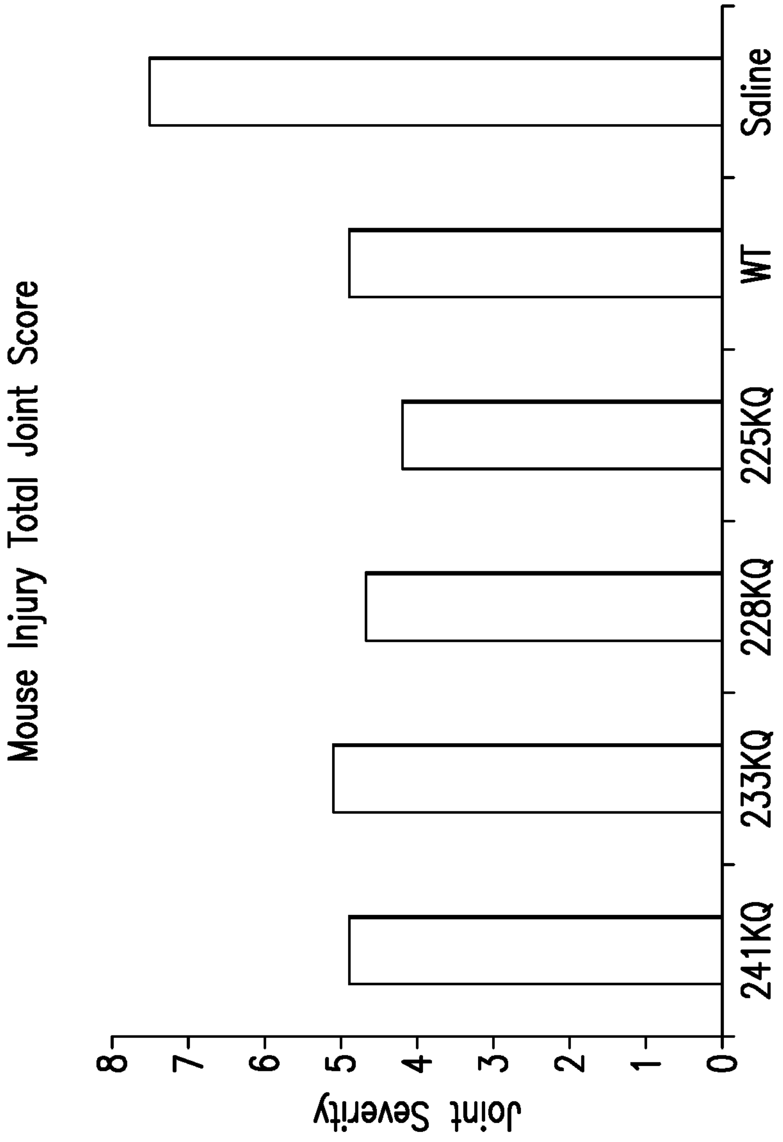
FIG. 8 is a graphical representation of the total joint severity score and improvement in severity to cartilage damage induced by collagenase in mice following 3 once weekly treatments (days 7, 14 and 21) of ANGPTL3 constructs (indicated).

Mouse Chronic OA Model (Collagenase VII Induced) Another widely used animal model of osteoarthritis, the collagenase VII-induced chronic joint injury model, was used to evaluate in vivo efficacy of constructs. The model and evaluation was performed as previously described. See van der Kraan, P. M., et al., *Am. J. Pathol.* 135, 1001 (1989); and Johnson, K., et al., *Science* 336, 717 (2012). Briefly, a three (3) day period of inflammation is followed by collagenase induced destabilization of the joint, resulting in mild to moderate cartilage destruction. Intra-articular administration of constructs was carried out following induction in the knee once/week for three weeks, beginning 3 weeks after addition of collagenase VII. Forty (42) days following treatment, joints were collected and sectioned. Histological joint severity scoring of femoral and tibial plateau allowed quantification of the tissue repair. The severity of the joint score was determined through histological scoring as described above. FIG. 8 depicts repair with 225WT, 225KQ, 228KQ, 233KQ, and 241KQ constructs. To confirm the presence of protein in the joint (long term intra-articular retention), tissue was fixed and stained for the presence of the WT protein construct through immunohistochemistry. Analysis confirmed the presence of protein indicating intra-articular retention of ANGPTL3 (with no effects seen on lipid/triglyceride, assessed using a standard metabolic panel, data not shown.)

Histological analysis and grading on Safranin O stained sections of the medial tibial plateau (for detection of proteoglycan at the injury site, as described above) revealed regeneration in cartilage matrix (data not shown). Qualitative analysis confirmed replacement of proteoglycans similar to levels seen in a naïve mouse, while vehicle controls did not show similar replacement. Tissue sections were also stained as described above for type II collagen 8 weeks following injection of the injury. Qualitative analyses confirmed an increase of type II collagen in joints treated with construct similar to levels seen in a naïve mouse; while vehicle treated controls did not show similar increase (data not shown).

Rat Meniscal Tear Model A rat surgical injury model was also used to evaluate in vivo efficacy of constructs. The model and evaluation was performed as previously described Gerwin N. et al. *Osteoarthritis Cartilage*. Suppl 3: S24 (2010). Briefly, skin was shaven over a knee joint and the medial collateral ligament (MCL) was isolated through an incision, and the MCL was stabilized and a distal cut of the meniscus made using a scalpel. On weeks 1, 2 and 3 following surgery protein construct or vehicle control was injected intra-articularly, then joints were collected and sectioned at 4 and 6 weeks after surgery. Histological joint severity scoring of femoral and tibial plateau were performed for quantification of the tissue repair as described above. Data is shown for the 6 weeks analyses.

Figure 9A:
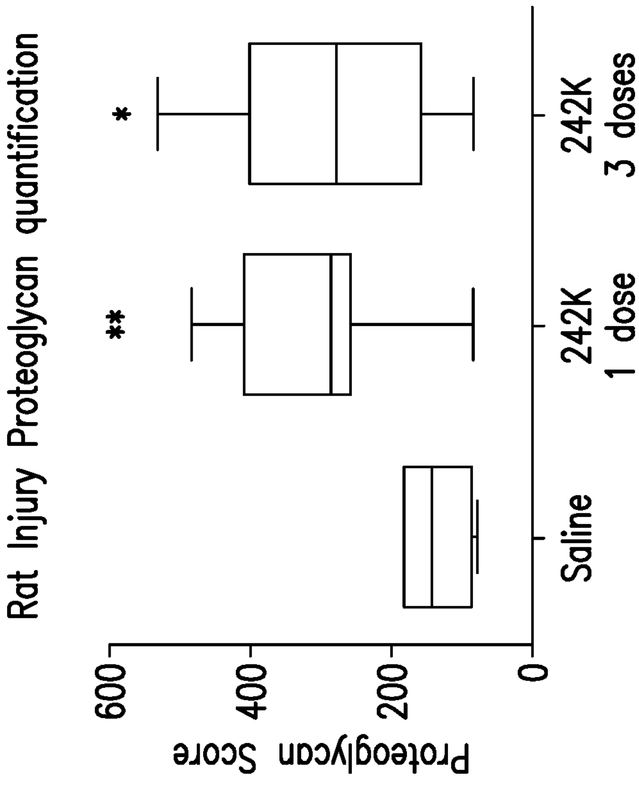
FIG. 9A is a graphical representation of the proteoglycan content in joints and FIG. 9B is a graphical representation of the femoral joint severity score. Results illustrate improvement to cartilage damage induced by surgical severing of the meniscus in rats following 3 once weekly treatments (days 7, 14 and 21) of ANGPTL3 constructs (indicated).
Figure 9B:
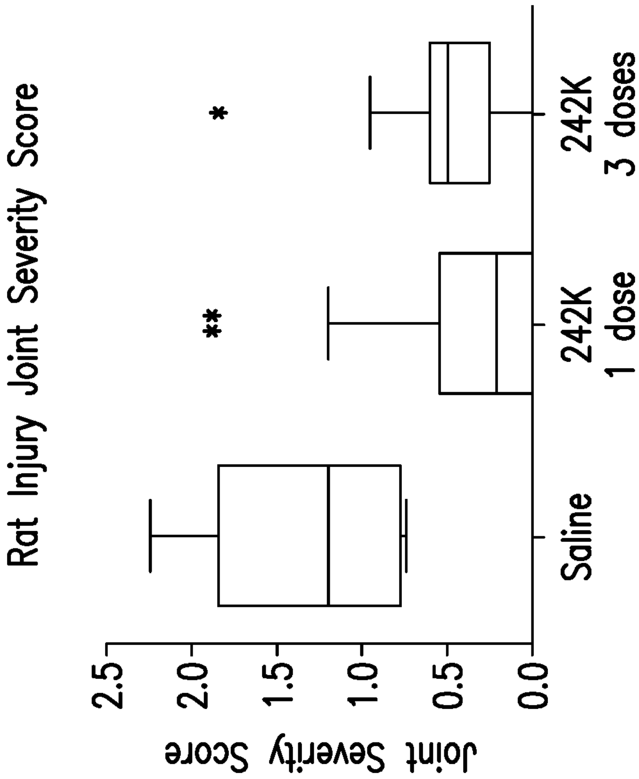

Healthy hyaline cartilage replaced damage following treatment. Histological analysis and grading of the lateral tibial plateau of safranin O stained cartilage were performed as described above and quantified Results demonstrated animals treated with 242KQ construct revealed regeneration in cartilage matrix and replacement of proteoglycans similar to levels seen in a naïve rat, while vehicle controls did not show similar replacement. See FIG. 9. Similar results were seen with 225WT.

TABLE 3

| Persistence of $^{124}$I 242 KQ | | | | | | | |
|---|---|---|---|---|---|---|---|
| Route | Dose (µg) | $C_{max}$ (µg/mL) | $AUC_{0\text{-}inf}$ (hr*µg/mL) | CL (mL/h) | Vss (mL) | MRT (h) | $T_{1/2}$ (h) |
| IV | 164.2 | 129.3 | 22.1 | 7.4 | 53.4 | 7.2 | 12.4 |
| IA | 38.3 | 0.2 | 1.9 | — | — | 17.3 | 7.2 |

Long term retention of 242KQ following intravenous and intra-articular injection into rat knees was determined through $^{124}$I labeling of protein and administration followed by PET/uCT imaging to monitor retention. See, Gerwin, N., et al. (2006) *Advanced drug delivery reviews* 58, 226-242. The mean residence time (MRT) after IA injection of 242KQ into the joint was determined to be ~17.3 h which is significantly increased over the standard 2-3 h reported (See TABLE 3)

Figure 10:
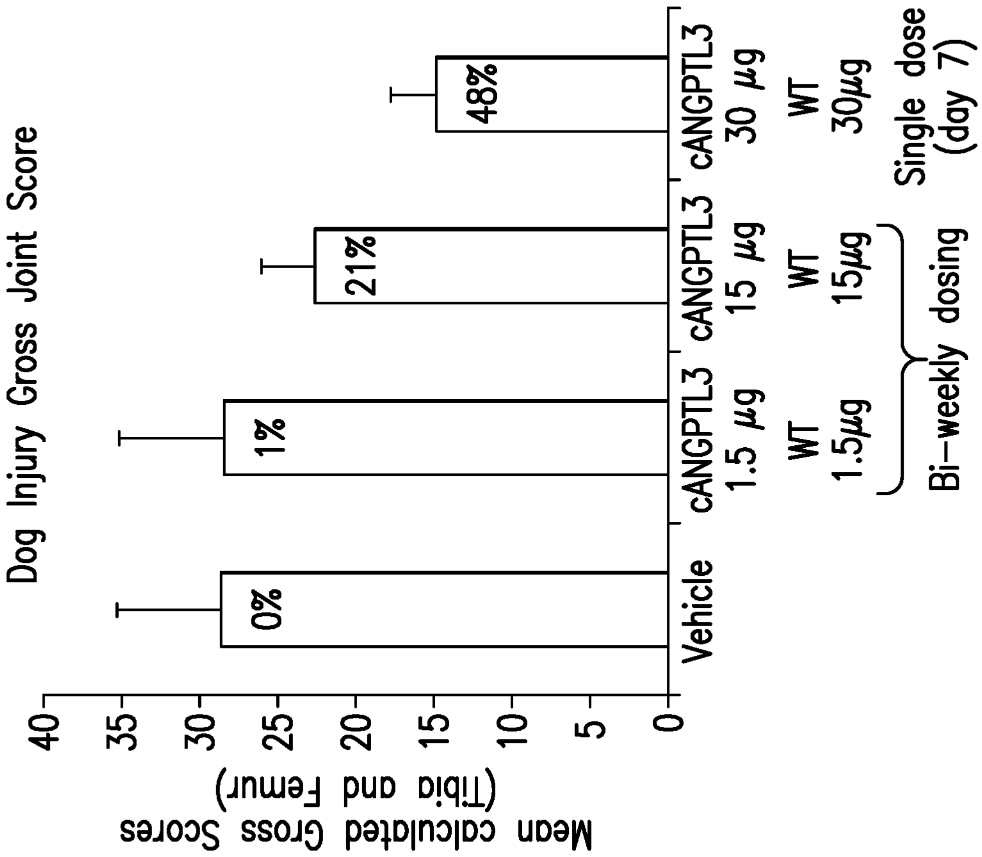
FIG. 10 is a graphical representation of the total gross severity score to illustrate improvement of cartilage damage induced by surgical disruption of the medial meniscus in dogs following biweekly dosing beginning on day 4 or a single dose given on day 7 only.

Dog Partial Menisectomy Joint Injury Model We also evaluated ANGPTL3 activity in a canine joint injury model. The model was performed and evaluations performed as described in Connor, J. R., et al., *Osteoarthritis and cartilage/OARS, Osteoarthritis Research Society* 17, 1236-1243 (2009). Briefly, skin was shaven over a knee joint and the medial collateral ligament (MCL) was isolated through an incision, and the MCL was stabilized and a distal cut of the meniscus made using a scalpel. Four (4) days following surgery, twice weekly dosing or a single dose of the protein construct on day 7 or vehicle control was injected intra-articularly. Dogs were euthanized and the knees were subjected to histological, sectioning and grading as described above for the rat and mouse experiments. FIG. 10 depicts the Total gross score of the repair associated with treatment of ANGPTL3.

It is understood that the examples and embodiments described herein are for illustrative purposes and that various modifications or changes in light thereof will be suggested to persons skilled in the art and are to be included within the spirit and purview of this application and scope of the appended claims.

SEQUENCES

| SEQ ID | Construct | Sequence |
|---|---|---|
| 1 | Human ANGPTL3 | MFTIKLLLFIVPLVISSRIDQDNSSFDSLSPEPKSRFAMLDDVKILANGLLQLGH<br>GLKDFVHKTKGQINDIFQKLNIFDQSFYDLSLQTSEIKEEEKELRRTTYKLQVKN<br>EEVKNMSLELNSKLESLLEEKILLQQKVKYLEEQLTNLIQNQPETPEHPEVTSLK<br>TFVEKQDNSIKDLLQTVEDQYKQLNQQHSQIKEIENQLRRTSIQEPTEISLSSKP<br>RAPRTTPFLQLNEIRNVKHDGIPAECTTIYNRGEHTSGMYAIRPSNSQVFHVYCD<br>VISGSPWTLIQHRIDGSQNFNETWENYKYGFGRLDGEFWLGLEKIYSIVKQSNYV<br>LRIELEDWKDNKHYIEYSFYLGNHETNYTLHLVAITGNVPNAIPENKDLVFSTWD<br>HKAKGHFNCPEGYSGGWWWHDECGENNLNGKYNKPRAKSKPERRRGLSWKSQNGR<br>LYSIKSTKMLIHPTDSESFE |
| 2 | Human ANGPTL3 REFSEQ | ttccagaagaaaacagttccacgttgcttgaaattgaaaatcaagataaaaatgt<br>tcacaattaagctccttctttttattgttcctctagttatttcctccagaattga<br>tcaagacaattcatcatttgattctctatctccagagccaaaatcaagatttgct<br>atgttagacgatgtaaaaattttagccaatggcctccttcagttgggacatggtc<br>ttaaagactttgtccataagacgaagggccaaattaatgacatatttcaaaaact<br>caacatatttgatcagtctttttatgatctatcgctgcaaaccagtgaaatcaaa<br>gaagaagaaaaggaactgagaagaactacatataaactacaagtcaaaaatgaag<br>aggtaaagaatatgtcacttgaactcaactcaaaacttgaaagcctcctagaaga<br>aaaaattctacttcaacaaaaagtgaaatatttagaagagcaactaactaactta<br>attcaaaatcaacctgaaactccagaacacccagaagtaacttcacttaaaactt<br>ttgtagaaaaacaagataatagcatcaaagaccttctccagaccgtggaagacca<br>atataaacaattaaaccaacagcatagtcaaataaaagaaatagaaaatcagctc |

-continued

| SEQ ID | Construct | Sequence |
|---|---|---|
| | | agaaggactagtattcaagaacccacagaaatttctctatcttccaagccaagag<br>caccaagaactactccctttcttcagttgaatgaaataagaaatgtaaaacatga<br>tggcattcctgctgaatgtaccaccatttataacagaggtgaacatacaagtggc<br>atgtatgccatcagacccagcaactctcaagtttttcatgtctactgtgatgtta<br>tatcaggtagtccatggacattaattcaacatcgaatagatggatcacaaaactt<br>caatgaaacgtgggagaactacaaatatggttttgggaggcttgatggagaattt<br>tggttgggcctagagaagatatactccatagtgaagcaatctaattatgttttac<br>gaattgagttggaagactggaaagacaacaaacattatattgaatattcttttta<br>cttgggaaatcacgaaaccaactatacgctacatctagttgcgattactggcaat<br>gtccccaatgcaatcccggaaaacaaagatttggtgttttctacttgggatcaca<br>aagcaaaaggacacttcaactgtccagagggttattcaggaggctggtggtggca<br>tgatgagtgtggagaaaacaacctaaatggtaaatataacaaaccaagagcaaaa<br>tctaagccagagaggagaagaggattatcttggaagtctcaaaatggaaggttat<br>actctataaaatcaaccaaaatgttgatccatccaacagattcagaaagctttga<br>atgaactgaggcaaatttaaaaggcaataatttaaacattaacctcattccaagt<br>taatgtggtctaataatctggtattaaatccttaagagaaagcttgagaaataga<br>tttttttttatcttaaagtcactgtctatttaagattaaacatacaatcacataac<br>cttaaagaataccgtttacatttctcaatcaaaattcttataatactatttgttt<br>taaattttgtgatgtgggaatcaattttagatggtcacaatctagattataatca<br>ataggtgaacttattaaataacttttctaaataaaaaatttagagacttttattt<br>taaaaggcatcatatgagctaatatcacaactttcccagtttaaaaaactagtac<br>tcttgttaaaactctaaacttgactaaatacagaggactggtaattgtacagttc<br>ttaaatgttgtagtattaatttcaaaactaaaaatcgtcagcacagagtatgtgt<br>aaaaatctgtaatacaaatttttaaactgatgcttcattttgctacaaaataatt<br>tggagtaaatgtttgatatgatttatttatgaaacctaatgaagcagaattaaat<br>actgtattaaaataagttcgctgtctttaaacaaatggagatgactactaagtca<br>cattgactttaacatgaggtatcactataccttatt |
| 3 | Murine ANGPTL3 | MHTIKLFLFVVPLVIASRVDPDLSSFDSAPSEPKSRFAMLDDVKILANGLLQLGH<br>GLKDFVHKTKGQINDIFQKLNIFDQSFYDLSLRTNEIKEEEKELRRTTSTLQVKN<br>EEVKNMSVELNSKLESLLEEKTALQHKVRALEEQLTNLILSPAGAQEHPEVTSLK<br>SFVEQQDNSIRELLQSVEEQYKQLSQQHMQIKEIEKQLRKTGIQEPSENSLSSKS<br>RAPRTTPPLQLNETENTEQDDLPADCSAVYNRGEHTSGVYTIKPRNSQGFNVYCD<br>TQSGSPWTLIQHRKDGSQDFNETWENYEKGFGRLDGEFWLGLEKIYAIVQQSNYI<br>LRLELQDWKDSKHYVEYSFHLGSHETNYTLHVAEIAGNIPGALPEHTDLMFSTWN<br>HRAKGQLYCPESYSGGWWWNDICGENNLNGKYNKPRTKSRPERRRGIYWRPQSRK<br>LYAIKSSKMMLQPTT |
| 4 | Canine ANGPTL3 | MYTIKLFLFIIPLVISSKIDRDYSSYDSVSPEPKSRFAMLDDVKILANGLLQLGH<br>GLKDFVHKTKGQINDIFQKLNIFDQSFYDLSLQTNEIKEEEKELRRTTSKLQVKN<br>EEVKNMSLELNSKVESLLEEKILLQQKVRYLEKQLTSLIKNQPEIQEHPEVTSLK<br>TFVEQQDNSIKDLLQTVEEQYRQLNQQHSQIKEIENQLRNVIQESTENSLSSKPR<br>APRTTPFLHLNETKNVEHNDIPANCTTIYNRGEHTSGIYSIRPSNSQVFNVYCDV<br>KSGSSWTLIQHRIDGSQNFNETWENYRYGFGRLDGEFWLGLEKIYSIVKQSNYIL<br>RIELEDWNDNKHYIEYFFHLGNHETNYTLHLVEITGNILNALPEHKDLVFSTWDH<br>KAKGHVNCPESYSGGWWWHNVCGENNLNGKYNKQRAKTKPERRRGLYWKSQNGRL<br>YSIKSTKMLIHPIDSESSE |
| 5 | Equine ANGPTL3 | MYTIKLFLVIAPLVISSRIDQDYSSLDSIPPEPKSRFAMLDDVKILANGLLQLGH<br>GLKDFVHKTKGQINDIFQKLNIFDQSFYALSLQTNEIKEEEKELRRTTSKLQVKN<br>EEVKNMSLELNSKLESLLEEKSLLQQKVKYLEEQLTKLIKNQPEIQEHPEVTSLK<br>TFVEQQDNSIKDLLQTMEEQYRQLNQQHSQIKEIENQLRRTGIQESTENSLSSKP<br>RAPRTTPSFHLNETKDVEHDDFPADCTTIYNRGEHTSGIYSIKPSNSQVFNVYCD<br>VISGSSWILIQRRIDGSQNFNETWQNYKYGFGRLDFEFWLGLEKIYSIVKRSNYI<br>LRIELEDWKDNKHTIEYSFHLGNHETNYTLHLVEITGNVPNALPEHKDLVFSTWD<br>HKAKGQLNCLESYSGGWWWHDVCGGDNPNGKYNKPRSKTKPERRRGICWKSQNGR<br>LYTIKSTKMLIHPIDSESFELRQIKKPMN |
| 6 | Bovine ANGPTL3 | MYTIKLFLIIAPLVISSRTDQDYTSLDSISPEPKSRFAMLDDVKILANGLLQLGH<br>GLKDFVHKTKGQINDIFQKLNIFDQSFYDLSLQTNEIKEEEKELRRATSKLQVKN<br>EEVKNMSLELDSKLESLLEEKILLQQKVRYLEDQLTDLIKNQPQIQEYLEVTSLK<br>TLVEQQDNSIKDLLQIVEEQYRQLNQQQSQIKEIENQLRRTGIKESTEISLSSKP<br>RAPRTTPSFHSNETKNVEHDDIPADCTIIYNQGKHTSGIYSIRPSNSQVFNVYCD<br>VKSGSSWTLIQHRIDGSQNFNETWENYKYGFGRLDGEFWLGLEKIYSIVMQSNYI<br>LRIELEDWKDKYYTEYSFHLGDHETNYTLHLAEISGNGPKAFPEHKDLMFSTWDH<br>KAKGHFNCPESNSGGWWYHDVCGENNLNGKYNKPKAKAKPERKEGICWKSQDGRL<br>YSIKATKMLIHPSDSENSE |
| 7 | 207-455WT | IQEPTEISLSSKPRAPRTTPFLQLNEIRNVKHDGIPAECTTIYNRGEHTSGMYAI<br>RPSNSQVFHVYCDVISGSPWTLIQHRIDGSQNFNETWENYKYGFGRLDGEFWLGL<br>EKIYSIVKQSNYVLRIELEDWKDNKHYIEYSFYLGNHETNYTLHLVAITGNVPNA<br>IPENKDLVFSTWDHKAKGHFNCPEGYSGGWWWHDECGENNLNGKYNKPRAKSKPE<br>RRRGLSWKSQNGRLYSIKSTKMLIHPTD |
| 8 | 225-455WT | TTPFLQLNEIRNVKHDGIPAECTTIYNRGEHTSGMYAIRPSNSQVFHVYCDVISG<br>SPWTLIQHRIDGSQNFNETWENYKYGFGRLDGEFWLGLEKIYSIVKQSNYVLRIE |

-continued

| SEQ ID | Construct | Sequence |
|---|---|---|
| | | LEDWKDNKHYIEYSFYLGNHETNYTLHLVAITGNVPNAIPENKDLVFSTWDHKAKGHFNCPEGYSGGWWWHDECGENNLNGKYNKPRAKSKPERRRGLSWKSQNGRLYSIKSTKMLIHPTD |
| 9 | 228-455WT | FLQLNEIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRAKSKPERRRGLSWKSQNGRLYSIKSTKMLIHPTD |
| 10 | 233-455WT | EIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRAKSKPERRRGLSWKSQNGRLYSIKSTKMLIHPTD |
| 11 | 241-455WT | GIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRAKSKPERRRGLSWKSQNGRLYSIKSTKMLIHPTD |
| 12 | ANGPTL3KQ | MFTIKLLLFIVPLVISSRIDQDNSSFDSLSPEPKSRFAMLDDVKILANGLLQLGHGLKDFVHKTKGQINDIFQKLNIFDQSFYDLSLQTSEIKEEEKELRRTTYKLQVKNEEVKNMSLELNSKLESLLEEKILLQQKVKYLEEQLTNLIQNQPETPEHPEVTSLKTFVEKQDNSIKDLLQTVEDQYKQLNQQHSQIKEIENQLRRTSIQEPTEISLSSKPRAPRTTPFLQLNEIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRAQSKPERRRGLSWKSQNGRLYSIKSTKMLIHPTDSESFE |
| 13 | ANGPTL3KS | MFTIKLLLFIVPLVISSRIDQDNSSFDSLSPEPKSRFAMLDDVKILANGLLQLGHGLKDFVHKTKGQINDIFQKLNIFDQSFYDLSLQTSEIKEEEKELRRTTYKLQVKNEEVKNMSLELNSKLESLLEEKILLQQKVKYLEEQLTNLIQNQPETPEHPEVTSLKTFVEKQDNSIKDLLQTVEDQYKQLNQQHSQIKEIENQLRRTSIQEPTEISLSSKPRAPRTTPFLQLNEIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRASSKPERRRGLSWKSQNGRLYSIKSTKMLIHPTDSESFE |
| 14 | 207KQ | IQEPTEISLSSKPRAPRTTPFLQLNEIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRAQSKPERRRGLSWKSQNGRLYSIKSTKMLIHPTDSESFE |
| 15 | 207KS | IQEPTEISLSSKPRAPRTTPFLQLNEIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRASSKPERRRGLSWKSQNGRLYSIKSTKMLIHPTDSESFE |
| 16 | 225KQ | TTPFLQLNEIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRAQSKPERRRGLSWKSQNGRLYSIKSTKMLIHPTDSESFE |
| 17 | 225KS | TTPFLQLNEIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRASSKPERRRGLSWKSQNGRLYSIKSTKMLIHPTDSESFE |
| 18 | 225ST | TTPFLQLNEIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRAKTKPERRRGLSWKSQNGRLYSIKSTKMLIHPTDSESFE |
| 19 | 226KQ | TPFLQLNEIRNVKHDGIPAECTTIYNRGEHTSGMYAIRPSNSQVFHVYCDVISGSPWTLIQHRIDGSQNFNETWENYKYGFGRLDGEFWLGLEKIYSIVKQSNYVLRIELEDWKDNKHYIEYSFYLGNHETNYTLHLVAITGNVPNAIPENKDLVFSTWDHKAKGHFNCPEGYSGGWWWHDECGENNLNGKYNKPRAQSKPERRRGLSWKSQNGRLYSIKSTKMLIHPTDSESFE |

-continued

| SEQ ID | Construct | Sequence |
|---|---|---|
| 20 | 226KS | TPFLQLNEIRNVKHDGIPAECTTIYNRGEHTSGMYAIRPSNSQVFHVYCDVISGS PWTLIQHRIDGSQNFNETWENYKYGFGRLDGEFWLGLEKIYSIVKQSNYVLRIEL EDWKDNKHYIEYSFYLGNHETNYTLHLVAITGNVPNAIPENKDLVFSTWDHKAKG HFNCPEGYSGGWWWHDECGENNLNGKYNKPRASSKPERRRGLSWKSQNGRLYSIK STKMLIHPTDSESFE |
| 21 | 228KQ | FLQLNEIRNVKHDGIPAECTTIYNRGEHTSGMYAIRPSNSQVFHVYCDVISGSPW TLIQHRIDGSQNFNETWENYKYGFGRLDGEFWLGLEKIYSIVKQSNYVLRIELED WKDNKHYIEYSFYLGNHETNYTLHLVAITGNVPNAIPENKDLVFSTWDHKAKGHF NCPEGYSGGWWWHDECGENNLNGKYNKPRAQSKPERRRGLSWKSQNGRLYSIKST KMLIHPTDSESFE |
| 22 | 228KS | FLQLNEIRNVKHDGIPAECTTIYNRGEHTSGMYAIRPSNSQVFHVYCDVISGSPW TLIQHRIDGSQNFNETWENYKYGFGRLDGEFWLGLEKIYSIVKQSNYVLRIELED WKDNKHYIEYSFYLGNHETNYTLHLVAITGNVPNAIPENKDLVFSTWDHKAKGHF NCPEGYSGGWWWHDECGENNLNGKYNKPRASSKPERRRGLSWKSQNGRLYSIKST KMLIHPTDSESFE |
| 23 | 228ST | FLQLNEIRNVKHDGIPAECTTIYNRGEHTSGMYAIRPSNSQVFHVYCDVISGSPW TLIQHRIDGSQNFNETWENYKYGFGRLDGEFWLGLEKIYSIVKQSNYVLRIELED WKDNKHYIEYSFYLGNHETNYTLHLVAITGNVPNAIPENKDLVFSTWDHKAKGHF NCPEGYSGGWWWHDECGENNLNGKYNKPRAKTKPERRRGLSWKSQNGRLYSIKST KMLIHPTDSESFE |
| 24 | 233KQ | EIRNVKHDGIPAECTTIYNRGEHTSGMYAIRPSNSQVFHVYCDVISGSPWTLIQH RIDGSQNFNETWENYKYGFGRLDGEFWLGLEKIYSIVKQSNYVLRIELEDWKDNK HYIEYSFYLGNHETNYTLHLVAITGNVPNAIPENKDLVFSTWDHKAKGHFNCPEG YSGGWWWHDECGENNLNGKYNKPRAQSKPERRRGLSWKSQNGRLYSIKSTKMLIH PTDSESFE |
| 25 | 233KS | EIRNVKHDGIPAECTTIYNRGEHTSGMYAIRPSNSQVFHVYCDVISGSPWTLIQH RIDGSQNFNETWENYKYGFGRLDGEFWLGLEKIYSIVKQSNYVLRIELEDWKDNK HYIEYSFYLGNHETNYTLHLVAITGNVPNAIPENKDLVFSTWDHKAKGHFNCPEG YSGGWWWHDECGENNLNGKYNKPRASSKPERRRGLSWKSQNGRLYSIKSTKMLIH PTDSESFE |
| 26 | 241KQ | GIPAECTTIYNRGEHTSGMYAIRPSNSQVFHVYCDVISGSPWTLIQHRIDGSQNF NETWENYKYGFGRLDGEFWLGLEKIYSIVKQSNYVLRIELEDWKDNKHYIEYSFY LGNHETNYTLHLVAITGNVPNAIPENKDLVFSTWDHKAKGHFNCPEGYSGGWWWH DECGENNLNGKYNKPRAQSKPERRRGLSWKSQNGRLYSIKSTKMLIHPTDSESFE |
| 27 | 241KS | GIPAECTTIYNRGEHTSGMYAIRPSNSQVFHVYCDVISGSPWTLIQHRIDGSQNF NETWENYKYGFGRLDGEFWLGLEKIYSIVKQSNYVLRIELEDWKDNKHYIEYSFY LGNHETNYTLHLVAITGNVPNAIPENKDLVFSTWDHKAKGHFNCPEGYSGGWWWH DECGENNLNGKYNKPRASSKPERRRGLSWKSQNGRLYSIKSTKMLIHPTDSESFE |
| 28 | 242KQ | IPAECTTIYNRGEHTSGMYAIRPSNSQVFHVYCDVISGSPWTLIQHRIDGSQNFN ETWENYKYGFGRLDGEFWLGLEKIYSIVKQSNYVLRIELEDWKDNKHYIEYSFYL GNHETNYTLHLVAITGNVPNAIPENKDLVFSTWDHKAKGHFNCPEGYSGGWWWHD ECGENNLNGKYNKPRAQSKPERRRGLSWKSQNGRLYSIKSTKMLIHPTDSESFE |
| 29 | 242KS | IPAECTTIYNRGEHTSGMYAIRPSNSQVFHVYCDVISGSPWTLIQHRIDGSQNFN ETWENYKYGFGRLDGEFWLGLEKIYSIVKQSNYVLRIELEDWKDNKHYIEYSFYL GNHETNYTLHLVAITGNVPNAIPENKDLVFSTWDHKAKGHFNCPEGYSGGWWWHD ECGENNLNGKYNKPRASSKPERRRGLSWKSQNGRLYSIKSTKMLIHPTDSESFE |
| 30 | 225-455KQ | TTPFLQLNEIRNVKHDGIPAECTTIYNRGEHTSGMYAIRPSNSQVFHVYCDVISG SPWTLIQHRIDGSQNFNETWENYKYGFGRLDGEFWLGLEKIYSIVKQSNYVLRIE LEDWKDNKHYIEYSFYLGNHETNYTLHLVAITGNVPNAIPENKDLVFSTWDHKAK GHFNCPEGYSGGWWWHDECGENNLNGKYNKPRAQSKPERRRGLSWKSQNGRLYSI KSTKMLIHPTD |
| 31 | 225-455KS | TTPFLQLNEIRNVKHDGIPAECTTIYNRGEHTSGMYAIRPSNSQVFHVYCDVISG SPWTLIQHRIDGSQNFNETWENYKYGFGRLDGEFWLGLEKIYSIVKQSNYVLRIE LEDWKDNKHYIEYSFYLGNHETNYTLHLVAITGNVPNAIPENKDLVFSTWDHKAK GHFNCPEGYSGGWWWHDECGENNLNGKYNKPRASSKPERRRGLSWKSQNGRLYSI KSTKMLIHPTD |
| 32 | 226-455KQ | TPFLQLNEIRNVKHDGIPAECTTIYNRGEHTSGMYAIRPSNSQVFHVYCDVISGS PWTLIQHRIDGSQNFNETWENYKYGFGRLDGEFWLGLEKIYSIVKQSNYVLRIEL EDWKDNKHYIEYSFYLGNHETNYTLHLVAITGNVPNAIPENKDLVFSTWDHKAKG HFNCPEGYSGGWWWHDECGENNLNGKYNKPRAQSKPERRRGLSWKSQNGRLYSIK STKMLIHPTD |

-continued

| SEQ ID | Construct | Sequence |
|---|---|---|
| 33 | 226-455KS | TPFLQLNEIRNVKHDGIPAECTTIYNRGEHTSGMYAIRPSNSQVFHVYCDVISGS PWTLIQHRIDGSQNFNETWENYKYGFGRLDGEFWLGLEKIYSIVKQSNYVLRIEL EDWKDNKHYIEYSFYLGNHETNYTLHLVAITGNVPNAIPENKDLVFSTWDHKAKG HFNCPEGYSGGWWWHDECGENNLNGKYNKPRASSKPERRRGLSWKSQNGRLYSIK STKMLIHPTD |
| 34 | 228-455KQ | FLQLNEIRNVKHDGIPAECTTIYNRGEHTSGMYAIRPSNSQVFHVYCDVISGSPW TLIQHRIDGSQNFNETWENYKYGFGRLDGEFWLGLEKIYSIVKQSNYVLRIELED WKDNKHYIEYSFYLGNHETNYTLHLVAITGNVPNAIPENKDLVFSTWDHKAKGHF NCPEGYSGGWWWHDECGENNLNGKYNKPRAQSKPERRRGLSWKSQNGRLYSIKST KMLIHPTD |
| 35 | 228-455KS | FLQLNEIRNVKHDGIPAECTTIYNRGEHTSGMYAIRPSNSQVFHVYCDVISGSPW TLIQHRIDGSQNFNETWENYKYGFGRLDGEFWLGLEKIYSIVKQSNYVLRIELED WKDNKHYIEYSFYLGNHETNYTLHLVAITGNVPNAIPENKDLVFSTWDHKAKGHF NCPEGYSGGWWWHDECGENNLNGKYNKPRASSKPERRRGLSWKSQNGRLYSIKST KMLIHPTD |
| 36 | 233-455KQ | EIRNVKHDGIPAECTTIYNRGEHTSGMYAIRPSNSQVFHVYCDVISGSPWTLIQH RIDGSQNFNETWENYKYGFGRLDGEFWLGLEKIYSIVKQSNYVLRIELEDWKDNK HYIEYSFYLGNHETNYTLHLVAITGNVPNAIPENKDLVFSTWDHKAKGHFNCPEG YSGGWWWHDECGENNLNGKYNKPRAQSKPERRRGLSWKSQNGRLYSIKSTKMLIH PTD |
| 37 | 233-455KS | EIRNVKHDGIPAECTTIYNRGEHTSGMYAIRPSNSQVFHVYCDVISGSPWTLIQH RIDGSQNFNETWENYKYGFGRLDGEFWLGLEKIYSIVKQSNYVLRIELEDWKDNK HYIEYSFYLGNHETNYTLHLVAITGNVPNAIPENKDLVFSTWDHKAKGHFNCPEG YSGGWWWHDECGENNLNGKYNKPRASSKPERRRGLSWKSQNGRLYSIKSTKMLIH PTD |
| 38 | 241-455KQ | GIPAECTTIYNRGEHTSGMYAIRPSNSQVFHVYCDVISGSPWTLIQHRIDGSQNF NETWENYKYGFGRLDGEFWLGLEKIYSIVKQSNYVLRIELEDWKDNKHYIEYSFY LGNHETNYTLHLVAITGNVPNAIPENKDLVFSTWDHKAKGHFNCPEGYSGGWWWH DECGENNLNGKYNKPRAQSKPERRRGLSWKSQNGRLYSIKSTKMLIHPTD |
| 39 | 241-455KS | GIPAECTTIYNRGEHTSGMYAIRPSNSQVFHVYCDVISGSPWTLIQHRIDGSQNF NETWENYKYGFGRLDGEFWLGLEKIYSIVKQSNYVLRIELEDWKDNKHYIEYSFY LGNHETNYTLHLVAITGNVPNAIPENKDLVFSTWDHKAKGHFNCPEGYSGGWWWH DECGENNLNGKYNKPRASSKPERRRGLSWKSQNGRLYSIKSTKMLIHPTD |
| 40 | 242-455KQ | IPAECTTIYNRGEHTSGMYAIRPSNSQVFHVYCDVISGSPWTLIQHRIDGSQNFN ETWENYKYGFGRLDGEFWLGLEKIYSIVKQSNYVLRIELEDWKDNKHYIEYSFYL GNHETNYTLHLVAITGNVPNAIPENKDLVFSTWDHKAKGHFNCPEGYSGGWWWHD ECGENNLNGKYNKPRAQSKPERRRGLSWKSQNGRLYSIKSTKMLIHPTD |
| 41 | 242-455KS | IPAECTTIYNRGEHTSGMYAIRPSNSQVFHVYCDVISGSPWTLIQHRIDGSQNFN ETWENYKYGFGRLDGEFWLGLEKIYSIVKQSNYVLRIELEDWKDNKHYIEYSFYL GNHETNYTLHLVAITGNVPNAIPENKDLVFSTWDHKAKGHFNCPEGYSGGWWWHD ECGENNLNGKYNKPRASSKPERRRGLSWKSQNGRLYSIKSTKMLIHPTD |
| 42 | Canine 227KQ | FLHLNETKNVEHNDIPANCTTIYNRGEHTSGIYSIRPSNSQVFNVYCDVKSGSSW TLIQHRIDGSQNFNETWENYRYGFGRLDGEFWLGLEKIYSIVKQSNYILRIELED WNDNKHYIEYFFHLGNHETNYTLHLVEITGNILNALPEHKDLVFSTWDHKAKGHV NCPESYSGGWWWHNVCGENNLNGKYNKQRAQTKPERRRGLYWKSQNGRLYSIKST KMLIHPIDSESSE |
| 43 | Canine 227KS | FLHLNETKNVEHNDIPANCTTIYNRGEHTSGIYSIRPSNSQVFNVYCDVKSGSSW TLIQHRIDGSQNFNETWENYRYGFGRLDGEFWLGLEKIYSIVKQSNYILRIELED WNDNKHYIEYFFHLGNHETNYTLHLVEITGNILNALPEHKDLVFSTWDHKAKGHV NCPESYSGGWWWHNVCGENNLNGKYNKQRASTKPERRRGLYWKSQNGRLYSIKST KMLIHPIDSESSE |
| 44 | Nucleic acid sequence 225WT | ACTACTCCCTTTCTTCAGTTGAATGAAATAAGAAATGTAAAACATGATGGCATTC CTGCTGAATGTACCACCATTTATAACAGAGGTGAACATACAAGTGGCATGTATGC CATCAGACCCAGCAACTCTCAAGTTTTTCATGTCTACTGTGATGTTATATCAGGT AGTCCATGGACATTAATTCAACATCGAATAGATGGATCACAAAACTTCAATGAAA CGTGGGAGAACTACAAATATGGTTTTGGGAGGCTTGATGGAGAATTTTGGTTGGG CCTAGAGAAGATATACTCCATAGTGAAGCAATCTAATTATGTTTTACGAATTGAG TTGGAAGACTGGAAAGACAACAAACATTATATTGAATATTCTTTTTACTTGGGAA ATCACGAAACCAACTATACGCTACATCTAGTTGCGATTACTGGCAATGTCCCCAA TGCAATCCCGGAAAACAAAGATTTGGTGTTTTCTACTTGGGATCACAAAGCAAAA GGACACTTCAACTGTCCAGAGGGTTATTCAGGAGGCTGGTGGTGGCATGATGAGT GTGGAGAAAACAACCTAAATGGTAAATATAACAAACCAAGAGCAAAATCTAAGCC AGAGAGGAGAGAAGAGGATTATCTTGGAAGTCTCAAAATGGAAGGTTATACTCTATA AAATCAACCAAAATGTTGATCCATCCAACAGATTCAGAAAGCTTTGAA |

-continued

| SEQ ID | Construct | Sequence |
|---|---|---|
| 45 | Nucleic acid sequence 225KQ | ACTACTCCCTTTCTTCAGTTGAATGAAATAAGAAATGTAAAACATGATGGCATTC<br>CTGCTGAATGTACCACCATTTATAACAGAGGTGAACATACAAGTGGCATGTATGC<br>CATCAGACCCAGCAACTCTCAAGTTTTTCATGTCTACTGTGATGTTATATCAGGT<br>AGTCCATGGACATTAATTCAACATCGAATAGATGGATCACAAAACTTCAATGAAA<br>CGTGGGAGAACTACAAATATGGTTTTGGGAGGCTTGATGGAGAATTTTGGTTGGG<br>CCTAGAGAAGATATACTCCATAGTGAAGCAATCTAATTATGTTTTACGAATTGAG<br>TTGGAAGACTGGAAAGACAACAAACATTATATTGAATATTCTTTTTACTTGGGAA<br>ATCACGAAACCAACTATACGCTACATCTAGTTGCGATTACTGGCAATGTCCCCAA<br>TGCAATCCCGGAAAACAAAGATTTGGTGTTTTCTACTTGGGATCACAAAGCAAAA<br>GGACACTTCAACTGTCCAGAGGGTTATTCAGGAGGCTGGTGGTGGCATGATGAGT<br>GTGGAGAAAACAACCTAAATGGTAAATATAACAAACCAAGAGCACAATCTAAGCC<br>AGAGAGGAGAAGAGGATTATCTTGGAAGTCTCAAAATGGAAGGTTATACTCTATA<br>AAATCAACCAAAATGTTGATCCATCCAACAGATTCAGAAAGCTTTGAA |
| 46 | Nucleic acid sequence 225KS | ACTACTCCCTTTCTTCAGTTGAATGAAATAAGAAATGTAAAACATGATGGCATTC<br>CTGCTGAATGTACCACCATTTATAACAGAGGTGAACATACAAGTGGCATGTATGC<br>CATCAGACCCAGCAACTCTCAAGTTTTTCATGTCTACTGTGATGTTATATCAGGT<br>AGTCCATGGACATTAATTCAACATCGAATAGATGGATCACAAAACTTCAATGAAA<br>CGTGGGAGAACTACAAATATGGTTTTGGGAGGCTTGATGGAGAATTTTGGTTGGG<br>CCTAGAGAAGATATACTCCATAGTGAAGCAATCTAATTATGTTTTACGAATTGAG<br>TTGGAAGACTGGAAAGACAACAAACATTATATTGAATATTCTTTTTACTTGGGAA<br>ATCACGAAACCAACTATACGCTACATCTAGTTGCGATTACTGGCAATGTCCCCAA<br>TGCAATCCCGGAAAACAAAGATTTGGTGTTTTCTACTTGGGATCACAAAGCAAAA<br>GGACACTTCAACTGTCCAGAGGGTTATTCAGGAGGCTGGTGGTGGCATGATGAGT<br>GTGGAGAAAACAACCTAAATGGTAAATATAACAAACCAAGAGCAAGCTCTAAGCC<br>AGAGAGGAGAAGAGGATTATCTTGGAAGTCTCAAAATGGAAGGTTATACTCTATA<br>AAATCAACCAAAATGTTGATCCATCCAACAGATTCAGAAAGCTTTGAA |
| 47 | Nucleic acid sequence 226KQ | ACTCCCTTTCTTCAGTTGAATGAAATAAGAAATGTAAAACATGATGGCATTCCTG<br>CTGAATGTACCACCATTTATAACAGAGGTGAACATACAAGTGGCATGTATGCCAT<br>CAGACCCAGCAACTCTCAAGTTTTTCATGTCTACTGTGATGTTATATCAGGTAGT<br>CCATGGACATTAATTCAACATCGAATAGATGGATCACAAAACTTCAATGAAACGT<br>GGGAGAACTACAAATATGGTTTTGGGAGGCTTGATGGAGAATTTTGGTTGGGCCT<br>AGAGAAGATATACTCCATAGTGAAGCAATCTAATTATGTTTTACGAATTGAGTTG<br>GAAGACTGGAAAGACAACAAACATTATATTGAATATTCTTTTTACTTGGGAAATC<br>ACGAAACCAACTATACGCTACATCTAGTTGCGATTACTGGCAATGTCCCCAATGC<br>AATCCCGGAAAACAAAGATTTGGTGTTTTCTACTTGGGATCACAAAGCAAAAGGA<br>CACTTCAACTGTCCAGAGGGTTATTCAGGAGGCTGGTGGTGGCATGATGAGTGTG<br>GAGAAAACAACCTAAATGGTAAATATAACAAACCAAGAGCACAATCTAAGCCAGA<br>GAGGAGAAGAGGATTATCTTGGAAGTCTCAAAATGGAAGGTTATACTCTATAAAA<br>TCAACCAAAATGTTGATCCATCCAACAGATTCAGAAAGCTTTGAA |
| 48 | Nucleic acid sequence 226KS | ACTCCCTTTCTTCAGTTGAATGAAATAAGAAATGTAAAACATGATGGCATTCCTG<br>CTGAATGTACCACCATTTATAACAGAGGTGAACATACAAGTGGCATGTATGCCAT<br>CAGACCCAGCAACTCTCAAGTTTTTCATGTCTACTGTGATGTTATATCAGGTAGT<br>CCATGGACATTAATTCAACATCGAATAGATGGATCACAAAACTTCAATGAAACGT<br>GGGAGAACTACAAATATGGTTTTGGGAGGCTTGATGGAGAATTTTGGTTGGGCCT<br>AGAGAAGATATACTCCATAGTGAAGCAATCTAATTATGTTTTACGAATTGAGTTG<br>GAAGACTGGAAAGACAACAAACATTATATTGAATATTCTTTTTACTTGGGAAATC<br>ACGAAACCAACTATACGCTACATCTAGTTGCGATTACTGGCAATGTCCCCAATGC<br>AATCCCGGAAAACAAAGATTTGGTGTTTTCTACTTGGGATCACAAAGCAAAAGGA<br>CACTTCAACTGTCCAGAGGGTTATTCAGGAGGCTGGTGGTGGCATGATGAGTGTG<br>GAGAAAACAACCTAAATGGTAAATATAACAAACCAAGAGCAAGCTCTAAGCCAGA<br>GAGGAGAAGAGGATTATCTTGGAAGTCTCAAAATGGAAGGTTATACTCTATAAAA<br>TCAACCAAAATGTTGATCCATCCAACAGATTCAGAAAGCTTTGAA |
| 49 | Nucleic acid sequence 228KQ | TTTCTTCAGTTGAATGAAATAAGAAATGTAAAACATGATGGCATTCCTGCTGAAT<br>GTACCACCATTTATAACAGAGGTGAACATACAAGTGGCATGTATGCCATCAGACC<br>CAGCAACTCTCAAGTTTTTCATGTCTACTGTGATGTTATATCAGGTAGTCCATGG<br>ACATTAATTCAACATCGAATAGATGGATCACAAAACTTCAATGAAACGTGGGAGA<br>ACTACAAATATGGTTTTGGGAGGCTTGATGGAGAATTTTGGTTGGGCCTAGAGAA<br>GATATACTCCATAGTGAAGCAATCTAATTATGTTTTACGAATTGAGTTGGAAGAC<br>TGGAAAGACAACAAACATTATATTGAATATTCTTTTTACTTGGGAAATCACGAAA<br>CCAACTATACGCTACATCTAGTTGCGATTACTGGCAATGTCCCCAATGCAATCCC<br>GGAAAACAAAGATTTGGTGTTTTCTACTTGGGATCACAAAGCAAAAGGACACTTC<br>AACTGTCCAGAGGGTTATTCAGGAGGCTGGTGGTGGCATGATGAGTGTGGAGAAA<br>ACAACCTAAATGGTAAATATAACAAACCAAGAGCACAATCTAAGCCAGAGAGGAG<br>AAGAGGATTATCTTGGAAGTCTCAAAATGGAAGGTTATACTCTATAAAATCAACC<br>AAAATGTTGATCCATCCAACAGATTCAGAAAGCTTTGAA |
| 50 | Nucleic acid sequence 228KS | TTTCTTCAGTTGAATGAAATAAGAAATGTAAAACATGATGGCATTCCTGCTGAAT<br>GTACCACCATTTATAACAGAGGTGAACATACAAGTGGCATGTATGCCATCAGACC<br>CAGCAACTCTCAAGTTTTTCATGTCTACTGTGATGTTATATCAGGTAGTCCATGG<br>ACATTAATTCAACATCGAATAGATGGATCACAAAACTTCAATGAAACGTGGGAGA<br>ACTACAAATATGGTTTTGGGAGGCTTGATGGAGAATTTTGGTTGGGCCTAGAGAA |

-continued

| SEQ ID | Construct | Sequence |
| --- | --- | --- |
| | | GATATACTCCATAGTGAAGCAATCTAATTATGTTTTACGAATTGAGTTGGAAGAC<br>TGGAAAGACAACAAACATTATATTGAATATTCTTTTTACTTGGGAAATCACGAAA<br>CCAACTATACGCTACATCTAGTTGCGATTACTGGCAATGTCCCCAATGCAATCCC<br>GGAAAACAAAGATTTGGTGTTTTCTACTTGGGATCACAAAGCAAAAGGACACTTC<br>AACTGTCCAGAGGGTTATTCAGGAGGCTGGTGGTGGCATGATGAGTGTGGAGAAA<br>ACAACCTAAATGGTAAATATAACAAACCAAGAGCAAGCTCTAAGCCAGAGAGGAG<br>AAGAGGATTATCTTGGAAGTCTCAAAATGGAAGGTTATACTCTATAAAATCAACC<br>AAAATGTTGATCCATCCAACAGATTCAGAAAGCTTTGAA |
| 51 | Nucleic acid sequence 233KQ | GAAATAAGAAATGTAAAACATGATGGCATTCCTGCTGAATGTACCACCATTTATA<br>ACAGAGGTGAACATACAAGTGGCATGTATGCCATCAGACCCAGCAACTCTCAAGT<br>TTTTCATGTCTACTGTGATGTTATATCAGGTAGTCCATGGACATTAATTCAACAT<br>CGAATAGATGGATCACAAAACTTCAATGAAACGTGGGAGAACTACAAATATGGTT<br>TTGGGAGGCTTGATGGAGAATTTTGGTTGGGCCTAGAGAAGATATACTCCATAGT<br>GAAGCAATCTAATTATGTTTTACGAATTGAGTTGGAAGACTGGAAAGACAACAAA<br>CATTATATTGAATATTCTTTTTACTTGGGAAATCACGAAACCAACTATACGCTAC<br>ATCTAGTTGCGATTACTGGCAATGTCCCCAATGCAATCCCGGAAAACAAAGATTT<br>GGTGTTTTCTACTTGGGATCACAAAGCAAAAGGACACTTCAACTGTCCAGAGGGT<br>TATTCAGGAGGCTGGTGGTGGCATGATGAGTGTGGAGAAAACAACCTAAATGGTA<br>AATATAACAAACCAAGAGCACAATCTAAGCCAGAGAGGAGAAGAGGATTATCTTG<br>GAAGTCTCAAAATGGAAGGTTATACTCTATAAAATCAACCAAAATGTTGATCCAT<br>CCAACAGATTCAGAAAGCTTTGAA |
| 52 | Nucleic acid sequence 233KS | GAAATAAGAAATGTAAAACATGATGGCATTCCTGCTGAATGTACCACCATTTATA<br>ACAGAGGTGAACATACAAGTGGCATGTATGCCATCAGACCCAGCAACTCTCAAGT<br>TTTTCATGTCTACTGTGATGTTATATCAGGTAGTCCATGGACATTAATTCAACAT<br>CGAATAGATGGATCACAAAACTTCAATGAAACGTGGGAGAACTACAAATATGGTT<br>TTGGGAGGCTTGATGGAGAATTTTGGTTGGGCCTAGAGAAGATATACTCCATAGT<br>GAAGCAATCTAATTATGTTTTACGAATTGAGTTGGAAGACTGGAAAGACAACAAA<br>CATTATATTGAATATTCTTTTTACTTGGGAAATCACGAAACCAACTATACGCTAC<br>ATCTAGTTGCGATTACTGGCAATGTCCCCAATGCAATCCCGGAAAACAAAGATTT<br>GGTGTTTTCTACTTGGGATCACAAAGCAAAAGGACACTTCAACTGTCCAGAGGGT<br>TATTCAGGAGGCTGGTGGTGGCATGATGAGTGTGGAGAAAACAACCTAAATGGTA<br>AATATAACAAACCAAGAGCAAGCTCTAAGCCAGAGAGGAGAAGAGGATTATCTTG<br>GAAGTCTCAAAATGGAAGGTTATACTCTATAAAATCAACCAAAATGTTGATCCAT<br>CCAACAGATTCAGAAAGCTTTGAA |
| 53 | Nucleic acid sequence 241KQ | GGCATTCCTGCTGAATGTACCACCATTTATAACAGAGGTGAACATACAAGTGGCA<br>TGTATGCCATCAGACCCAGCAACTCTCAAGTTTTTCATGTCTACTGTGATGTTAT<br>ATCAGGTAGTCCATGGACATTAATTCAACATCGAATAGATGGATCACAAAACTTC<br>AATGAAACGTGGGAGAACTACAAATATGGTTTTGGGAGGCTTGATGGAGAATTTT<br>GGTTGGGCCTAGAGAAGATATACTCCATAGTGAAGCAATCTAATTATGTTTTACG<br>AATTGAGTTGGAAGACTGGAAAGACAACAAACATTATATTGAATATTCTTTTTAC<br>TTGGGAAATCACGAAACCAACTATACGCTACATCTAGTTGCGATTACTGGCAATG<br>TCCCCAATGCAATCCCGGAAAACAAAGATTTGGTGTTTTCTACTTGGGATCACAA<br>AGCAAAAGGACACTTCAACTGTCCAGAGGGTTATTCAGGAGGCTGGTGGTGGCAT<br>GATGAGTGTGGAGAAAACAACCTAAATGGTAAATATAACAAACCAAGAGCACAAT<br>CTAAGCCAGAGAGGAGAAGAGGATTATCTTGGAAGTCTCAAAATGGAAGGTTATA<br>CTCTATAAAATCAACCAAAATGTTGATCCATCCAACAGATTCAGAAAGCTTTGAA |
| 54 | Nucleic acid sequence 241KS | GGCATTCCTGCTGAATGTACCACCATTTATAACAGAGGTGAACATACAAGTGGCA<br>TGTATGCCATCAGACCCAGCAACTCTCAAGTTTTTCATGTCTACTGTGATGTTAT<br>ATCAGGTAGTCCATGGACATTAATTCAACATCGAATAGATGGATCACAAAACTTC<br>AATGAAACGTGGGAGAACTACAAATATGGTTTTGGGAGGCTTGATGGAGAATTTT<br>GGTTGGGCCTAGAGAAGATATACTCCATAGTGAAGCAATCTAATTATGTTTTACG<br>AATTGAGTTGGAAGACTGGAAAGACAACAAACATTATATTGAATATTCTTTTTAC<br>TTGGGAAATCACGAAACCAACTATACGCTACATCTAGTTGCGATTACTGGCAATG<br>TCCCCAATGCAATCCCGGAAAACAAAGATTTGGTGTTTTCTACTTGGGATCACAA<br>AGCAAAAGGACACTTCAACTGTCCAGAGGGTTATTCAGGAGGCTGGTGGTGGCAT<br>GATGAGTGTGGAGAAAACAACCTAAATGGTAAATATAACAAACCAAGAGCAAGCT<br>CTAAGCCAGAGAGGAGAAGAGGATTATCTTGGAAGTCTCAAAATGGAAGGTTATA<br>CTCTATAAAATCAACCAAAATGTTGATCCATCCAACAGATTCAGAAAGCTTTGAA |
| 55 | Nucleic acid sequence 242KQ | ATTCCTGCTGAATGTACCACCATTTATAACAGAGGTGAACATACAAGTGGCATGT<br>ATGCCATCAGACCCAGCAACTCTCAAGTTTTTCATGTCTACTGTGATGTTATATC<br>AGGTAGTCCATGGACATTAATTCAACATCGAATAGATGGATCACAAAACTTCAAT<br>GAAACGTGGGAGAACTACAAATATGGTTTTGGGAGGCTTGATGGAGAATTTTGGT<br>TGGGCCTAGAGAAGATATACTCCATAGTGAAGCAATCTAATTATGTTTTACGAAT<br>TGAGTTGGAAGACTGGAAAGACAACAAACATTATATTGAATATTCTTTTTACTTG<br>GGAAATCACGAAACCAACTATACGCTACATCTAGTTGCGATTACTGGCAATGTCC<br>CCAATGCAATCCCGGAAAACAAAGATTTGGTGTTTTCTACTTGGGATCACAAAGC<br>AAAAGGACACTTCAACTGTCCAGAGGGTTATTCAGGAGGCTGGTGGTGGCATGAT<br>GAGTGTGGAGAAAACAACCTAAATGGTAAATATAACAAACCAAGAGCACAATCTA<br>AGCCAGAGAGGAGAAGAGGATTATCTTGGAAGTCTCAAAATGGAAGGTTATACTC<br>TATAAAATCAACCAAAATGTTGATCCATCCAACAGATTCAGAAAGCTTTGAA |

-continued

| SEQ ID | Construct | Sequence |
|---|---|---|
| 56 | Nucleic acid sequence 242KS | ATTCCTGCTGAATGTACCACCATTTATAACAGAGGTGAACATACAAGTGGCATGT ATGCCATCAGACCCAGCAACTCTCAAGTTTTTCATGTCTACTGTGATGTTATATC AGGTAGTCCATGGACATTAATTCAACATCGAATAGATGGATCACAAAACTTCAAT GAAACGTGGGAGAACTACAAATATGGTTTTGGGAGGCTTGATGGAGAATTTTGGT TGGGCCTAGAGAAGATATACTCCATAGTGAAGCAATCTAATTATGTTTTACGAAT TGAGTTGGAAGACTGGAAAGACAACAAACATTATATTGAATATTCTTTTTACTTG GGAAATCACGAAACCAACTATACGCTACATCTAGTTGCGATTACTGGCAATGTCC CCAATGCAATCCCGGAAAACAAAGATTTGGTGTTTTCTACTTGGGATCACAAAGC AAAAGGACACTTCAACTGTCCAGAGGGTTATTCAGGAGGCTGGTGGTGGCATGAT GAGTGTGGAGAAAACAACCTAAATGGTAAATATAACAAACCAAGAGCAAGCTCTA AGCCAGAGAGGAGAAGAGGATTATCTTGGAAGTCTCAAAATGGAAGGTTATACTC TATAAAATCAACCAAAATGTTGATCCATCCAACAGATTCAGAAAGCTTTGAA |
| 57 | Nucleic acid sequence c227KQ | TTTTTGCATCTCAACGAAACGAAGAATGTCGAACACAACGACATTCCGGCAAATT GCACAACTATCTACAATAGAGGCGAACATACGTCCGGTATCTACTCCATTAGACC TTCAAACAGCCAGGTATTCAATGTGTACTGCGATGTAAAGTCAGGATCGTCATGG ACACTGATCCAGCATAGGATCGACGGGTCCCAGAACTTCAACGAGACATGGGAGA ACTACCGCTATGGATTTGGAAGGCTGGATGGGGAGTTCTGGTTGGGACTTGAGAA AATCTACAGCATTGTGAAGCAGTCGAACTACATTCTCCGGATTGAACTGGAGGAC TGGAATGACAACAAACACTACATCGAGTATTTCTTTCATCTCGGCAACCATGAAA CGAATTACACCTTGCACCTTGTGGAAATCACGGGCAACATTTTGAACGCGCTGCC AGAACACAAAGACCTGGTGTTTTCGACATGGGATCACAAAGCAAAGGGGCACGTG AACTGTCCCGAATCATATAGCGGGGGATGGTGGTGGCACAATGTCTGTGGTGAGA ACAATCTCAACGGGAAATACAATAAGCAGCGAGCTCAGACGAAACCCGAGCGGCG GAGAGGTCTGTATTGGAAGTCGCAGAATGGACGCCTGTATTCGATCAAATCGACG AAAATGCTCATCCACCCCATCGACTCCGAATCGTCGGAG |

What is claimed is:

1. A method of treating or ameliorating arthritis or articular cartilage damage in a subject, the method comprising administering to a joint of the subject a therapeutically effective amount of a polypeptide comprising an amino acid sequence that has at least 95% amino acid sequence identity to an amino acid sequence selected from the group of sequences of TABLE 1, wherein the polypeptide comprises an amino acid that is a polar amino acid other than K or R at position 423, as determined with reference to SEQ ID NO:1, and wherein the polypeptide has chondrogenic activity.

2. The method of claim 1, wherein the polypeptide comprises an amino acid sequence that has at least 95% sequence identity to an amino acid sequence selected from any one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29.

3. The method of claim 1, wherein the polypeptide comprises an amino acid sequence selected from any one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, or SEQ ID NO:29.

4. The method of claim 1, wherein the polypeptide consists of an amino acid sequence that has at least 95% sequence identity to an amino acid sequence selected from any one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, or SEQ ID NO:29.

5. The method of claim 1, wherein the polypeptide consists of an amino acid sequence selected from any one of SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, or SEQ ID NO:41, SEQ ID NO:14, SEQ ID NO:15, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:26, SEQ ID NO:27, SEQ ID NO:28, or SEQ ID NO:29.

6. The method of claim 1, wherein the amino acid at position 423 of the polypeptide is Q or S.

7. The method of claim 1, wherein the amino acid at position 423 of the polypeptide is Q.

8. The method of claim 1, wherein the amino acid at position 423 of the polypeptide is S.

9. The method of claim 1, wherein the polypeptide is PEGylated.

10. The method of claim 1, wherein the polypeptide is fused to a heterologous peptide selected from any of human serum albumin (HSA), an immunoglobulin heavy chain constant region (Fc), a polyhistidine, a glutathione S transferase (GST), a thioredoxin, a protein A, a protein G, or a maltose binding protein (MBP), or a fragment thereof.

11. The method of claim 1, wherein the subject has arthritis.

12. The method of claim 1, wherein the subject has articular cartilage damage.

13. The method of claim 1, wherein the arthritis is osteoarthritis, trauma arthritis, or autoimmune arthritis.

14. The method of claim 1, further comprising administering to the subject one or more additional chondrogenic factors.

15. The method of claim 1, further comprising administering to the subject hyaluronic acid or a derivative thereof.

16. The method of claim 1, further comprising administering to the subject an agent selected from the group consisting of oral salmon calcitonin, SD-6010 (iNOS inhibitor), vitamin D3 (choliecalciferol), collagen hydrolyzate, FGF18, BMP7, rusalatide acetate, avocado soy unsaponifiables (ASU), kartogenin, a steroid, and a non-steroidal anti-inflammatory agent (NSAID).

17. The method of claim 1, further comprising performing a surgical procedure to an affected joint in the subject.

18. The method of claim 17, wherein administering the polypeptide occurs during or after the surgical procedure.

19. The method of claim 1, wherein administering the polypeptide occurs in conjunction with any one of bone marrow stimulation, cartilage replacement, autologous chondrocyte implantation (ACI), matrix-induced autologous chondrocyte implantation (MACI).

20. The method of claim 1, wherein the polypeptide is administered in a matrix or biocompatible scaffold.

21. The method of claim 1, wherein the arthritis is osteoarthritis.

* * * * *